(12) United States Patent
Mizukoshi et al.

(10) Patent No.: US 7,700,808 B2
(45) Date of Patent: Apr. 20, 2010

(54) 1-3-BIS(SUBSTITUTED PHENYL)-3-HYDROXYPROPAN-1-ONE OR 2-PROPEN-1-ONE COMPOUND, AND SALT THEREOF

(75) Inventors: Takashi Mizukoshi, Funabashi (JP); Yasuhiro Sakurai, Funabashi (JP); Kazutaka Matoba, Funabashi (JP); Manabu Yaosaka, Funabashi (JP)

(73) Assignee: Nissan Chemical Industries, Ltd., Tokyo (JP)

( * ) Notice: Subject to any disclaimer, the term of this patent is extended or adjusted under 35 U.S.C. 154(b) by 10 days.

(21) Appl. No.: 12/087,019

(22) PCT Filed: Dec. 25, 2006

(86) PCT No.: PCT/JP2006/325818

§ 371 (c)(1),
(2), (4) Date: Jun. 24, 2008

(87) PCT Pub. No.: WO2007/074789

PCT Pub. Date: Jul. 5, 2007

(65) Prior Publication Data

US 2009/0023923 A1  Jan. 22, 2009

(30) Foreign Application Priority Data

Dec. 26, 2005  (JP) .............................. 2005-372712

(51) Int. Cl.
*C07C 49/303* (2006.01)
*C07C 69/76* (2006.01)
*C07C 233/00* (2006.01)
*C07C 63/06* (2006.01)
*C07D 239/24* (2006.01)
*C07D 307/02* (2006.01)
*C07D 213/02* (2006.01)

(52) U.S. Cl. ........................ 568/329; 564/169; 562/459; 560/51; 549/496; 546/328; 544/344

(58) Field of Classification Search ................. 568/329; 564/169; 562/459; 560/51; 549/496; 546/328; 544/344

See application file for complete search history.

(56) References Cited

U.S. PATENT DOCUMENTS

| | | | |
|---|---|---|---|
| 3,931,152 A | 1/1976 | Tomcufcik et al. | |
| 5,514,816 A | 5/1996 | Ackermann et al. | |
| 5,629,332 A | 5/1997 | Kodama et al. | |
| 5,756,814 A | 5/1998 | Lin et al. | |
| 5,990,323 A | 11/1999 | Clubb | |
| 2005/0250822 A1 | 11/2005 | Mita et al. | |
| 2007/0066617 A1 | 3/2007 | Mita et al. | |

FOREIGN PATENT DOCUMENTS

| | | |
|---|---|---|
| DE | 197 27 042 A1 | 1/1998 |
| EP | 0 811 608 A1 | 12/1997 |
| JP | A-50-106960 | 8/1975 |
| JP | A-7-316140 | 12/1995 |
| JP | A-11-236363 | 8/1999 |
| JP | A-2005-35964 | 2/2005 |
| WO | WO 96/11200 | 4/1996 |
| WO | WO 96/19477 | 6/1996 |
| WO | WO 2004/018410 A1 | 3/2004 |
| WO | WO 2005/085216 A1 | 9/2005 |

OTHER PUBLICATIONS

Bartoli et al. Highly Chemoselective Addition of (o-Nitrobenzoyl) Silanes to Nonenolizable Aldehydes. Journal of Organic Chemistry, 1987, vol. 52, pp. 4381-4384.*

Alper et al. Dehalogenation and Condensation Reactivities of Molybdenum Carbonyls with Activated Halides. Journal of Organic Chemistry, 1976, 41 (5), pp. 806-808.*

Moskalev et al.; "Synthesis of Functionally Substituted Alcohols Containing a CF3 Group by the Condensation of Aryl and Heteroaryl Trifluoromethyl Ketones with CH Acids;" *Zhurnal Organicheskoi Khimii*; vol. 26; No. 10; pp. 2205-2208; Oct. 1990. (w/ Translation).

E.P. Kohler et al.; "The Reaction Between Organic Magnesium Compounds and Alpha Bromo Ketones;" Journal of the American Chemical Society; vol. 57; 1935; pp. 217-224.

Natali M. Nevar et al.; "One Step Preparation of 1,4-Diketones from Methyl Ketones and α-Bromomethyl Ketones in the Presence of ZnCl₂•-BuOH•Et₂NR as a Condensation Agent;" Synthesis; 2000; No. 9; pp. 1259-1262.

(Continued)

*Primary Examiner*—Sikarl A Witherspoon
(74) *Attorney, Agent, or Firm*—Oliff & Berridge, PLC

(57) ABSTRACT

There is provided a novel process intermediate represented by the general formula (1) or (2):

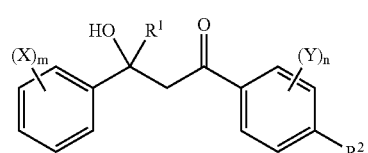

(1)

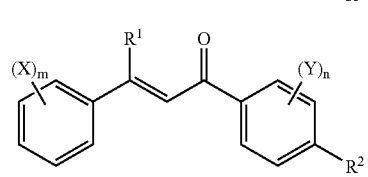

(2)

(where, X represents halogen atom, cyano group or the like, Y represents halogen atom, cyano group or the like, $R^1$ represents $C_1$-$C_6$ haloalkyl group or $C_3$-$C_8$ halocycloalkyl group, $R^2$ represents methyl group, halogen atom, cyano group or the like, m represents an integer of 1 to 5, and n represents an integer of 1 to 4).

5 Claims, No Drawings

OTHER PUBLICATIONS

Makoto Yasuda et al.; "NMR Studies of Five-Coordinate Tin Enolate: An Efficient Reagent for Halo Selective Reaction toward α-Halo Ketone or α-Halo Imine;" Journal of Organic Chemistry; 1994; vol. 59; pp. 4386-4392.

Makoto Yasuda et al.; "Cross-Coupling Reaction of α-Chloroketones and Organotin Enolates Catalyzed by Zinc Halides for Synthesis of γ-Diketones;" Journal of the American Chemical Society; 2002; vol. 124; pp. 7440-7447.

Makoto Yasuda et al.; "Facile Control of Regioselectivity in the Reaction of Tin Enolates with α-Halogeno Carbonyls by Additives;" Journal of the Chemical Society, Perkin Trans. 1; 1993; pp. 859-865.

V. Ya. Sosnovskikh et al.; "Ketone-Ketone Condensation with the Participation of Polyhaloalkyl Phenyl Ketones;" Zhumal Organicheskoi Khimii; vol. 28; No. 3; Mar. 1992; pp. 518-526.

Giuseppe Resnati et al.; "N-Fluorobis[(trifluoromethyl)sulfonyl]imide: An Efficient Reagent for the α-Fluorination of Functionalized Carbonyl Compounds;" Journal of Organic Chemistry; vol. 56; 1991; pp. 4925-4929.

Calvin L. Stevens et al.; "The Halodiphenacyls;" Journal of Organic Chemistry; vol. 19; 1954; pp. 522-532.

Votodimir Kovtunenko et al.; "Synthesis of Fused Imidazoles Based on γ-Bromodypnone;" Synthetic Communications; vol. 34; No. 19; 2004; pp. 3609-3613.

In Howa Jeong et al.; "New approaches to β-trifluoromethylated enone derivatives;" Journal of Fluorine Chemistry; vol. 125; 2004; pp. 1629-1638.

Yanchang Shen et al.; "A Novel Synthesis of Perfluoroalkylated α,β-Unsaturated Carbonyl Compounds;" Tetrahedron Letters; vol. 31; No. 41; 1990; pp. 5925-5926.

Yoo Tanabe et al.; "Direct, practical, and powerful crossed aldol additions between ketones and ketones or aldehydes utilizing environmentally benign TiCl$_4$-Bu$_3$N reagent;" Tetrahedron; vol. 58; 2002; pp. 8269-8280.

Alexander V. Kel'In et al.; "A New Simple Synthesis of Aryl-Substituted 1,4-Diketones;" Synthesis; 1996; pp. 330-332.

Adam Gillmore et al.; "A route to the structure proposed for puetuberosanol and approaches to the natural products marshrin and phebalosin;" Tetrahedron; vol. 59; 2003; pp. 4363-4375.

David A. Oare et al.; "Stereochemistry of the Michael Addition of N,N-Disubstituted Amide and Thioamide Enolates to α,β-Unsaturated Ketones;" Journal of Organic Chemistry; vol. 55; 1990; pp. 132-157.

Koichi Narasaka; "3,3-Dimethyl-1,5-Diphenylpentane-1,5-Dione;" Organic Syntheses; vol. 65; 1987; pp. 12.

Teruaki Mukaiyama et al.; "New Cross-Aldol Reactions. Reactions of Silyl Enol Ethers with Carbonyl Compounds Activated by Titanium Tetrachloride;" Journal of the American Chemical Society; vol. 96; 1974; pp. 7503-7509.

Makoto Yasuda et al.; "Catalytic Effect of Five-Coordinate Organotin Bromide or Tetraphenylstibonium Bromide on the Chemo- and Stereoselective Addition of Tin Enolate to α-Halo Ketone;" Bull. Chemical Society of Japan; vol. 68; 1995; pp. 1180-1186.

Herbert O. House et al.; "The Chemistry of Carbanions. XVIII. Preparation of Trimethylsilyl Enol Ethers;" The Journal of Organic Chemistry; vol. 34; 1969; pp. 2324-2336.

Sharada S. Labadie et al.; "Stereoselective Aldol Condensations of Organotin Reagents with Aldehydes;" Tetrahedron; vol. 40; No. 12; 1984; pp. 2329-2336.

R. K. Bansal et al.; "Synthesis and Spectral Studies of some New Fluorinated Phosphonium Salts and Ylides;" Journal of the Indian Chemical Society; vol. 65; Feb. 1988; pp. 134-136.

Bruce C. Hamper; "Direct Synthesis of β-Keto Methylenetriphenylphosphoranes from Readily Available Phosphonium Salts;" Journal of Organic Chemistry; vol. 53; 1988; pp. 5558-5562.

Yanchang Shen et al.; "Stereoselective synthesis of trifluoromethylated α-chloro-α,β-unsaturated esters and nitriles;" Journal of the Chemical Society, Perkin Trans. 1; 1996; pp. 2531-2533.

A. Schoenberg et al.; "Palladium-Catalyzed Carboalkoxylation of Aryl, Benzyl, and Vinylic Halides;" Journal of Organic Chemistry; vol. 39; No. 23; 1974; pp. 3318-3326.

Yasuhiro Uozumi et al.; "Green Catalysis: Hydroxycarbonylation of Aryl Halides in Water Catalyzed by an Amphiphilic Resin-Supported Phosphine-Palladium Complex;" Journal of Organic Chemistry; vol. 64; 1999; pp. 6921-6923.

Karl Steinbeck; "1-Brommethyl-2,2-dichlorcyclopropan als Alkylierungsreagenz;" Justus Liebigs Ann. Chem.; 1979; pp. 920-922.

Takashi Keumi et al.; "A Convenient Trifluoroacetylation of Arenes with 2-(Trifluoroacetoxy) pyridine;" Chemistry Letters; 1990; pp. 783-786.

Franklin F. Owings et al.; "An Enantioselective Synthesis of SK&F 93505, a Key Intermediate for Preparing Cardiotonic Agents;" Journal of Organic Chemistry; vol. 56; 1991; pp. 1963-1966.

Thomas F. McGrath et al; "The Synthesis of Certain Ketones and Carbinols Containing Perfluoroalkyl Groups;" Journal of the American Chemical Society; vol. 77; 1955; pp. 3656-3658.

William S. Dimenna; "A Convenient Preparation of Aryltrifluoromethylketones;" Tetrahedron Letters; vol. 21; 1980; pp. 2129-2132.

Francis A.J. Kerdesky et al.; "A Facile Synthesis of Aryl Trifluoromethyl Ketones;" Tetrahedron Letters; vol. 32; No. 18; 1991; pp. 2003-2004.

Nalini V. Shah et al.; "Synthesis of a Novel Carbapenem-Potassium (5R,6R)-1,1-Difluoro-2-Phenyl-6-(1R-Hydroxyethyl)-Carbapen-2-Em-3-Carboxylate. The Use of a New N-Protecting Group in β-Lactam Synthesis;" Heterocycles; vol. 25; 1987; pp. 221-227.

Donald A. Shaw et al; "An Efficient Synthesis of 3-Hydroxy-3-Trifluoromethyl Phthalide;" Synthetic Communications; vol. 15; No. 14; 1985; pp. 1291-1297.

Tomoya Kitazume et al; "Preparation of Optically Pure p-[(1-Hydroxy-2,2,2-Trifluoro)Ethyl]Benzoic Acid;" Synthetic Communications; vol. 20; No. 10; 1990; pp. 1469-1472.

Rajendra P. Singh et al.; "Cesium Fluoride Catalyzed Trifluoromethylation of Esters, Aldyhydes, and Ketones with (Trifluoromethyl)trimethylsilane;" Journal of Organic Chemistry; vol. 64; 1999; pp. 2873-2876.

Ramesh Krishnamurti et al.; "Preparation of Trifluoromethyl and Other Perfluoroalkyl Compounds with (Perfluoroalkyl)trimethylsilanes;" Journal of Organic Chemistry; vol. 56; 1991; pp. 984-989.

Timothy B. Patrick et al.; "Fluorodesulfurization of Aliphatic Orthothioesters;" Heteroatom Chemistry; vol. 10; No. 1; 1999; pp. 31-34.

* cited by examiner

1-3-BIS(SUBSTITUTED PHENYL)-3-HYDROXYPROPAN-1-ONE OR 2-PROPEN-1-ONE COMPOUND, AND SALT THEREOF

TECHNICAL FIELD

The present invention relates to a 1,3-bis(substituted phenyl)-3-substituent-3-hydroxypropan-1-one compound or salt thereof and a 1,3-bis(substituted phenyl)-3-substituent-2-propen-1-one compound or salt thereof, which are novel process intermediates useful as an agricultural chemical but have never been described in a document. The compounds or salts thereof are especially useful as process intermediates of a noxious organism control agent described in WO 05/085216 pamphlet.

BACKGROUND ART

Previously, a 3-bromoalkyl-substituted compound (see Non-patent Documents 1 to 3, for example), a 3-chloroalkyl-substituted compound (see Non-patent Documents 4 and 5, for example), a 3-fluoroalkyl-substituted compound (see Non-patent Documents 6 and 7, for example), and the like have been known as a 1,3-bis(substituted phenyl)-3-substituent-3-hydroxypropan-1-one compound, and 3-hydroxy-1-(4-methylphenyl)-3-phenyl-4,4,4-trifluorobutan-1-one is distributed by ChemBridge Corporation.

A 3-halo(other than fluorine atom)alkyl-substituted compound (see Non-patent Documents 8 and 9, for example) and the like are known as a 1,3-bis(substituted phenyl)-3-substituent-2-propen-1-one compound. A process intermediate of an agricultural chemical 4-(3-(4-chlorophenyl)-3-oxo-1-(trifluoromethyl)-1-propenyl)-2-methylphenylcarbamate tertiary-butyl ester (see Patent Document 1) is known as a 3-fluoroalkyl-substituted compound, and other 3-fluoroalkyl-substituted compounds (see Non-patent Documents 10 to 12, for example) are known. Compounds having benzyloxy group on a substituted phenyl are described in Patent Documents 2 and 3 as a 1,3-bis(substituted phenyl)-3-substituent-2-propen-1-one compound described as an agricultural chemical.

However, there is no description in the documents regarding a 1,3-bis(substituted phenyl)-3-substituent-3-hydroxypropan-1-one compound and a 1,3-bis(substituted phenyl)-3-substituent-2-propen-1-one compound, both of which can be used as a process intermediate derivable into a compound described in Patent Document 4, of these compounds described in the documents.

[Patent Document 1]
    WO 04/018410 pamphlet

[Patent Document 2]
    Japanese Patent Application Publication No. JP-A-11-236363

[Patent Document 3]
    EP 811608

[Patent Document 4]
    WO 05/085216 pamphlet

[Non-Patent Document 1]
    J. Am. Chem. Soc., vol. 57, p. 217 (1935)

[Non-Patent Document 2]
    Synthesis, p. 1259 (2000)

[Non-Patent Document 3]
    J. Org. Chem., vol. 59, p. 4386 (1994)

[Non-Patent Document 4]
    J. Am. Chem. Soc., vol. 124, p. 7440 (2002)

[Non-Patent Document 5]
    J. Chem. Soc., Perkin Trans. 1, p. 859 (1993)

[Non-Patent Document 6]
    Zhurnal Organicheskoi Khimii, vol. 28, p. 518 (1992)

[Non-Patent Document 7]
    J. Org. Chem., vol. 56, p. 4925 (1991)

[Non-Patent Document 8]
    J. Org. Chem., vol. 19, p. 522 (1954)

[Non-Patent Document 9]
    Synth. Commun., vol. 34, p. 3609 (2004)

[Non-Patent Document 10]
    J. Fluorine Chem., vol. 125, p. 1629 (2004)

[Non-Patent Document 11]
    Heteroatom Chem., vol. 10, p. 31 (1999)

[Non-Patent Document 12]
    Tetrahedron Lett., vol. 31, p. 5925 (1990)

DISCLOSURE OF THE INVENTION

Problems to be Solved by the Invention

It is an object of the present invention to provide a novel and useful agrochemical process intermediate a 1,3-bis(substituted phenyl)-3-substituent-3-hydroxypropan-1-one compound or salt thereof and a 1,3-bis(substituted phenyl)-3-substituent-2-propen-1-one compound or salt thereof.

Means for Solving the Problem

The inventors of the present invention have found, after intensive study to develop novel compounds useful as agrochemical process intermediates, a 1,3-bis(substituted phenyl)-3-substituent-3-hydroxypropan-1-one compound or salt thereof represented by the general formula (1) and a 1,3-bis(substituted phenyl)-3-substituent-2-propen-1-one compound or salt thereof represented by the general formula (2) and have completed the invention.

Namely, the present invention relates to the following (1) to (6).

(1) A 1,3-bis(substituted phenyl)-3-substituent-3-hydroxypropan-1-one compound or salt thereof represented by general formula (1):

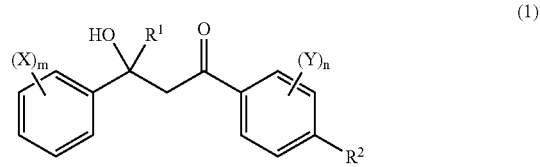

(where, X represents halogen atom, cyano group, nitro group, —SF$_5$, C$_1$-C$_6$ alkyl group, C$_1$-C$_6$ haloalkyl group, hydroxy (C$_1$-C$_6$)haloalkyl group, C$_1$-C$_6$ alkoxy(C$_1$-C$_6$)haloalkyl group, C$_1$-C$_6$ haloalkoxy(C$_1$-C$_6$)haloalkyl group, C$_3$-C$_8$ halocycloalkyl group, —OR$^3$, —OSO$_2$R$^3$, or —S(O)$_r$R$^3$ and, when m represents 2 or higher integer, each X can be identical with or different from each other;

Y represents halogen atom, cyano group, nitro group, $C_1$-$C_4$ alkyl group, $C_1$-$C_4$ haloalkyl group, $C_1$-$C_4$ alkoxy group, $C_1$-$C_4$ haloalkoxy group, $C_1$-$C_6$ alkylthio group, $C_1$-$C_6$ haloalkylthio group, $C_1$-$C_6$ alkylsulfonyl group, $C_1$-$C_6$ haloalkylsulfonyl group, —$NH_2$ or —$N(R^5)R^4$, and when n represents 2 or higher integer, each Y can be identical with or different from each other;

$R^1$ represents $C_1$-$C_6$ haloalkyl group or $C_3$-$C_8$ halocycloalkyl group;

$R^2$ represents methyl group, halogen atom, cyano group, nitro group, —$NH_2$, —$N(R^5)R^4$, —OH, —$OR^3$, benzyloxy group, —$OSO_2R^3$, phenylsulfonyloxy group, phenylsulfonyloxy group substituted by $(Z)_{p1}$, —C(O)OH, —C(O)$OR^3$, —C(O)$NH_2$, —C(O)N($R^b$)$R^a$, or —C(S)N($R^b$)$R^a$;

$R^3$ represents $C_1$-$C_6$ alkyl group, $C_1$-$C_4$ alkoxy($C_1$-$C_4$) alkyl group, $C_1$-$C_6$ haloalkyl group, or $C_1$-$C_3$ haloalkoxy($C_1$-$C_3$)haloalkyl group;

$R^4$ represents $C_1$-$C_6$ alkyl group, —CHO, $C_1$-$C_6$ alkylcarbonyl group, $C_1$-$C_6$ haloalkylcarbonyl group, $C_1$-$C_6$ alkoxycarbonyl group, $C_1$-$C_6$ alkylthiocarbonyl group, $C_1$-$C_6$ alkoxythiocarbonyl group, $C_1$-$C_6$ alkyldithiocarbonyl group, $C_1$-$C_6$ alkylsulfonyl group, or $C_1$-$C_6$ haloalkylsulfonyl group;

$R^5$ represents hydrogen atom or $C_1$-$C_6$ alkyl group;

$R^a$ represents $C_1$-$C_6$ alkyl group, ($C_1$-$C_6$) alkyl group substituted arbitrarily by $R^6$, $C_3$-$C_6$ cycloalkyl group, $C_3$-$C_6$ alkenyl group, $C_3$-$C_6$ haloalkenyl group, $C_3$-$C_6$ alkynyl group, —N($R^9$)$R^8$, —C(O)$OR^7$, —C(O)$NH_2$, —C(O)$NHR^7$, —C($R^{15}$)=$NOR^{14}$, phenyl group, phenyl group substituted by $(Z)_{p1}$, D-5, D-7, D-10, D-11, D-12, D-14, D-15, D-18, D-31, D-32, D-38, D-39, D-41, D-42, D-44, E-1, E-2, E-3, E-4, or E-7;

$R^b$ represents hydrogen atom, $C_1$-$C_6$ alkyl group, $C_1$-$C_4$ alkoxy($C_1$-$C_4$)alkyl group, cyano($C_1$-$C_6$)alkyl group, $C_3$-$C_6$ alkynyl group, —C(O)$R^7$, or —C(O)$OR^7$;

$R^6$ represents halogen atom, cyano group, $C_3$-$C_6$ cycloalkyl group, $C_3$-$C_6$ halocycloalkyl group, $C_1$-$C_6$ alkoxy group, $C_1$-$C_6$ haloalkoxy group, $C_1$-$C_6$ alkylthio group, $C_1$-$C_6$ haloalkylthio group, $C_1$-$C_6$ alkylsulfinyl group, $C_1$-$C_6$ haloalkylsulfinyl group, $C_1$-$C_6$ alkylsulfonyl group, $C_1$-$C_6$ haloalkylsulfonyl group, —C(O)$R^{12}$, —C(O)$OR^{12}$, —C(O)$NH_2$, —C(O)N($R^{13}$)$R^{12}$, —C(S)$NH_2$, —C(S)N($R^{13}$)$R^{12}$, —C($R^{15}$)=NOH, —C($R^{15}$)=$NOR^{14}$, phenyl group, phenyl group substituted by $(Z)_{p1}$, D-1 to D-46, or E-1 to E-8;

the D-1 to D-46 represent respective aromatic heterocycles as shown in the following structural formulae:

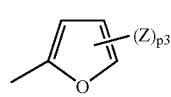

D-1

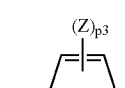

D-2

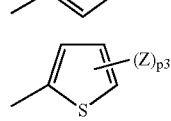

D-3

-continued

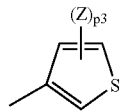

D-4

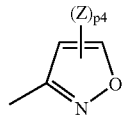

D-5

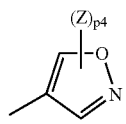

D-6

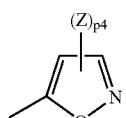

D-7

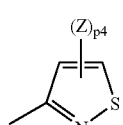

D-8

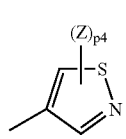

D-9

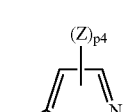

D-10

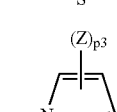

D-11

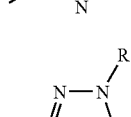

D-12

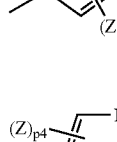

D-13

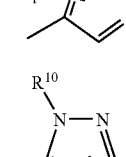

D-14

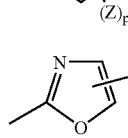

D-15

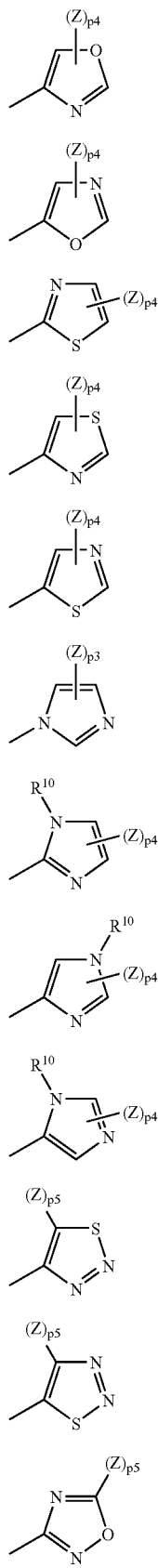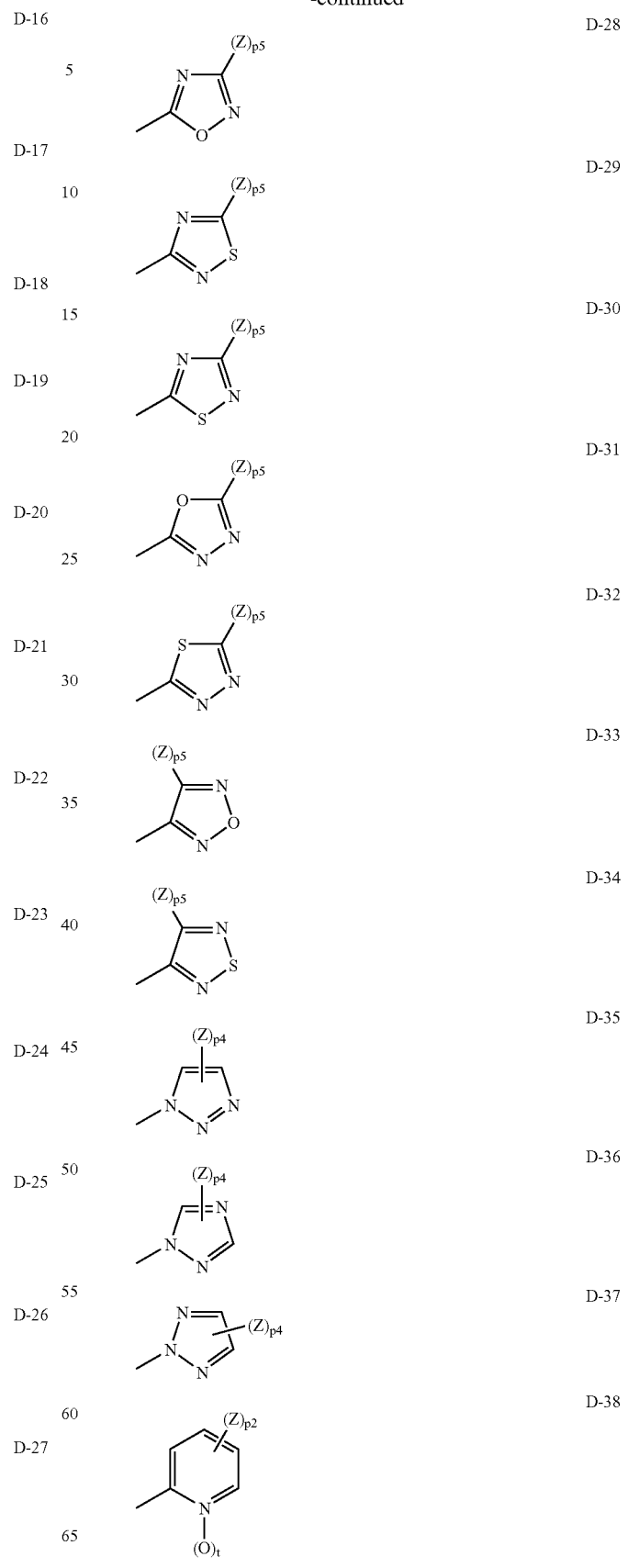

-continued

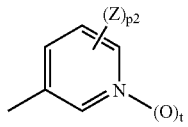
D-39

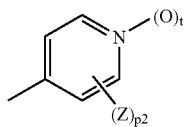
D-40

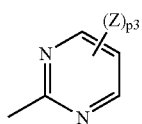
D-41

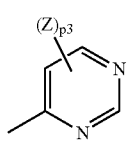
D-42

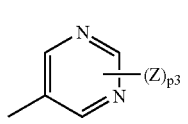
D-43

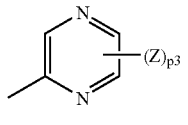
D-44

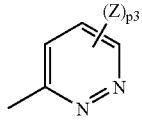
D-45

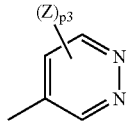
D-46

Z represents halogen atom, cyano group, nitro group, $C_1$-$C_6$ alkyl group, $C_1$-$C_6$ haloalkyl group, $C_1$-$C_6$ alkoxy group, $C_1$-$C_6$ haloalkoxy group, $C_1$-$C_6$ alkylsulfonyl group, $C_1$-$C_6$ haloalkylsulfonyl group, $C_1$-$C_6$ alkoxycarbonyl group, —C(O)NH$_2$, $C_1$-$C_6$ alkylaminocarbonyl group, di($C_1$-$C_6$ alkyl)aminocarbonyl group, —C(S)NH$_2$, —S(O)$_2$NH$_2$, $C_1$-$C_6$ alkylaminosulfonyl group or di($C_1$-$C_6$ alkyl)aminosulfonyl group, and when p1, p2, p3, or p4 represents 2 or higher integer, each Z can be identical with or different from each other;

E-1 to E-8 represent respective saturated heterocycles as shown in the following structural formulae:

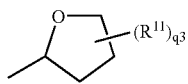
E-1

-continued

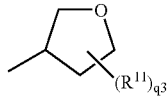
E-2

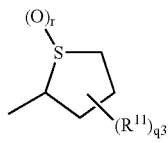
E-3

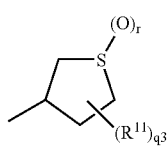
E-4

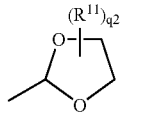
E-5

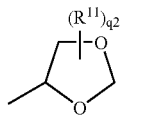
E-6

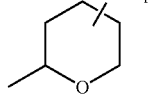
E-7

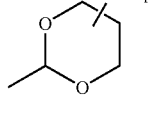
E-8

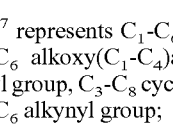

$R^7$ represents $C_1$-$C_6$ alkyl group, $C_1$-$C_6$ haloalkyl group, $C_1$-$C_6$ alkoxy($C_1$-$C_4$)alkyl group, $C_1$-$C_6$ alkylthio($C_1$-$C_4$) alkyl group, $C_3$-$C_8$ cycloalkyl group, $C_3$-$C_6$ alkenyl group, or $C_3$-$C_6$ alkynyl group;

$R^8$ represents $C_1$-$C_6$ haloalkyl group, —C(O)$R^{12}$, —C(O)OR$^{12}$, phenyl group, phenyl group substituted by (Z)$_{p1}$, D-3, D-4, D-18, D-38, D-41, D-42, D-44, or D-45;

$R^9$ represents hydrogen atom, $C_1$-$C_6$ alkyl group, or $C_3$-$C_6$ alkynyl group;

$R^{10}$ represents $C_1$-$C_6$ alkyl group, phenyl group, or phenyl group substituted by (Z)$_{p1}$;

$R^{11}$ represents $C_1$-$C_4$ alkyl group, when q1, q2, q3, or q4 represents 2 or higher integer, each $R^{11}$ can be identical with or different from each other, and two $R^{11}$s substituting on the same carbon atom indicate that the two $R^{11}$s can form an oxo ring together;

$R^{12}$ represents $C_1$-$C_6$ alkyl group, $C_1$-$C_6$ haloalkyl group, $C_3$-$C_6$ cycloalkyl($C_1$-$C_4$)alkyl group, $C_3$-$C_6$ cycloalkyl group, $C_3$-$C_6$ alkenyl group, or $C_3$-$C_6$ alkynyl group;

$R^{13}$ represents hydrogen atom or $C_1$-$C_6$ alkyl group;

$R^{14}$ represents $C_1$-$C_6$ alkyl group or $C_1$-$C_6$ haloalkyl group;

$R^{15}$ represents hydrogen atom or $C_1$-$C_6$ alkyl group;

m represents an integer of 1 to 5;

n represents an integer of 0 to 4;

p1 represents an integer of 1 to 5;

p2 represents an integer of 0 to 4;

p3 represents an integer of 0 to 3;
p4 represents an integer of 0 to 2;
p5 represents an integer of 0 or 1;
q2 represents an integer of 0 to 5;
q3 represents an integer of 0 to 7;
q4 represents an integer of 0 to 9;
r represents an integer of 0 to 2; and
t represents an integer of 0 or 1).

(2) The 1,3-bis(substituted phenyl)-3-substituent-3-hydroxypropan-1-one compound or salt thereof described in the above (1) which is represented by the formula, where X represents halogen atom or $C_1$-$C_4$ haloalkyl group, and when m represents 2 or 3, each X can be identical with or different from each other;

Y represents halogen atom, nitro group, $C_1$-$C_4$ alkyl group, or $C_1$-$C_4$ haloalkyl group;

$R^1$ represents $C_1$-$C_4$ haloalkyl group;

m represents an integer of 1 to 3; and n represents 0 or 1.

(3) The 1,3-bis(substituted phenyl)-3-substituent-3-hydroxypropan-1-one compound or salt thereof described in the above (2) which is represented by the formula, where $R^2$ represents halogen atom, cyano group, nitro group, —$NH_2$, —$NHR^4$, —OH, —$OR^3$, benzyloxy group, —$OSO_2R^3$, phenylsulfonyloxy group, paratoluenesulfonyloxy group, —C(O)OH, —C(O)$OR^3$, —C(O)$NH_2$, or —C(O)N($R^b$)$R^a$;

$R^3$ represents $C_1$-$C_4$ alkyl group or $C_1$-$C_4$ haloalkyl group;

$R^4$ represents $C_1$-$C_4$ alkyl group, —CHO, $C_1$-$C_4$ alkylcarbonyl group, or $C_1$-$C_4$ alkoxycarbonyl group;

$R^a$ represents $C_1$-$C_4$ alkyl group, ($C_1$-$C_4$) alkyl group substituted arbitrarily by $R^6$, —N($R^9$)$R^8$, —C(O)$OR^7$, —C(O)$NH_2$, —C(O)$NHR^7$, —C($R^{15}$)=$NOR^{14}$, phenyl group, phenyl group substituted by (Z)$_{p1}$, D-5, D-7, D-10, D-11, D-12, D-14, D-15, D-18, D-31, D-32, D-38, D-39, D-41, D-42, D-44, E-1, or E-7;

$R^b$ represents hydrogen atom, $C_1$-$C_6$ alkyl group, $C_1$-$C_4$ alkoxy($C_1$-$C_4$)alkyl group, cyano($C_1$-$C_4$)alkyl group, $C_3$-$C_6$ alkynyl group, —C(O)$R^7$, or —C(O)$OR^7$;

$R^6$ represents halogen atom, cyano group, $C_3$-$C_6$ cycloalkyl group, $C_1$-$C_4$ alkoxy, $C_1$-$C_4$ haloalkoxy group, $C_1$-$C_4$ alkylthio group, $C_1$-$C_4$ haloalkylthio group, $C_1$-$C_4$ alkylsulfonyl group, $C_1$-$C_4$ haloalkylsulfonyl group, —C(O)N($R^{13}$)$R^{12}$, —C($R^{15}$)=NOH, —C($R^{15}$)=$NOR^{14}$, phenyl group, phenyl group substituted by (Z)$_{p1}$, D-11 to D-14, D-18, D-19, D-25, D-26, D-31, D-32, D-36, D-38, D-41, D-44, D-45, E-1, E-2, or E-5;

Z represents halogen atom, cyano group, nitro group, $C_1$-$C_4$ alkyl group, $C_1$-$C_4$ haloalkyl group, $C_1$-$C_4$ alkoxy group, $C_1$-$C_4$ haloalkoxy group, $C_1$-$C_4$ alkylsulfonyl group, or $C_1$-$C_4$ haloalkylsulfonyl group, and when p1, p2, p3, or p4 represents 2 or higher integer, each Z can be identical with or different from each other;

$R^7$ represents $C_1$-$C_6$ alkyl group, $C_1$-$C_6$ haloalkyl group, $C_1$-$C_6$ alkoxy($C_1$-$C_4$)alkyl group, $C_1$-$C_6$ alkylthio($C_1$-$C_4$) alkyl group, $C_3$-$C_8$ cycloalkyl group, $C_3$-$C_6$ alkenyl group, or $C_3$-$C_6$ alkynyl group;

$R^8$ represents $C_1$-$C_4$ haloalkyl group, —C(O)$R^{12}$, —C(O)$OR^{12}$, phenyl group, phenyl group substituted by (Z)$_{p1}$, D-3, D-4, D-18, D-38, D-41, D-42, D-44, or D-45;

$R^9$ represents hydrogen atom or $C_1$-$C_6$ alkyl group;

$R^{10}$ represents $C_1$-$C_4$ alkyl group;

$R^{11}$ represents $C_1$-$C_4$ alkyl group, when q1, q2, q3, or q4 represents 2 or higher integer, each $R^{11}$ can be identical with or different from each other, and two $R^{11}$s substituting on the same carbon atom indicate that the two $R^{11}$s can form an oxo ring together;

$R^{12}$ represents $C_1$-$C_4$ alkyl group, $C_1$-$C_4$ haloalkyl group, $C_3$-$C_6$ cycloalkyl($C_1$-$C_4$) alkyl group, $C_3$-$C_6$ cycloalkyl group, $C_3$-$C_6$ alkenyl group, or $C_3$-$C_6$ alkynyl group;

$R^{13}$ represents hydrogen atom or $C_1$-$C_4$ alkyl group;

$R^{14}$ represents $C_1$-$C_4$ alkyl group or $C_1$-$C_4$ haloalkyl group; and $R^{15}$ represents hydrogen atom or $C_1$-$C_4$ alkyl group.

(4) A 1,3-bis(substituted phenyl)-3-substituent-2-propen-1-one compound or salt thereof represented by general formula (2):

(2)

(where, X represents halogen atom, cyano group, nitro group, —$SF_5$, $C_1$-$C_6$ alkyl group, $C_1$-$C_6$ haloalkyl group, hydroxy ($C_1$-$C_6$)haloalkyl group, $C_1$-$C_6$ alkoxy($C_1$-$C_6$)haloalkyl group, $C_1$-$C_6$ haloalkoxy($C_1$-$C_6$)haloalkyl group, $C_3$-$C_8$ halocycloalkyl group, —$OR^3$, —$OSO_2R^3$, or —S(O)$_rR^3$, and when m represents 2 or higher integer, each X can be identical with or different from each other;

Y represents halogen atom, cyano group, nitro group, $C_1$-$C_4$ alkyl group, $C_1$-$C_4$ haloalkyl group, $C_1$-$C_4$ alkoxy group, $C_1$-$C_4$ haloalkoxy group, $C_1$-$C_6$ alkylthio group, $C_1$-$C_6$ haloalkylthio group, $C_1$-$C_6$ alkylsulfonyl group, $C_1$-$C_6$ haloalkylsulfonyl group, —$NH_2$ or —N($R^5$)$R^4$, and when n represents 2 or higher integer, each Y can be identical with or different from each other;

$R^1$ represents $C_1$-$C_6$ haloalkyl group or $C_3$-$C_8$ halocycloalkyl group;

$R^2$ represents methyl group, halogen atom, cyano group, nitro group, —$NH_2$, —N($R^5$)$R^4$, —OH, —$OR^3$, benzyloxy group, —$OSO_2R^3$, phenylsulfonyloxy group, phenylsulfonyloxy group substituted by (Z)$_{p1}$, —C(O)OH, —C(O)$OR^3$, —C(O)$NH_2$, —C(O)N($R^b$)$R^a$ or —C(S)N($R^b$)$R^a$;

$R^3$ represents $C_1$-$C_6$ alkyl group, $C_1$-$C_4$ alkoxy($C_1$-$C_4$) alkyl group, $C_1$-$C_6$ haloalkyl group or $C_1$-$C_3$ haloalkoxy($C_1$-$C_3$)haloalkyl group;

$R^4$ represents $C_1$-$C_6$ alkyl group, —CHO, $C_1$-$C_6$ alkylcarbonyl group, $C_1$-$C_6$ haloalkylcarbonyl group, $C_1$-$C_6$ alkoxycarbonyl group, $C_1$-$C_6$ alkylthiocarbonyl group, $C_1$-$C_6$ alkoxythiocarbonyl group, $C_1$-$C_6$ alkyldithiocarbonyl group, $C_1$-$C_6$ alkylsulfonyl group, or $C_1$-$C_6$ haloalkylsulfonyl group;

$R^5$ represents hydrogen atom or $C_1$-$C_6$ alkyl group;

$R^a$ represents $C_1$-$C_6$ alkyl group, ($C_1$-$C_6$) alkyl group substituted arbitrarily by $R^6$, $C_3$-$C_6$ cycloalkyl group, $C_3$-$C_6$ alkenyl group, $C_3$-$C_6$ haloalkenyl group, $C_3$-$C_6$ alkynyl group, —N($R^9$)$R^8$, —C(O)$OR^7$, —C(O)$NH_2$, —C(O)$NHR^7$, —C($R^{15}$)=$NOR^{14}$, phenyl group, phenyl group substituted by (Z)$_{p1}$, D-5, D-7, D-10, D-11, D-12, D-14, D-15, D-18, D-31, D-32, D-38, D-39, D-41, D-42, D-44, E-1, E-2, E-3, E-4, or E-7;

$R^b$ represents hydrogen atom, $C_1$-$C_6$ alkyl group, $C_1$-$C_4$ alkoxy($C_1$-$C_4$)alkyl group, cyano($C_1$-$C_6$)alkyl group, $C_3$-$C_6$ alkynyl group, —C(O)$R^7$, or —C(O)$OR^7$;

$R^6$ represents halogen atom, cyano group, $C_3$-$C_6$ cycloalkyl group, $C_3$-$C_6$ halocycloalkyl group, $C_1$-$C_6$ alkoxy group, $C_1$-$C_6$ haloalkoxy group, $C_1$-$C_6$ alkylthio group, $C_1$-$C_6$ haloalkylthio group, $C_1$-$C_6$ alkylsulfinyl group, $C_1$-$C_6$ haloalkylsulfinyl group, $C_1$-$C_6$ alkylsulfonyl group, $C_1$-$C_6$ haloalkylsulfonyl group, —C(O)R$^{12}$, —C(O)OR$^{12}$, —C(O)NH$_2$, —C(O)N(R$^{13}$)R$^{12}$, —C(S)NH$_2$, —C(S)N(R$^{13}$)R$^{12}$, —C(R$^{15}$)=NOH, —C(R$^{15}$)=NOR$^{14}$, phenyl group, phenyl group substituted by (Z)$_{p1}$, D-1 to D-46, or E-1 to E-8;
the D-1 to D-46 represent respective aromatic heterocycles as shown in the following structural formulae:
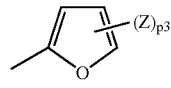
D-1
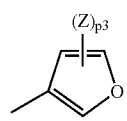
D-2
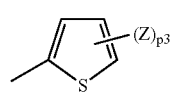
D-3
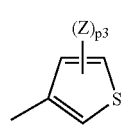
D-4
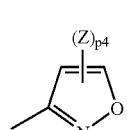
D-5
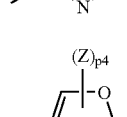
D-6
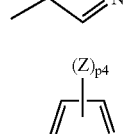
D-7
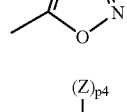
D-8
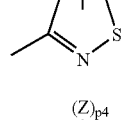
D-9
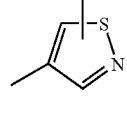
D-10
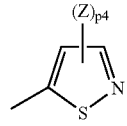
D-11
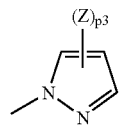
-continued
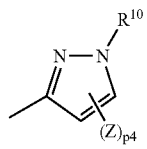
D-12
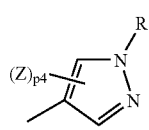
D-13
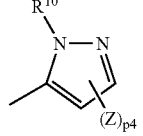
D-14
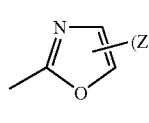
D-15
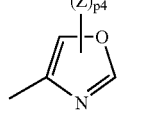
D-16
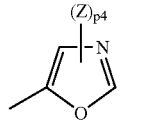
D-17
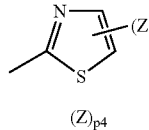
D-18
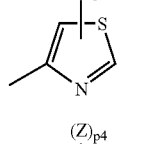
D-19
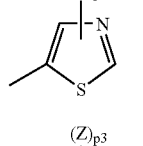
D-20
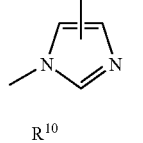
D-21
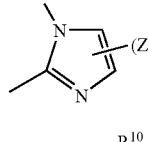
D-22
D-23

-continued
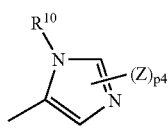 D-24
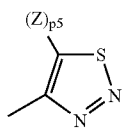 D-25
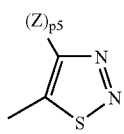 D-26
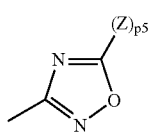 D-27
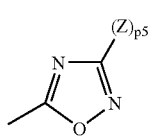 D-28
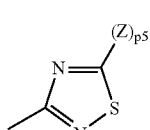 D-29
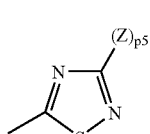 D-30
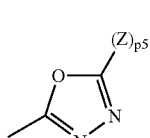 D-31
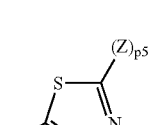 D-32
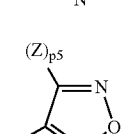 D-33
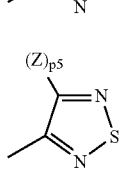 D-34
-continued
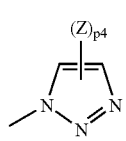 D-35
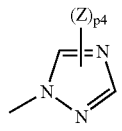 D-36
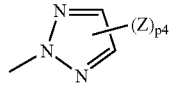 D-37
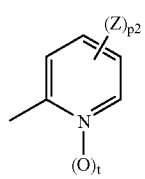 D-38
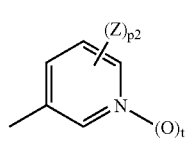 D-39
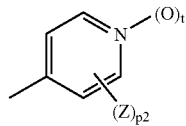 D-40
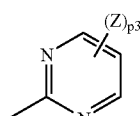 D-41
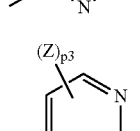 D-42
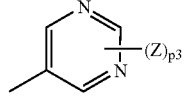 D-43
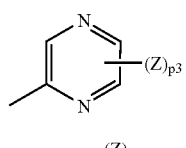 D-44
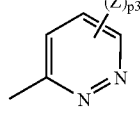 D-45
D-46

Z represents halogen atom, cyano group, nitro group, $C_1$-$C_6$ alkyl group, $C_1$-$C_6$ haloalkyl group, $C_1$-$C_6$ alkoxy group, $C_1$-$C_6$ haloalkoxy group, $C_1$-$C_6$ alkylsulfonyl group, $C_1$-$C_6$ haloalkylsulfonyl group, $C_1$-$C_6$ alkoxycarbonyl group, —C(O)NH$_2$, $C_1$-$C_6$ alkylaminocarbonyl group, di($C_1$-$C_6$ alkyl)aminocarbonyl group, —C(S)NH$_2$, —S(O)$_2$NH$_2$, $C_1$-$C_6$ alkylaminosulfonyl group or di($C_1$-$C_6$ alkyl)aminosulfonyl group, and when p1, p2, p3, or p4 represents 2 or higher integer, each Z can be identical with or different from each other;

the E-1 to E-8 represent respective saturated heterocycles as shown in the following structural formulae:

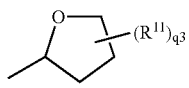
E-1

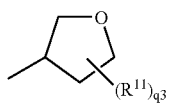
E-2

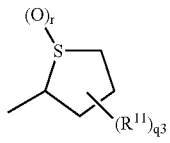
E-3

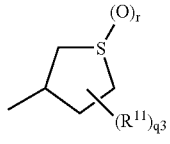
E-4

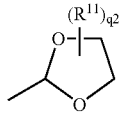
E-5

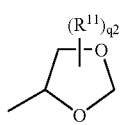
E-6

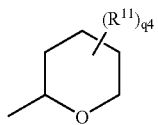
E-7

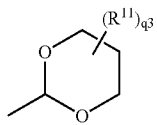
E-8

$R^7$ represents $C_1$-$C_6$ alkyl group, $C_1$-$C_6$ haloalkyl group, $C_1$-$C_6$ alkoxy($C_1$-$C_4$)alkyl group, $C_1$-$C_6$ alkylthio($C_1$-$C_4$)alkyl group, $C_3$-$C_8$ cycloalkyl group, $C_3$-$C_6$ alkenyl group, or $C_3$-$C_6$ alkynyl group;

$R^8$ represents $C_1$-$C_6$ haloalkyl group, —C(O)R$^{12}$, —C(O)OR$^{12}$, phenyl group, phenyl group substituted by (Z)$_{p1}$, D-3, D-4, D-18, D-38, D-41, D-42, D-44, or D-45;

$R^9$ represents hydrogen atom, $C_1$-$C_6$ alkyl group, or $C_3$-$C_6$ alkynyl group;

$R^{10}$ represents $C_1$-$C_6$ alkyl group, phenyl group, or phenyl group substituted by (Z)$_{p1}$;

$R^{11}$ represents $C_1$-$C_4$ alkyl group, when q1, q2, q3, or q4 represents 2 or higher integer, each $R^{11}$ can be identical with or different from each other, and two $R^{11}$'s substituting on the same carbon atom indicate that the two $R^{11}$'s can form an oxo ring together;

$R^{12}$ represents $C_1$-$C_6$ alkyl group, $C_1$-$C_6$ haloalkyl group, $C_3$-$C_6$ cycloalkyl($C_1$-$C_4$)alkyl group, $C_3$-$C_6$ cycloalkyl group, $C_3$-$C_6$ alkenyl group, or $C_3$-$C_6$ alkynyl group;

$R^{13}$ represents hydrogen atom or $C_1$-$C_6$ alkyl group;
$R^{14}$ represents $C_1$-$C_6$ alkyl group or $C_1$-$C_6$ haloalkyl group;
$R^{15}$ represents hydrogen atom or $C_1$-$C_6$ alkyl group;
m represents an integer of 1 to 5;
n represents an integer of 0 to 4;
p1 represents an integer of 1 to 5;
p2 represents an integer of 0 to 4;
p3 represents an integer of 0 to 3;
p4 represents an integer of 0 to 2;
p5 represents an integer of 0 or 1;
q2 represents an integer of 0 to 5;
q3 represents an integer of 0 to 7;
q4 represents an integer of 0 to 9;
r represents an integer of 0 to 2; and
t represents an integer of 0 or 1).

(5) The 1,3-bis(substituted phenyl)-3-substituent-2-propen-1-one compound or salt thereof described in the above (4) which is represented by the formula, where X represents halogen atom or $C_1$-$C_4$ haloalkyl group, and when m represents 2 or 3, each X can be identical with or different from each other;

Y represents halogen atom, nitro group, $C_1$-$C_4$ alkyl group, or $C_1$-$C_4$ haloalkyl group;

$R^1$ represents $C_1$-$C_4$ haloalkyl group;
m represents an integer of 1 to 3; and
n represents 0 or 1.

(6) The 1,3-bis(substituted phenyl)-3-substituent-2-propen-1-one compound or salt thereof described in the above (5) which is represented by the formula, where $R^2$ represents halogen atom, cyano group, nitro group, —NH$_2$, —NHR$^4$, —OH, —OR$^3$, benzyloxy group, —OSO$_2$R$^3$, phenylsulfonyloxy group, paratoluenesulfonyloxy group, —C(O)OH, —C(O)OR$^3$, —C(O)NH$_2$, or —C(O)N(R$^b$)R$^a$;

$R^3$ represents $C_1$-$C_4$ alkyl group or $C_1$-$C_4$ haloalkyl group;
$R^4$ represents $C_1$-$C_4$ alkyl group, —CHO, $C_1$-$C_4$ alkylcarbonyl group, or $C_1$-$C_4$ alkoxycarbonyl group;

$R^a$ represents $C_1$-$C_4$ alkyl group, ($C_1$-$C_4$) alkyl group substituted arbitrarily by $R^6$, —N(R$^9$)R$^8$, —C(O)OR$^7$, —C(O)NH$_2$, —C(O)NHR$^7$, —C(R$^{15}$)=NOR$^{14}$, phenyl group, phenyl group substituted by (Z)$_{p1}$, D-5, D-7, D-10, D-11, D-12, D-14, D-15, D-18, D-31, D-32, D-38, D-39, D-41, D-42, D-44, E-1, or E-7;

$R^b$ represents hydrogen atom, $C_1$-$C_6$ alkyl group, $C_1$-$C_4$ alkoxy($C_1$-$C_4$)alkyl group, cyano($C_1$-$C_4$)alkyl group, $C_3$-$C_6$ alkynyl group, —C(O)R$^7$, or —C(O)OR$^7$;

$R^6$ represents halogen atom, cyano group, $C_3$-$C_6$ cycloalkyl group, $C_1$-$C_4$ alkoxy group, $C_1$-$C_4$ haloalkoxy group, $C_1$-$C_4$ alkylthio group, $C_1$-$C_4$ haloalkylthio group, $C_1$-$C_4$ alkylsulfonyl group, $C_1$-$C_4$ haloalkylsulfonyl group, —C(O)N(R$^{13}$)R$^{12}$, —C(R$^{15}$)=NOH, —C(R$^{15}$)=NOR$^{14}$, phenyl group, phenyl group substituted by (Z)$_{p1}$, D-11 to D-14, D-18, D-19, D-25, D-26, D-31, D-32, D-36, D-38, D-41, D-44, D-45, E-1, E-2, or E-5;

Z represents halogen atom, cyano group, nitro group, $C_1$-$C_4$ alkyl group, $C_1$-$C_4$ haloalkyl group, $C_1$-$C_4$ alkoxy group, $C_1$-$C_4$ haloalkoxy group, $C_1$-$C_4$ alkylsulfonyl group, or $C_1$-$C_4$ haloalkylsulfonyl group, and when p1, p2, p3, or p4 represents 2 or higher integer, each Z can be identical with or different from each other;

$R^7$ represents $C_1$-$C_6$ alkyl group, $C_1$-$C_6$ haloalkyl group, $C_1$-$C_6$ alkoxy($C_1$-$C_4$)alkyl group, $C_1$-$C_6$ alkylthio($C_1$-$C_4$) alkyl group, $C_3$-$C_8$ cycloalkyl group, $C_3$-$C_6$ alkenyl group, or $C_3$-$C_6$ alkynyl group;

$R^8$ represents $C_1$-$C_4$ haloalkyl group, —C(O)$R^{12}$, —C(O)O$R^{12}$, phenyl group, phenyl group substituted by $(Z)_{p1}$, D-3, D-4, D-18, D-38, D-41, D-42, D-44, or D-45;

$R^9$ represents hydrogen atom or $C_1$-$C_6$ alkyl group;

$R^{10}$ represents $C_1$-$C_4$ alkyl group;

$R^{11}$ represents $C_1$-$C_4$ alkyl group, when q1, q2, q3, or q4 represents 2 or higher integer, each $R^{11}$ can be identical with or different from each other, and two $R^{11}$s substituting on the same carbon atom indicate that the two $R^{11}$s can form an oxo ring together;

$R^{12}$ represents $C_1$-$C_4$ alkyl group, $C_1$-$C_4$ haloalkyl group, $C_3$-$C_6$ cycloalkyl($C_1$-$C_4$)alkyl group, $C_3$-$C_6$ cycloalkyl group, $C_3$-$C_6$ alkenyl group, or $C_3$-$C_6$ alkynyl group;

$R^{13}$ represents hydrogen atom or $C_1$-$C_4$ alkyl group;

$R^{14}$ represents $C_1$-$C_4$ alkyl group or $C_1$-$C_4$ haloalkyl group;

$R^{15}$ represents hydrogen atom or $C_1$-$C_4$ alkyl group.

ADVANTAGEOUS EFFECTS OF THE INVENTION

The present invention can provide a novel process intermediate of an agricultural chemical, especially of a compound having excellent insecticidal and acaricidal activity against agricultural pest insects, spider mites, and internal or external parasites of mammals or birds described in WO 05/085216 pamphlet.

BEST MODES FOR CARRYING OUT THE INVENTION

The compound of the present invention represented by the general formula (1) includes E-and Z-geometrical isomers depending on the substituents, while the compound represented by the general formula (2) includes E-and Z-geometrical isomers. The present invention includes a mixture containing E-form, Z-form or E-and Z-forms at a given rate. Also, the compound of the present invention represented by the general formula (1) includes an optically active form due to the presence of 1 or 2 or more asymmetric carbon atom(s), while the compound represented by the general formula (2) includes the optically active form due to the presence of 1 or 2 or more asymmetric carbon atom(s) depending on the substituents. The present invention includes all optically active forms or racemic bodies.

The compound included in the present invention that can be formed into an acid addition salt according to a conventional procedure can be formed into, for example, a salt of hydrohalic acid such as hydrofluoric acid, hydrochloric acid, hydrobromic acid, and hydroiodic acid, a salt of inorganic acid such as nitric acid, sulfuric acid, phosphoric acid, chloric acid, and perchloric acid, a salt of sulfonic acid such as methanesulfonic acid, ethanesulfonic acid, trifluoromethanesulfonic acid, benzenesulfonic acid, and p-toluenesulfonic acid, a salt of carboxylic acid such as formic acid, acetic acid, propionic acid, trifluoroacetic acid, fumaric acid, acidum tartricum, oxalic acid, maleic acid, malic acid, succinic acid, benzoic acid, mandelic acid, ascorbic acid, lactic acid, gluconic acid, and citric acid, or a salt of amino acid such as glutamic acid and asparagines acid.

On the other hand, the compound included in the present invention that can be formed into a metallic salt according to a conventional procedure can be formed into, for example, a salt of alkaline metal such as lithium, sodium, and potassium, a salt of alkaline earth metal such as calcium, barium, and magnesium, or a salt of aluminum.

Then, specific examples of each substituent represented in this description are shown below. Here, n-denotes normal, i-denotes iso, s-denotes secondary, and t-denotes tertiary as well as Ph denotes phenyl.

Halogen atom in the compound of the present invention includes fluorine atom, chlorine atom, bromine atom, and iodine atom. Also, the notation "halo" in this description represents these halogen atoms.

The notation $C_a$-$C_b$ alkyl group in this description denotes a straight-chain or branched-chain hydrocarbon group with the number of carbon atom(s) of a to b including, for example, methyl group, ethyl group, n-propyl group, i-propyl group, n-butyl group, i-butyl group, s-butyl group, t-butyl group, n-pentyl group, 1-methylbutyl group, 2-methylbutyl group, 3-methylbutyl group, 1-ethylpropyl group, 1,1-dimethylpropyl group, 1,2-dimethylpropyl group, 2,2-dimethylpropyl group, n-hexyl group, 1-methylpentyl group, 2-methylpentyl group, 1,1-dimethylbutyl group, 1,3-dimethylbutyl group, heptyl group, octyl group, nonyl group, decyl group, undecyl group, and dodecyl group, as specific examples, which are selected within each specified range of the number of carbon atoms.

The notation $C_a$-$C_b$ haloalkyl group in this description denotes a straight-chain or branched-chain hydrocarbon group with the number of carbon atom(s) of a to b in which hydrogen atom bound to carbon atom is arbitrarily substituted by halogen atom. When the above-mentioned group is substituted by 2 or more halogen atoms, these halogen atoms can be identical with or different from each other. The hydrocarbon group includes, for example, fluoromethyl group, chloromethyl group, bromomethyl group, iodomethyl group, difluoromethyl group, chlorofluoromethyl group, dichloromethyl group, bromofluoromethyl group, trifluoromethyl group, chlorodifluoromethyl group, dichlorofluoromethyl group, trichloromethyl group, bromodifluoromethyl group, bromochlorofluoromethyl group, dibromofluoromethyl group, 2-fluoroethyl group, 2-chloroethyl group, 2-bromoethyl group, 2,2-difluoroethyl group, 2-chloro-2-fluoroethyl group, 2,2-dichloroethyl group, 2-bromo-2-fluoroethyl group, 2,2,2-trifluoroethyl group, 2-chloro-2,2-difluoroethyl group, 2,2-dichloro-2-fluoroethyl group, 2,2,2-trichloroethyl group, 2-bromo-2,2-difluoroethyl group, 2-bromo-2-chloro-2-fluoroethyl group, 2-bromo-2,2-dichloroethyl group, 1,1,2,2-tetrafluoroethyl group, pentafluoroethyl group, 1-chloro-1,2,2,2-tetrafluoroethyl group, 2-chloro-1,1,2,2-tetrafluoroethyl group, 1,2-dichloro-1,2,2-trifluoroethyl group, 2-bromo-1,1,2,2-tetrafluoroethyl group, 2-fluoropropyl group, 2-chloropropyl group, 2-bromopropyl group, 2-chloro-2-fluoropropyl group, 2,3-dichloropropyl group, 2-bromo-3-fluoropropyl group, 3-bromo-2-chloropropyl group, 2,3-dibromopropyl group, 3,3,3-trifluoropropyl group, 3-bromo-3,3-difluoropropyl group, 2,2,3,3-tetrafluoropropyl group, 2-chloro-3,3,3-trifluoropropyl group, 2,2,3,3,3-pentafluoropropyl group, 1,1,2,3,3,3-hexafluoropropyl group, heptafluoropropyl group, 2,3-dichloro-1,1,2,3,3-pentafluoropropyl group, 2-fluoro-1-methylethyl group, 2-chloro-1-methylethyl group, 2-bromo-1-methylethyl group, 2,2,2-trifluoro-1-(trifluoromethyl)ethyl group, 1,2,2,2-tetrafluoro-1-(trifluoromethyl)ethyl group, 2-fluorobutyl group, 2-chlorobutyl group, 2,2,3,3,4,4-hexafluorobutyl group, 2,2,3,4,4,4-hexafluorobutyl group, 2,2,3,3,4,4- hexafluorobutyl group, 2,2,3,3,4,4,4-heptafluorobutyl group, 1,1,2,2,3,3,4,4-octafluorobutyl group, nonafluorobutyl group, 4-chloro-1,1,2,2,3,3,4,4-octafluorobutyl group, 2-fluoro-2-methylpropyl group, 1,2,2,3,3,3-hexafluoro-1-(trifluoromethyl)propyl group, 2-chloro-1,1-dimethylethyl group, 2-bromo-1,1-dimethylethyl group, 5-chloro-2,2,3,4,4,5,5-heptafluoropentyl group, tridecafluorohexyl group, as specific examples, which are selected within each specified range of the number of carbon atoms.

The notation cyano($C_a$-$C_b$)alkyl group in this description denotes a straight-chain or branched-chain alkyl group with the number of carbon atom(s) of a to b in which hydrogen atom bound to carbon atom is arbitrarily substituted by cyano group including, for example, cyanomethyl group, 1-cyanoethyl group, 2-cyanoethyl group, 2-cyanopropyl group, 3-cyanopropyl group, and 2-cyanobutyl group, as specific examples, which are selected within each specified range of the number of carbon atoms.

The notation $C_a$-$C_b$ cycloalkyl group in this description denotes a cyclic hydrocarbon group with the number of carbon atom(s) of a to b which can be formed into 3-to 6-membered monocyclic or combined cyclic structure. Also, each cycle can be substituted arbitrarily by alkyl group within a specified range of the number of carbon atoms. The hydrocarbon group includes, for example, cyclopropyl group, 1-methylcyclopropyl group, 2-methylcyclopropyl group, 2,2-dimethylcyclopropyl group, 2,2,3,3-tetramethylcyclopropyl group, cyclobutyl group, cyclopentyl group, 2-methylcyclopentyl group, 3-methylcyclopentyl group, cyclohexyl group, 2-methylcyclohexyl group, 3-methylcyclohexyl group, 4-methylcyclohexyl group, and bicyclo(2.2.1)heptane-2-yl group, as specific examples, which are selected within each specified range of the number of carbon atoms.

The notation $C_a$-$C_b$ halocycloalkyl group in this description denotes a cyclic hydrocarbon group with the number of carbon atom(s) of a to b in which hydrogen atom bound to carbon atom is arbitrarily substituted by halogen atom and which can be formed into 3-to 6-membered monocyclic or combined cyclic structure. Also, each cycle can be substituted arbitrarily by alkyl group within a specified range of the number of carbon atoms. Substitution by halogen atom can occur at a cyclic part and/or side chain, and in the case of substitution by 2 or more halogen atoms, these halogen atoms can be identical with or different from each other. The hydrocarbon group includes, for example, 2,2-difluorocyclopropyl group, 2,2-dichlorocyclopropyl group, 2,2-dibromocyclopropyl group, 2,2-difluoro-1-methylcyclopropyl group, 2,2-dichloro-1-methylcyclopropyl group, 2,2-dibromo-1-methylcyclopropyl group, 2,2,3,3-tetrafluorocyclobutyl group, 2-(trifluoromethyl)cyclohexyl group, 3-(trifluoromethyl)cyclohexyl group, and 4-(trifluoromethyl)cyclohexyl group, as specific examples, which are selected within each specified range of the number of carbon atoms.

The notation $C_a$-$C_b$ alkenyl group in this description denotes a straight-chain or branched-chain and unsaturated hydrocarbon group with the number of carbon atom(s) of a to b and 1 or 2 or more double bond(s) in a molecule including, for example, vinyl group, 1-propenyl group, 2-propenyl group, 1-methylethenyl group, 2-butenyl group, 1-methyl-2-propenyl group, 2-methyl-2-propenyl group, 2-penthenyl group, 2-methyl-2-butenyl group, 3-methyl-2-butenyl group, 2-ethyl-2-propenyl group, 1,1-dimethyl-2-propenyl group, 2-hexenyl group, 2-methyl-2-penthenyl group, 2,4-dimethyl-2,6-heptadienyl group, and 3,7-dimethyl-2,6-octadienyl group, as specific examples, which are selected within each specified range of the number of carbon atoms.

The notation $C_a$-$C_b$ haloalkenyl group in this description denotes a straight-chain or branched-chain and unsaturated hydrocarbon group with the number of carbon atom(s) of a to b and 1 or 2 or more double bond(s) in a molecule in which hydrogen atom bound to carbon atom is arbitrarily substituted by halogen atom. Here, in the case of substitution by 2 or more halogen atoms, these halogen atoms can be identical with or different from each other. The hydrocarbon group includes, for example, 2,2-dichlorovinyl group, 2-fluoro-2-propenyl group, 2-chloro-2-propenyl group, 3-chloro-2-propenyl group, 2-bromo-2-propenyl group, 3-bromo-2-propenyl group, 3,3-difluoro-2-propenyl group, 2,3-dichloro-2-propenyl group, 3,3-dichloro-2-propenyl group, 2,3-dibromo-2-propenyl group, 2,3,3-trifluoro-2-propenyl group, 2,3,3-trichloro-2-propenyl group, 1-(trifluoromethyl)ethenyl group, 3-chloro-2-butenyl group, 3-bromo-2-butenyl group, 4,4-difluoro-3-butenyl group, 3,4,4-trifluoro-3-butenyl group, 3-chloro-4,4,4-trifluoro-2-butenyl group, and 3-bromo-2-methyl-2-propenyl group, as specific examples, which are selected within each specified range of the number of carbon atoms.

The notation $C_a$-$C_b$ alkynyl group in this description denotes a straight-chain or branched-chain and unsaturated hydrocarbon group with the number of carbon atom(s) of a to b and one or 2 or more triple bond(s) in a molecule, including, for example, ethynyl group, 1-propynyl group, 2-propynyl group, 2-butynyl group, 1-methyl-2-propynyl group, 2-pentynyl group, 1-methyl-2-butynyl group, 1,1-dimethyl-2-propynyl group, and 2-hexynyl group, as specific examples, which are selected within each specified range of the number of carbon atoms.

The notation $C_a$-$C_b$ alkoxy group in this description denotes alkyl-O— group with the meaning and the number of carbon atom(s) of a to b including, for example, methoxy group, ethoxy group, n-propyloxy group, i-propyloxy group, n-butyloxy group, i-butyloxy group, s-butyloxy group, t-butyloxy group, n-pentyloxy group, and n-hexyloxy group, as specific examples, which are selected within each specified range of the number of carbon atoms.

The notation $C_a$-$C_b$ haloalkoxy group in this description denotes haloalkyl-O— group with the meaning and the number of carbon atom(s) of a to b including, for example, difluoromethoxy group, trifluoromethoxy group, chlorodifluoromethoxy group, bromodifluoromethoxy group, 2-fluoroethoxy group, 2-chloroethoxy group, 2,2,2-trifluoroethoxy group, 1,1,2,2-tetrafluoroethoxy group, 2-chloro-1,1,2-trifluoroethoxy group, 2-bromo-1,1,2-trifluoroethoxy group, pentafluoroethoxy group, 2,2-dichloro-1,1,2-trifluoroethoxy group, 2,2,2-trichloro-1,1-difluoroethoxy group, 2-bromo-1,1,2,2-tetrafluoroethoxy group, 2,2,3,3-tetrafluoropropyloxy group, 1,1,2,3,3,3-hexafluoropropyloxy group, 2,2,2-trifluoro-1-(trifluoromethyl)ethoxy group, heptafluoropropyloxy group, and 2-bromo-1,1,2,3,3,3-hexafluoropropyloxy group, as specific examples, which are selected within each specified range of the number of carbon atoms.

The notation $C_a$-$C_b$ alkylthio group in this description denotes alkyl-S— group with the meaning and the number of carbon atom(s) of a to b including, for example, methylthio group, ethylthio group, n-propylthio group, i-propylthio group, n-butylthio group, i-butylthio group, s-butylthio group, t-butylthio group, n-pentylthio group, and n-hexylthio group, as specific examples, which are selected within each specified range of the number of carbon atoms.

The notation $C_a$-$C_b$ haloalkylthio group in this description denotes haloalkyl-S— group with the meaning and the number of carbon atom(s) of a to b including, for example, difluoromethylthio group, trifluoromethylthio group, chlorodifluoromethylthio group, bromodifluoromethylthio group, 2,2,2-trifluoroethylthio group, 1,1,2,2-tetrafluoroethylthio group, 2-chloro-1,1,2-trifluoroethylhio group, pentafluoroethylthio group, 2-bromo-1,1,2,2-tetrafluoroethylthio group, 1,1,2,3,3,3-hexafluoropropylthio group, heptafluoropropylthio group, 1,2,2,2-tetrafluoro-1-(trifluoromethyl)ethylthio group, and nonafluorobutylthio group, as specific examples, which are selected within each specified range of the number of carbon atoms.

The notation $C_a$-$C_b$ alkylsulfinyl group in this description denotes alkyl-S(O)— group with the meaning and the number of carbon atom(s) of a to b including, for example, methylsulfinyl group, ethylsulfinyl group, n-propylsulfinyl group, i-propylsulfinyl group, n-butylsulfinyl group, i-butylsulfinyl group, s-butylsulfinyl group, and t-butylsulfinyl group, as specific examples, which are selected within each specified range of the number of carbon atoms.

The notation $C_a$-$C_b$ haloalkylsulfinyl group in this description denotes haloalkyl-S(O)— group with the meaning and the number of carbon atom(s) of a to b including, for example, difluoromethylsulfinyl group, trifluoromethylsulfinyl group, chlorodifluoromethylsulfinyl group, bromodifluoromethylsulfinyl group, 2,2,2-trifluoroethylsulfinyl group, 2-bromo-1,1,2,2-tetrafluoroethylsulfinyl group, 1,2,2,2-tetrafluoro-1-(trifluoromethyl)ethylsulfinyl group, and nonafluorobutylsulfinyl group, as specific examples, which are selected within each specified range of the number of carbon atoms.

The notation $C_a$-$C_b$ alkylsulfonyl group in this description denotes alkyl-$SO_2$— group with the meaning and the number of carbon atom(s) of a to b including, for example, methylsulfonyl group, ethylsulfonyl group, n-propylsulfonyl group, i-propylsulfonyl group, n-butylsulfonyl group, i-butylsulfonyl group, s-butylsulfonyl group, t-butylsulfonyl group, n-pentylsulfonyl group, and n-hexylsulfonyl group, as specific examples, which are selected within each specified range of the number of carbon atoms.

The notation $C_a$-$C_b$ haloalkylsulfonyl group in this description denotes haloalkyl-$SO_2$— group with the meaning and the number of carbon atom(s) of a to b including, for example, difluoromethylsulfonyl group, trifluoromethylsulfonyl group, chlorodifluoromethylsulfonyl group, bromodifluoromethylsulfonyl group, 2,2,2-trifluoroethylsulfonyl group, 1,1,2,2-tetrafluoroethylsulfonyl group, 2-chloro-1,2,2-trifluoroethylsulfonyl group, and 2-bromo-1,1,2,2-tetrafluoroethylsulfonyl group, as specific examples, which are selected within each specified range of the number of carbon atoms.

The notation $C_a$-$C_b$ alkylcarbonyl group in this description denotes alkyl-C(O)— group with the meaning and the number of carbon atom(s) of a to b including, for example, acetyl group, propionyl group, butyryl group, isobutyryl group, valeryl group, isovaleryl group, 2-methylbutanoyl group, pivaloyl group, hexanoyl group, and heptanoyl group, as specific examples, which are selected within each specified range of the number of carbon atoms.

The notation $C_a$-$C_b$ haloalkylcarbonyl group in this description denotes haloalkyl-C(O)— group with the meaning and the number of carbon atom(s) of a to b including, for example, fluoroacetyl group, chloroacetyl group, difluoroacetyl group, dichloroacetyl group, trifluoroacetyl group, chlorodifluoroacetyl group, bromodifluoroacetyl group, trichloroacetyl group, pentafluoropropionyl group, heptafluorobutanoyl group, and 3-chloro-2,2-dimethylpropanoyl group, as specific examples, which are selected within each specified range of the number of carbon atoms.

The notation $C_a$-$C_b$ alkoxylcarbonyl group in this description denotes alkyl-O—C(O)— group with the meaning and the number of carbon atom(s) of a to b including, for example, methoxycarbonyl group, ethoxycarbonyl group, n-propyloxycarbonyl group, i-propyloxycarbonyl group, n-butoxycarbonyl group, i-butoxycarbonyl group, and t-butoxycarbonyl group, as specific examples, which are selected within each specified range of the number of carbon atoms.

The notation $C_a$-$C_b$ alkylthiocarbonyl group in this description denotes alkyl-S—C(O)— group with the meaning and the number of carbon atom(s) of a to b including, for example, methylthio-C(O)— group, ethylthio-C(O)— group, n-propylthio-C(O)— group, i-propylthio-C(O)— group, n-butylthio-C(O)— group, i-butylthio-C(O)— group, and t-butylthio-C(O)— group, as specific examples, which are selected within each specified range of the number of carbon atoms.

The notation $C_a$-$C_b$ alkoxythiocarbonyl group in this description denotes alkyl-O—C(S)— group with the meaning and the number of carbon atom(s) of a to b including, for example, methoxy-C(S)— group, ethoxy-C(S)— group, n-propyloxy-C(S)— group, and i-propyloxy-C(S)— group, as specific examples, which are selected within each specified range of the number of carbon atoms.

The notation $C_a$-$C_b$ alkyldithiocarbonyl group in this description denotes alkyl-S—C(S)— group with the meaning and the number of carbon atom(s) of a to b including, for example, methylthio-C(S)— group, ethylthio-C(S)— group, n-propylthio-C(S)— group, and i-propylthio-C(S)— group, as specific examples, which are selected within each specified range of the number of carbon atoms.

The notation $C_a$-$C_b$ alkylaminocarbonyl group in this description denotes carbamoyl group substituted by alkyl group with the meaning and the number of carbon atom(s) of a to b on either one of hydrogen atoms including, for example, methylcarbamoyl group, ethylcarbamoyl group, n-propylcarbamoyl group, i-propylcarbamoyl group, n-butylcarbamoyl group, i-butylcarbamoyl group, s-butylcarbamoyl group, and t-butylcarbamoyl group, as specific examples, which are selected within each specified range of the number of carbon atoms.

The notation ($C_a$-$C_b$ alkyl)aminocarbonyl group in this description denotes carbamoyl group substituted by alkyl group with the meaning and the number of carbon atom(s) that can be identical with or different from each other of a to b on both hydrogen atoms including, for example, N,N-dimethylcarbamoyl group, N-ethyl-N-methylcarbamoyl group, N,N-diethylcarbamoyl group, N,N-di-n-propylcarbamoyl group, and N,N-di-n-butylcarbamoyl group, as specific examples, which are selected within each specified range of the number of carbon atoms.

The notation $C_a$-$C_b$ alkylaminosulfonyl group in this description denotes sulfamoyl group substituted by alkyl group with the meaning and the number of carbon atom(s) of a to b on either one of hydrogen atoms including, for example, methylsulfamoyl group, ethylsulfamoyl group, n-propylsulfamoyl group, i-propylsulfamoyl group, n-butylsulfamoyl group, i-butylsulfamoyl group, s-butylsulfamoyl group, and t-butylsulfamoyl group, as specific examples, which are selected within each specified range of the number of carbon atoms.

The notation ($C_a$-$C_b$ alkyl)aminosulfonyl group in this description denotes sulfamoyl group substituted by alkyl group with the meaning and the number of carbon atom(s) that can be identical with or different from each other of a to b on both hydrogen atoms including, for example, N,N-dimethylsulfamoyl group, N-ethyl-N-methylsulfamoyl group, N,N-diethylsulfamoyl group, N,N-di-n-propylsulfamoyl group, and N,N-di-n-butylsulfamoyl group, as specific examples, which are selected within each specified range of the number of carbon atoms.

The notation $C_a$-$C_b$ cycloalkyl($C_d$-$C_e$)alkyl group, $C_a$-$C_b$ alkoxy($C_d$-$C_e$)alkyl group, $C_a$-$C_b$ alkylthio($C_d$-$C_e$)alkyl group, or the like in this description denotes a straight-chain or branched-chain hydrocarbon group with the number of carbon atom(s) of d to e in which hydrogen atom bound to carbon atom is arbitrarily substituted by arbitrary $C_a$-$C_b$ cycloalkyl group, $C_a$-$C_b$ alkoxy group, or $C_a$-$C_b$ alkylthio group with the meaning respectively, which are selected within each specified range of the number of carbon atoms.

The notation ($C_a$-$C_b$)alkyl group substituted by $R^6$ in this description denotes a straight-chain or branched-chain hydrocarbon group with the number of carbon atom(s) of a to b in which hydrogen atom bound to carbon atom is arbitrarily substituted by arbitrary $R^6$, which are selected within each specified range of the number of carbon atoms. Then, when there are 2 or more substituent $R^6$ on each ($C_a$-$C_b$)alkyl group, each $R^6$ can be identical with or different from each other.

The notation hydroxy($C_d$-$C_e$)haloalkyl group, $C_a$-$C_b$ alkoxy($C_d$-$C_e$)haloalkyl group, or $C_a$-$C_b$ haloalkoxy($C_d$-$C_e$) haloalkyl group in this description denotes a haloalkyl group with the meaning and the number of carbon atom(s) of d to e in which hydrogen or halogen atom bound to carbon atom is arbitrarily substituted by arbitrary $C_a$-$C_b$ alkoxy group, $C_a$-$C_b$ haloalkoxy group, or hydroxy group with the meaning respectively, including, for example, 2,2,2-trifluoro-1-hydroxy-1-(trifluoromethyl)ethyl group, difluoro(methoxy)methyl group, 2,2,2-trifluoro-1-methoxy-1-(trifluoromethyl) ethyl group, difluoro(2,2,2-trifluoroetoxy)methyl group, 2,2,2-trifluoro-1-(2,2,2-trifluoroetoxy)-1-(trifluoromethyl)ethyl group, 3-(1,2-dichloro-1,2,2-trifluoroethoxy)-1,1,2,2,3,3-hexafluoropropyl group, as specific examples, which are selected within each specified range of the number of carbon atoms.

In the compound included in the present invention, substituent represented by X includes preferably halogen atom and $C_1$-$C_4$ haloalkyl group, more preferably chlorine atom, bromine atom, iodine atom, and trifluoromethyl group. When m representing the number of substituents represented by X represents 2 or higher integer, each X can be identical with or different from each other.

In the compound included in the present invention, m representing the number of substituents represented by X includes preferably 1, 2, and 3.

In the compound included in the present invention, the position of substituents represented by X includes more preferably meta and para positions with respect to the binding position of $R^1$ with carbon.

In the compound included in the present invention, substituent represented by Y includes preferably halogen atom, nitro group, $C_1$-$C_4$ alkyl group, and $C_1$-$C_4$ haloalkyl group, more preferably fluorine atom, chlorine atom, bromine atom, iodine atom, nitro group, methyl group, ethyl group, and trifluoromethyl group. When n represents an integer of 2, each Y can be identical with or different from each other.

In the compound included in the present invention, n representing the number of substituents represented by Y includes more preferably 0 and 1.

In the compound included in the present invention, the position of substituents represented by Y includes more preferably ortho position with respect to the binding position with $R^2$.

In the compound included in the present invention, substituent represented by $R^1$ includes preferably $C_1$-$C_4$ haloalkyl group, more preferably difluoromethyl group, chlorodifluoromethyl group, bromodifluoromethyl group, and trifluoromethyl group, and most preferably chlorodifluoromethyl group and trifluoromethyl group.

In the compound included in the present invention, substituent represented by $R^2$ includes preferably halogen atom, cyano group, nitro group, —$NH_2$, —$NHR^4$, —OH, —$OR^3$, benzyloxy group, —$OSO_2R^3$, phenylsulfonyloxy group, paratoluenesulfonyloxy group, —C(O)OH, —C(O)$R^3$, —C(O)$NH_2$, and —C(O)N($R^b$)$R^a$, more preferably chlorine atom, bromine atom, iodine atom, cyano group, nitro group, amino group, —$NHR^4$, hydroxy group, methoxy group, methoxymethyloxy group, acetyloxy group, benzyloxy group, methansulfonyloxy group, trifluoromethansulfonyloxy group, paratoluenesulfonyloxy group, —C(O)OH, methoxycarbonyl group, ethoxycarbonyl group, —C(O) $NH_2$, and —C(O)N($R^b$)$R^a$.

In the compound included in the present invention, substituent represented by $R^3$ includes preferably $C_1$-$C_4$ alkyl group, $C_1$-$C_4$ alkoxy($C_1$-$C_4$)alkyl group, and $C_1$-$C_4$ haloalkyl group, more preferably methyl group, ethyl group, methoxymethyl group, methoxyethyl group, ethoxymethyl group, and trifluoromethyl group.

In the compound included in the present invention, substituent represented by $R^4$ includes preferably —CHO, $C_1$-$C_4$ alkylcarbonyl group, and $C_1$-$C_4$ alkoxylcarbonyl group, more preferably formyl group, acetyl group, propionyl group, methoxycarbonyl group, and ethoxycarbonyl group.

In the compound included in the present invention, substituent represented by $R^5$ includes preferably hydrogen atom.

In the compound included in the present invention, substituent represented by $R^a$ includes preferably ($C_1$-$C_4$)alkyl group arbitrarily substituted by $R^6$, —N($R^9$)$R^8$, —C(O)$OR^7$, —C(O)$NH_2$, —C(O)$NHR^7$, —C($R^{15}$)=$NOR^{14}$, phenyl group, phenyl group substituted by (Z)$_{p1}$, D-5, D-7, D-10, D-11, D-12, D-14, D-15, D-18, D-31, D-32, D-38, D-39, D-41, D-42, D-44, E-1, or E-7.

In the compound included in the present invention, substituent represented by $R^b$ includes preferably hydrogen atom, $C_1$-$C_6$ alkyl group, $C_1$-$C_4$ alkoxy($C_1$-$C_4$)alkyl group, cyano($C_1$-$C_4$)alkyl group, $C_3$-$C_6$ alkynyl group, —C(O)$R^7$, and —C(O)$OR^7$, more preferably hydrogen atom, methyl group, ethyl group, methoxymethyl group, cyanomethyl group, propargyl group, acetyl group, propionyl group, butyryl group, pivaloyl group, methoxycarbonyl group, and ethoxycarbonyl group.

In the compound included in the present invention, substituent represented by $R^6$ includes preferably halogen atom, cyano group, $C_3$-$C_6$ cycloalkyl group, $C_1$-$C_4$ alkoxy group, $C_1$-$C_4$ haloalkoxy group, —C(O)N($R^{13}$)$R^{12}$, —C($R^{15}$)=$NOR^{14}$, phenyl group, phenyl group substituted by (Z)$_{p1}$, D-11 to D-14, D-18, D-19, D-25, D-26, D-31, D-32, D-36, D-38, D-41, D-44, D-45, E-1, E-2, or E-5, more preferably fluorine atom, chlorine atom, bromine atom, cyano group, cyclopropyl group, methoxy group, ethoxy group, 2,2,2-trifluoroethoxy group, —C(O)N($R^{13}$)$R^{12}$, —CH=$NOCH_3$, phenyl group, phenyl group substituted by (Z)$_{p1}$, D-14, D-19, D-31, D-32, D-36, D-38 and E-5.

In the compound included in the present invention, substituent represented by Z includes preferably halogen atom, cyano group, nitro group, $C_1$-$C_4$ alkyl group, $C_1$-$C_4$ haloalkyl group, and $C_1$-$C_4$ haloalkoxy group, more preferably fluorine atom, chlorine atom, bromine atom, cyano group, nitro group, methyl group, trifluoromethyl group, and trifluoromethoxy group. When p1, p2, p3, or p4 representing the number of substituents represented by Z represents 2 or higher integer, each Z can be identical with or different from each other.

In the compound included in the present invention, p1 representing the number of substituents represented by Z includes preferably 1 and 2.

In the compound included in the present invention, p2 representing the number of substituents represented by Z includes preferably 0 and 1.

In the compound included in the present invention, p3 representing the number of substituents represented by Z includes preferably 0 and 1.

In the compound included in the present invention, p4 representing the number of substituents represented by Z includes preferably 0 and 1.

In the compound included in the present invention, p5 representing the number of substituents represented by Z includes preferably 0 and 1.

In the compound included in the present invention, substituent represented by $R^7$ includes preferably $C_1$-$C_4$ alkyl group, $C_1$-$C_4$ haloalkyl group, $C_1$-$C_4$ alkoxy($C_1$-$C_4$)alkyl group, $C_1$-$C_4$ alkylthio($C_1$-$C_4$)alkyl group, $C_3$-$C_8$ cycloalkyl group, $C_3$-$C_6$ alkenyl group, and $C_3$-$C_6$ alkynyl group, more preferably methyl group, ethyl group, n-propyl group, i-propyl group, n-butyl group, i-butyl group, s-butyl group, t-butyl group, trifluoromethyl group, chloroethyl group, 2,2,2-trifluoroethyl group, methoxymethyl group, ethoxymethyl group, methoxyethyl group, methylthiomethyl group, cyclopropyl group, allyl group, and propargyl group.

In the compound included in the present invention, substituent represented by $R^8$ includes preferably $C_1$-$C_4$ haloalkyl group, —C(O)$R^{12}$, —C(O)O$R^{12}$, phenyl group, phenyl group substituted by $(Z)_{p1}$, D-3, D-4, D-18, D-38, D-41, D-42, D-44, or D-45, more preferably 2,2,2-trifluoroethyl group, —C(O)$R^{12}$, —C(O)O$R^{12}$, phenyl group, phenyl group substituted by $(Z)_{p1}$, D-18, D-38, and D-41.

In the compound included in the present invention, substituent represented by $R^9$ includes preferably hydrogen atom, $C_1$-$C_6$ alkyl group, and $C_3$-$C_6$ alkynyl group, more preferably hydrogen atom, methyl group, ethyl group, and propargyl group.

In the compound included in the present invention, substituent represented by $R^{10}$ includes preferably $C_1$-$C_4$ alkyl group, more preferably methyl group and ethyl group.

In the compound included in the present invention, substituent represented by $R^{11}$ includes preferably $C_1$-$C_4$ alkyl group, more preferably methyl group. When q2, q3, or q4 representing the number of substituents represented by $R^{11}$ represents 2 or higher integer, each $R^{11}$ can be identical with or different from each other, and two $R^{11}$s substituted on the same carbon atom indicate that the two $R^{11}$s can form an oxo ring together.

In the compound included in the present invention, q2 representing the number of substituents represented by $R^{11}$ includes preferably 0, 1, and 2.

In the compound included in the present invention, q3 representing the number of substituents represented by $R^{11}$ includes preferably 0, 1, and 2.

In the compound included in the present invention, q4 representing the number of substituents represented by $R^{11}$ includes preferably 0, 1, and 2.

In the compound included in the present invention, substituent represented by $R^{12}$ includes preferably $C_1$-$C_4$ alkyl group, $C_1$-$C_4$ haloalkyl group, $C_3$-$C_6$ cycloalkyl($C_1$-$C_4$)alkyl group, $C_3$-$C_6$ cycloalkyl group, $C_3$-$C_6$ alkenyl group, and $C_3$-$C_6$ alkynyl group, more preferably methyl group, ethyl group, 2-fluoroethyl group, 2-chloroethyl group, 2-bromoethyl group, 2,2,2-trifluoroethyl group, cyclopropylmethyl group, cyclopropyl group, allyl group, and propargyl group.

In the compound included in the present invention, substituent represented by $R^{13}$ includes preferably hydrogen atom and $C_1$-$C_4$ alkyl group, more preferably hydrogen, methyl group, and ethyl group.

In the compound included in the present invention, substituent represented by $R^{14}$ includes preferably $C_1$-$C_4$ alkyl group, more preferably methyl group and ethyl group.

In the compound included in the present invention, substituent represented by $R^{15}$ includes preferably hydrogen atom and $C_1$-$C_4$ alkyl group, more preferably hydrogen atom and methyl group.

In the compound included in the present invention, r representing the number of oxygen on sulfur atom includes 0, 1, and 2.

In the compound included in the present invention, t representing the number of oxygen on nitrogen atom of pyridine ring includes 0 and 1.

A process intermediate of the present invention can, for example, be produced by the following procedures.

Procedure A

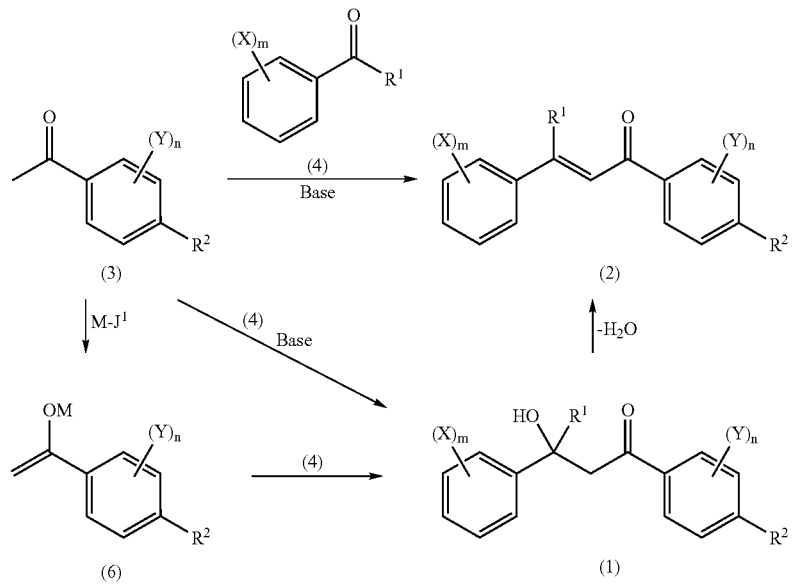

Namely, from the compound represented by the well known general formula (3) (where, Y, $R^2$, and n represent the same meaning as defined in the general formula (1) or (2).)

and the compound represented by the well known general formula (4) (where, X, $R^1$, and m represent the same meaning as defined in the general formula (1) or (2)), the compound represented by the general formula (2) (where, X, Y, $R^1$, $R^2$, m, and n represent the same meaning as above.) can be obtained according to a well known procedure described in the document, for example the procedure described in Asian J. Chem., vol. 13, p. 1560 (2001).

Also, after the compound represented by the general formula (3) and the compound represented by the general formula (4) are made into the compound represented by the general formula (1) (where, X, Y, $R^1$, $R^2$, m, and n represent the same meaning as above) according to the well known procedure described in the document, for example the procedure described in the document such as Tetrahedron, vol. 58, p. 8269 (2002), and Synthesis, p. 330 (1996) and vol. 26, p. 2205 (1990), the compound represented by the general formula (2) can be obtained according to a well known procedure described in the document, for example, the procedures described in Tetrahedron, vol. 59, p. 4363 (2003), J. Org. Chem., vol. 55, p. 132 (1990), and Org. Synth., vol. 65, p. 12 (1987).

In addition, as a manufacturing process of the compound represented by the general formula (1), the compound represented by the general formula (1) can be obtained according to a well known procedure described in the document, for example the procedure described in J. Am. Chem. Soc., vol. 96, p. 7503 (1974), and Bull. Chem. Soc. Jpn., vol. 68, p. 1180 (1995), after the compound represented by the general formula (3) is made into enolate represented by the general formula (6) (where, Y, $R^2$, and n represent the same meaning as above, M represents $C_1$-$C_4$ trialkylsilyl group (for example, trimethylsilyl group) or $C_1$-$C_6$ trialkyltin group (for example, tributyltin group), and $J^1$ represents chlorine atom or $C_1$-$C_4$ alkoxy group (for example, methoxy group).) according to a well known procedure described in the document, for example into silylenolate according to the procedure described in such as J. Org. Chem., vol. 34, p. 2324 (1969) and into tinenolate according to the procedure described in such as Tetrahedron, vol. 40, p. 2329 (1984).

Also, the compound represented by the general formula (2) can be synthesized, for example, as follows.

Procedure B

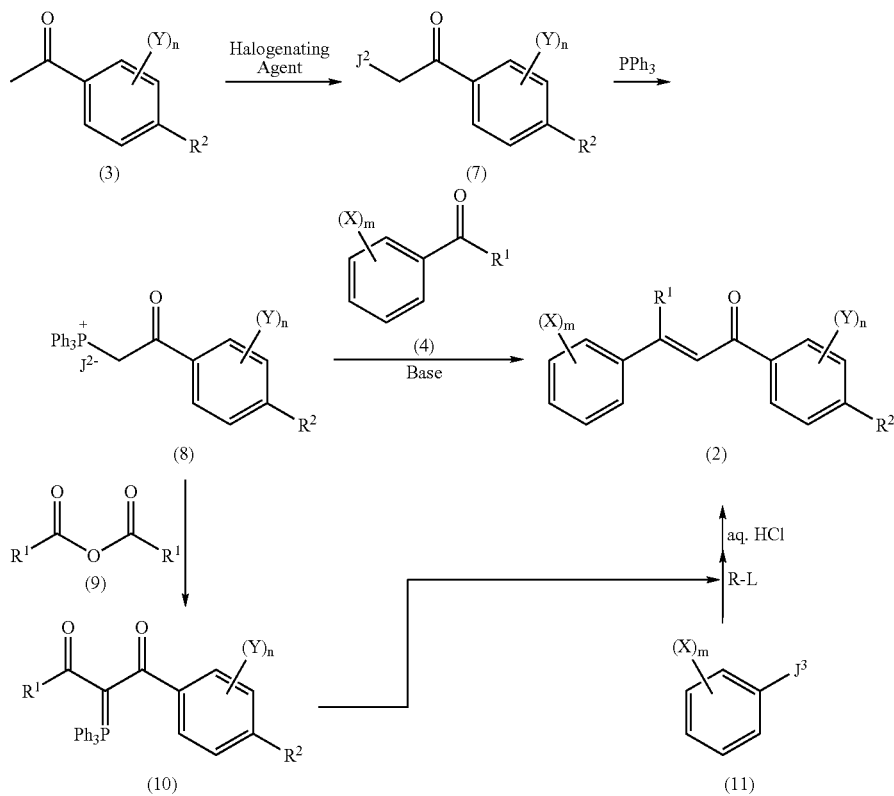

Namely, after the compound represented by the general formula (7) (where, Y, $R^2$, and n represent the same meaning as above and $J^2$ represents chlorine atom or bromine atom.) is made through the reaction of the compound represented by the general formula (3) (where, Y, $R^2$, and n represent the same meaning as above.) with halogenating agent (for example, bromine), phosphonium salt represented by the general formula (8) (where, Y, $R^2$, n, and $J^2$ represent the same meaning as above.) is obtained according to a well known procedure described in the document, for example the procedure described in J. Indian Chem. Soc., vol. 65, p. 134 (1988), and then the compound represented by the general formula (2) (where, X, Y, $R^1$, $R^2$, m, and n represent the same meaning as above.) can be obtained through the reaction with the compound represented by the well known general formula (4) (where, X, $R^1$, and m represent the same meaning as above.) in the presence of a base.

Also, after the compound represented by the general formula (7) is made into phosphonium salt represented by the general formula (8) according to a well known procedure described in the document, for example the procedure described in J. Org. Chem., vol. 53, p. 5558 (1988), the compound represented by the general formula (2) can be obtained by reacting the compound represented by the general formula (10) (where, Y, $R^1$, $R^2$, and n represent the same meaning as above.) that can be obtained by reacting with the compound represented by the well known general formula (9) (where, $R^1$ represents the same meaning as above.) with lithium salt that can be obtained through halogen-metal exchange reaction of the compound represented by the general formula (11) (where, X and m represent the same meaning as above and $J^3$ represents bromine atom or iodine atom.) according to a well known procedure described in the document, for example the procedure described in such as J. Chem. Soc., Perkin Trans. 1, p. 2531 (1996).

In the compound represented by the general formula (2), the compound represented by the general formulae (2-2) to (2-4) in which $R^2$ has a carbonyl structure can also be obtained as follows.

Procedure C

Namely, the compound represented by the general formula (2-2) (where, X, Y, $R^1$, $R^3$, m, and n represent the same meaning as above.) can be obtained by reacting the compound represented by the general formula (2-1) (where, X, Y, $R^1$, m, and n represent the same meaning as above and $R^{2-1}$ represents bromine atom, iodine atom, halosulfonyloxy group (for example, fluorosulfonyloxy group), $C_1$-$C_4$ haloalkylsulfonyloxy group (for example, trifluoromethanesulfonyloxy group) or arylsulfonyloxy group (for example, benzenesulfonyloxy group)) according to a well known procedure described in the document, for example the reaction condition such as CO insertion reaction using transition-metal catalyst such as palladium described in J. Org. Chem., vol. 39, p. 3318 (1974) and the like.

Also, the compound represented by the general formula (2-3) (where, X, Y, $R^1$, m, and n represent the same meaning as above.) can be obtained by reacting the compound represented by the general formula (2-1) according to, for example, the reaction condition such as CO insertion reaction using transition-metal catalyst such as palladium described in J. Org. Chem., vol. 64, p. 6921 (1999).

The compound of the present invention represented by the general formula (2-4) (where, X, Y, $R^1$, $R^a$, $R^b$, m, and n

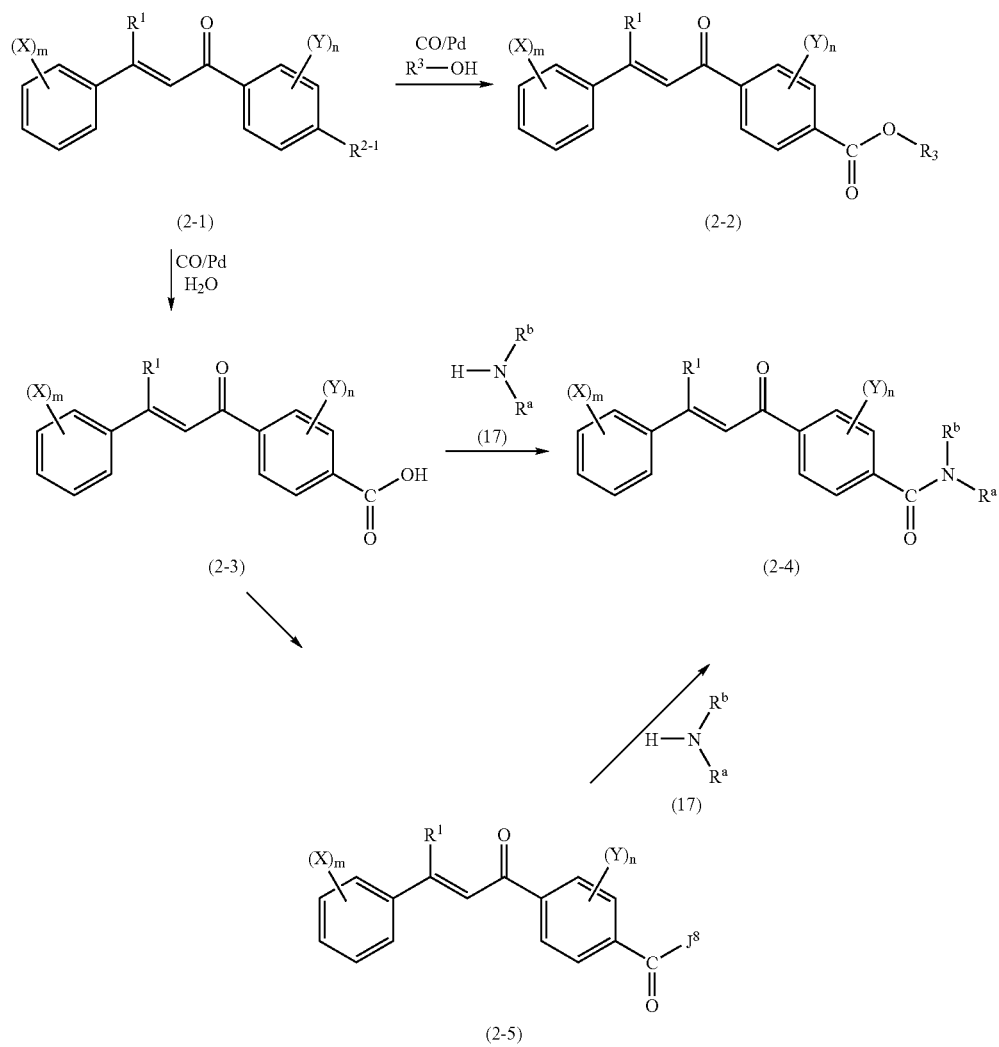

represent the same meaning as above.) can be obtained by reacting the compound represented by the general formula (2-3) with the compound represented by the general formula (17) (where, $R^a$, and $R^b$ represent the same meaning as above.) using a condensation agent in the presence of a base if necessary using a solvent inert to the reaction if necessary.

The compound represented by the general formula (17) can be used as a reaction substrate from 1 to 100 equivalent amounts per one equivalent amount of the compound represented by the general formula (2-3).

A condensation agent, which can be used without specific limitation as long as it is used for usual amide synthesis, but, for example Mukaiyama reagent (2-chloro-N-methylpyridinium iodide), DCC (1,3-dicyclohexylcarbodiimide), WSC (1-ethyl-3-(3-dimethylaminopropyl)-carbodiimide hydrochloride), CDI (carbonyldiimidazol), dimethylpropynylsulfonyum bromide, propargyltriphenylphosphonium bromide, DEPC (cyano diethyl phosphate), can be used from 1 to 4 equivalent amounts to the compound represented by the general formula (2-3).

A solvent, if it is used, can be used without specific limitation as long as it does not inhibit progression of the reaction and includes, for example, aromatic hydrocarbons such as benzene, toluene, and xylene, aliphatic hydrocarbons such as hexane and heptane, alicyclic hydrocarbon such as cyclohexane, aromatic halogenated hydrocarbons such as chlorobenzene and dichlorobenzene, aliphatic halogenated hydrocarbons such as dichloromethane, chloroform, carbon tetrachloride, 1,2-dichloroethane, 1,1,1-trichloroethane, trichloroethylene, and tetrachloroethylene, ethers such as diethylether, 1,2-dimethoxyethane, tetrahydrofuran, and 1,4-dioxane, esters such as ethyl acetate, and ethyl propionate, amides such as N,N-dimethylformamide, N,N-dimethylacetamide, and N-methyl-2-pyrrolidone, amines such as triethylamine, tributylamine, and N,N-dimethylaniline, pyridines such as pyridine and picoline, acetonitrile, and dimethylsulfoxide. These solvents can be used alone or 2 or more of them can be mixed to be used.

Addition of a base is not necessarily needed, but if the base is used, for example, alkali metal hydroxides such as sodium hydroxide and potassium hydroxide, alkali metal carbonates such as sodium carbonate and potassium carbonate, alkali metal bicarbonates such as sodium hydrogen carbonate and potassium bicarbonate, organic bases such as triethylamine, tributylamine, N,N-dimethylaniline, pyridine, 4-(dimethylamino)pyridine, imidazole, 1,8-diazabicyclo(5,4,0)-7-undecene, can be used from 1 to 4 equivalent amounts to the compound represented by the general formula (2-3).

A reaction temperature can be set arbitrarily from −60° C. to the reflux temperature of the reaction mixture, while reaction time can be set arbitrarily in a range of 5 minutes to 100 hours generally, depending on the concentration of the reaction substrate and the reaction temperature.

In general, using 1 to 20 equivalent amounts of the compound represented by the general formula (17) and 1 to 4 equivalent amounts of condensation agents such as WSC (1-ethyl-3-(3-dimethylaminopropyl)-carbodiimide hydrochloride) and CDI (carbonyldiimidazol) per one equivalent amount of the compound represented by, for example, the general formula (2-3), it is preferable to react them with or without solvents such as dichloromethane, chloroform, diethylether, tetrahydrofuran, and 1,4-dioxane in the presence of 1 to 4 equivalent amounts of base such as potassium carbonate, triethylamin, pyridine, and 4-(dimethylamino)pyridine if necessary for 10 minutes to 24 hours within a range from 0° C. to the reflux temperature of these solvents.

Also, The compound represented by the general formula (2-4) can be synthesized by reacting the compound represented by the general formula (2-5) (where, X, Y, $R^1$, m, and n represent the same meaning as above and $J^8$ represents chlorine atom, bromine atom, $C_1$-$C_4$ alkylcarbonyloxy group (for example, pivaloyloxy group), $C_1$-$C_4$ alkoxycarbonyloxy group (for example, isobutyloxycarbonyloxy group), or azolyl group (for example, imidazole-1-yl group).) that can be synthesized from the compound represented by the general formula (2-3) using a well known procedure described in the document, for example the procedure to react with halogenating agents such as thionyl chloride, phosphorus pentachloride, or oxalyl chloride, the procedure to react with organic acid halides such as pivaloyl chloride or isobutyl chloroformate in the presence of, if necessary, a base, or the procedure to react with carbonyldiimidazole or sulfonyldiimidazole, with the compound represented by the general formula (17) in the presence of, if necessary, a base using, if necessary, a solvent inert to the reaction.

The compound represented by the general formula (17) can be used as a reaction substrate from 1 to 50 equivalent amounts per one equivalent amount of the compound represented by the general formula (2-5).

If a solvent is used, the solvent can be used without specific limitation as long as it does not inhibit progress of the reaction and includes, for example, aromatic hydrocarbons such as benzene, toluene, and xylene, aliphatic hydrocarbons such as hexane and heptane, alicyclic hydrocarbon such as cyclohexane, aromatic halogenated hydrocarbons such as chlorobenzene and dichlorobenzene, aliphatic halogenated hydrocarbons such as dichloromethane, chloroform, carbon tetrachloride, 1,2-dichloroethane, 1,1,1-trichloroethane, trichloroethylene, and tetrachloroethylene, ethers such as diethylether, 1,2-dimethoxyethane, tetrahydrofuran, and 1,4-dioxane, esters such as ethyl acetate, and ethyl propionate, amides such as N,N-dimethylformamide, N,N-dimethylacetamide, and N-methyl-2-pyrrolidone, amines such as triethylamine, tributylamine, and N,N-dimethylaniline, pyridines such as pyridine and picoline, acetonitrile, and water. These solvents can be used alone or 2 or more of them can be mixed to be used.

Addition of a base is not necessarily needed, but if a base is used, for example, alkali metal hydroxides such as sodium hydroxide and potassium hydroxide, alkali metal carbonates such as sodium carbonate and potassium carbonate, alkali metal bicarbonates such as sodium hydrogen carbonate and potassium bicarbonate, organic bases such as triethylamine, tributylamine, N,N-dimethylaniline, pyridine, 4-(dimethylamino)pyridine, imidazole, 1,8-diazabicyclo(5,4,0)-7-undecene, can be used from 1 to 4 equivalent amounts to the compound represented by the general formula (2-5).

A reaction temperature can be set arbitrarily from −60° C. to the reflux temperature of the reaction mixture, while reaction time can be set arbitrarily from 5 minutes to 100 hours generally, depending on the concentration of the reaction substrate and the reaction temperature.

In general, using 1 to 10 equivalent amounts of the compound represented by the general formula (17) per one equivalent amount of the compound represented by for example, the general formula (2-5), it is preferable to react them with or without solvents such as dichloromethane, chloroform, diethylether, tetrahhydrofuran, 1,4-dioxane, ethyl acetate, and acetonitrile in the presence of 1 to 2 equivalent amounts of base such as potassium carbonate, triethylamine, pyridine, and 4-(dimethylamino)pyridine if necessary for 10 minutes to 24 hours within a range from 0° C. to the reflux temperature of these solvents.

Some of the compounds represented by the general formula (17) that is used for the reaction are well known compounds, and some of which are available as articles on the market. Others can be synthesized according to the procedure described in, for example, Justus Liebigs Ann. Chem., p. 920 (1979), U.S. Pat. No. 5,990,323, and Publication No. WO 96/011200 and other respective general synthesis procedures described in the document for primary and secondary alkylamines.

In procedures A to C, after usual additional treatment, such as direct condensation or dissolution in organic solvent, and condensation after washing with water or putting into ice water, and then condensation after organic solvent extraction, is done for the reaction mixture after the completion of the reaction, the intended compound of the present invention can be obtained. Also, when purification is needed, separation or purification can be done using an optional purifying procedure such as recrystallization, column chromatography, thin-layer chromatography, and liquid chromatography fractionation.

The compound represented by the general formula (4) can be synthesized, for example, as follows.

Reaction Formula 1

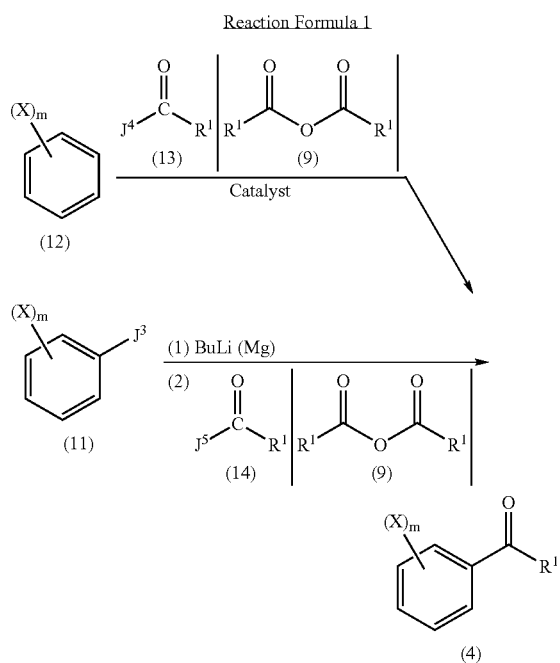

Namely, the compound represented by the general formula (4) (where, X, $R^1$, and m represent the same meaning as above) can be obtained according to general aromatic acylation reaction described in the document between the compound represented by the well known general formula (12) (where, X and m represent the same meaning as above) and the compound represented by the well known general formula (13) (where, $R^1$ represents the same meaning as above and $J^4$ represents halogen atom and leaving groups such as trifluoromethanesulfonyloxy group and 2-pyridyloxy group) or the compound represented by the well known general formula (9) (where, $R^1$ represents the same meaning as above), for example by reacting according to the procedure described in such as Chem. Lett., p. 783 (1990) and J. Org. Chem., vol. 56, p. 1963 (1991).

Otherwise, after a general procedure described in the document, for example, after lithiation of the compound represented by the well known general formula (11) (where, X, m, and $J^3$ represent the same meaning as above) is done, the compound represented by the general formula (4) can be obtained by reacting with the compound represented by the well known general formula (14) (where, $R^1$ represents the same meaning as above and $J^5$ represents halogen atom, hydroxyl group, metal salt (for example, —OLi, —ONa), $C_1$-$C_4$ alkoxy group (for example, methoxy group and ethoxy group), di($C_1$-$C_4$ alkyl)amino group (for example, diethylamino group), $C_1$-$C_4$ alkoxy($C_1$-$C_4$ alkyl)amino group (for example, O,N-dimethylhydroxyamino group), or cyclic amino group (for example, piperidine-1-yl group, morpholine-4-yl group, 4-methylpiperazine-1-yl group).) or the compound represented by the well known general formula (9) as described in such as J. Am. Chem. Soc., vol. 77, p. 3657 (1955), Tetrahedron Lett., vol. 21, p. 2129 (1980) and vol. 32, p. 2003 (1991), or U.S. Pat. No. 5,514,816, or with the compound represented by the general formula (14) or the compound represented by the general formula (9) as described in such as Heterocycles, vol. 25, p. 221 (1987), Synth. Commun., vol. 15, p. 1291 (1985) and vol. 20, p. 1469 (1990), and German Patent Publication (DE 19727042 A) after forming Grignard reagent.

Also, in the general formula (4), the compound represented by the general formula (4-1) where $R^1$ represents trifluoromethyl group can be synthesized as follows.

Reaction Formula 2

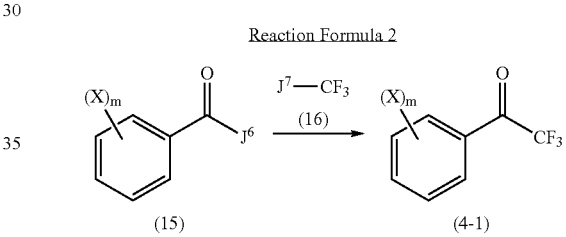

Namely, the compound represented by the general formula (4-1) (where, X and m represent the same meaning as above.) can also be obtained by reacting the compound represented by the well known general formula (15) (where, X and m represent the same meaning as above and $J^6$ represents halogen atom or $C_1$-$C_4$ alkoxy group (for example, methoxy group).) with the compound represented by the well known general formula (16) (where, $J^7$ represents tri($C_1$-$C_4$alkylsilyl group (for example, trimethylsilyl group).) according to a well known procedure described in the document, for example the procedure described in J. Org. Chem., 1999, vol. 64, p. 2873, J. Org. Chem., 1991, vol. 56, p. 984 or the like.

In each of these reactions, a process intermediate representing a raw material compound of procedures A and B, respectively, can be obtained through a usual additional treatment after the completion of the reaction.

In addition, the respective process intermediates produced by these procedures can be used as they are for the reaction of the next process without undergoing separation or purification.

A process intermediate included in the present invention includes, for specific example, the compound listed in Table 1 below, but the present invention is not limited to them.

The notation Et in the Tables denotes ethyl group, n-Pr and Pr-n denote normal propyl group, i-Pr and Pr-i denote isopropyl group, c-Pr and Pr-c denote cyclopropyl group, and Ph denotes phenyl group;

Aromatic heterocycle represented by D-1a to D-46a in the Tables denotes the following structure, respectively;
D-1a:
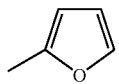
D-1b:
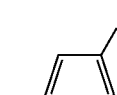
D-1c:
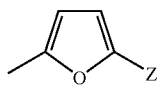
D-2a:
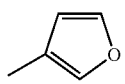
D-2b:
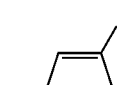
D-3a:
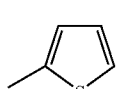
D-3b:
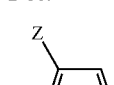
D-3c:
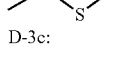
D-3d:
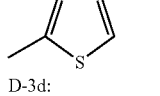
D-4a:
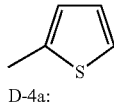
D-4b:
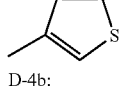
D-5a:
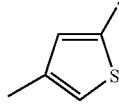
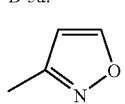
-continued
D-5b:
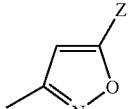
D-6a:
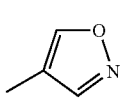
D-6b:
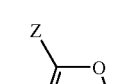
D-7a:
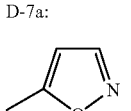
D-7b:
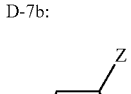
D-8a:
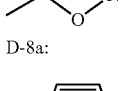
D-8b:
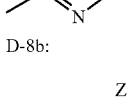
D-9b:
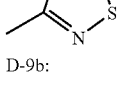
D-10a:
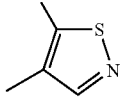
D-10b:
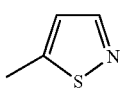
D-11a:
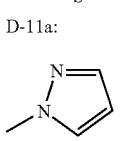

D-11b:
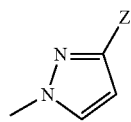
D-11c:
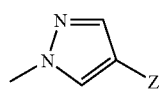
D-12a:
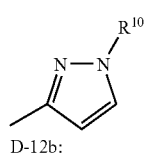
D-12b:
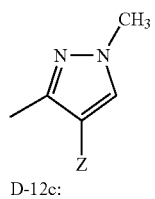
D-12c:
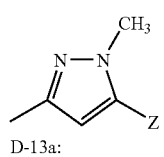
D-13a:
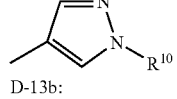
D-13b:
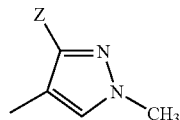
D-13c:
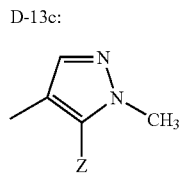
D-14a:
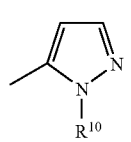
D-14b:
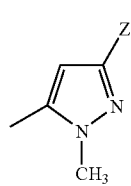
D-15a:
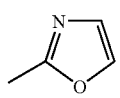
D-15b:
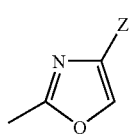
D-15c:
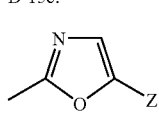
D-16a:
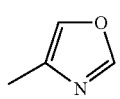
D-16b:
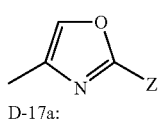
D-17a:
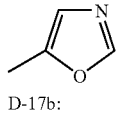
D-17b:
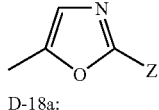
D-18a:
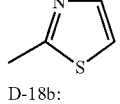
D-18b:
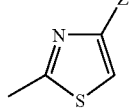
D-18c:
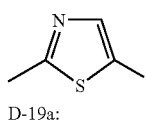
D-19a:
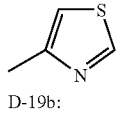
D-19b:
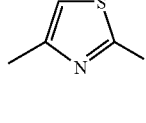

-continued
D-20a:
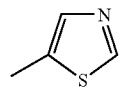
D-20b:
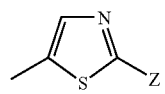
D-20c:
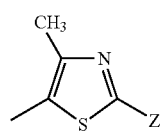
D-21a:
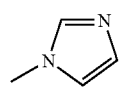
D-22a:
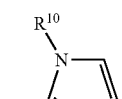
D-22b:
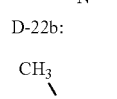
D-22c:
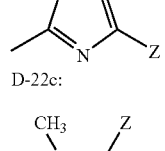
D-23a:
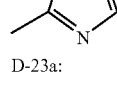
D-24a:
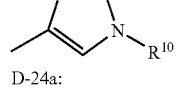
D-24b:
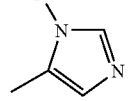
D-25a:
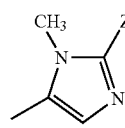
-continued
D-26a:
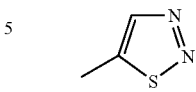
D-26b:
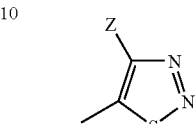
D-27a:
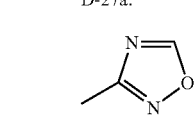
D-27b:
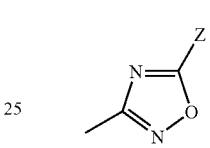
D-28a:
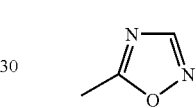
D-28b:
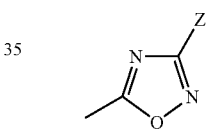
D-29a:
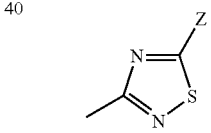
D-30a:
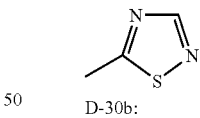
D-30b:
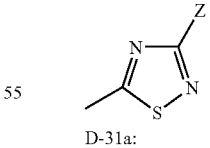
D-31a:
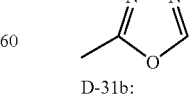
D-31b:
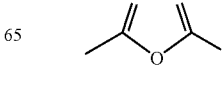

-continued
D-32a:
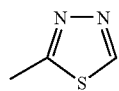
D-32b:
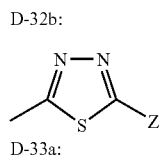
D-33a:
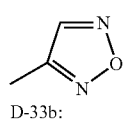
D-33b:
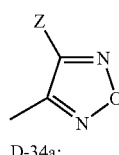
D-34a:
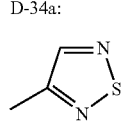
D-34b:
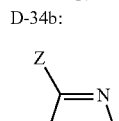
D-35a:
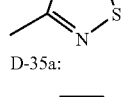
D-36a:
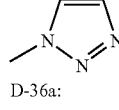
D-36b:
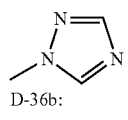
D-37a:
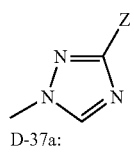
D-38a:
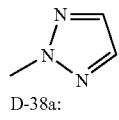
D-38b:
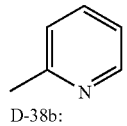
D-38c:
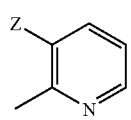
-continued
D-38c:
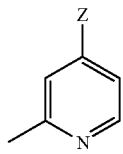
D-38d:
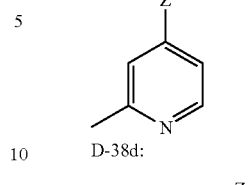
D-38e:
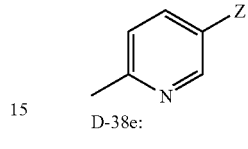
D-38f:
D-38g:
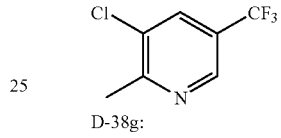
D-39a:
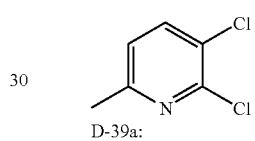
D-39b:
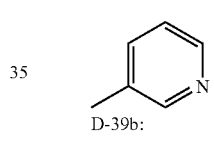
D-39c:
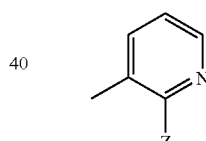
D-39d:
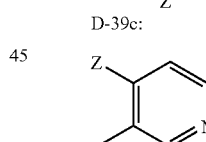
D-39e:
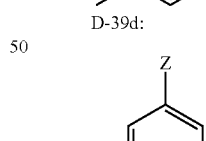
D-39f:
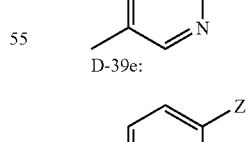
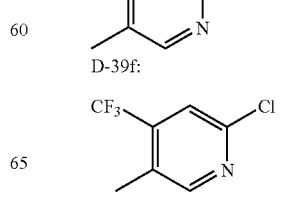

-continued
D-39g:
D-40a:
D-40b:
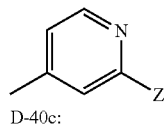
D-40c:
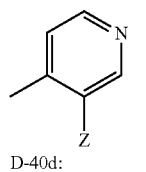
D-40d:
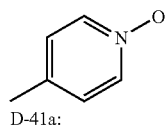
D-41a:
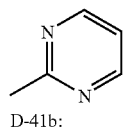
D-41b:
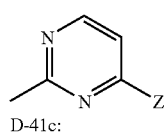
D-41c:
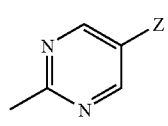
D-42a:
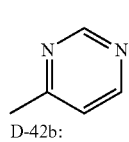
D-42b:
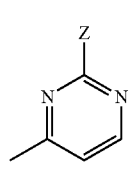
D-42c:
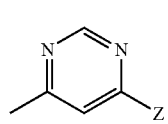
-continued
D-42d:
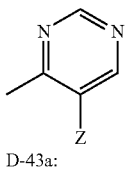
D-43a:
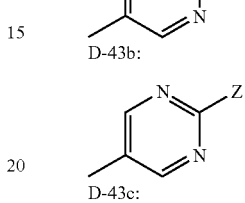
D-43b:
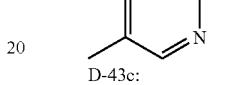
D-43c:
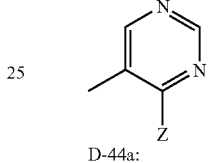
D-44a:
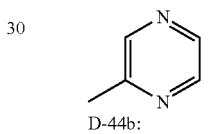
D-44b:
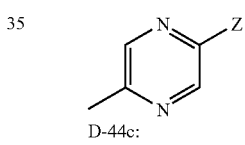
D-44c:
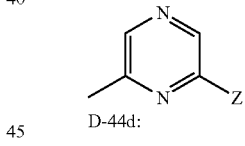
D-44d:
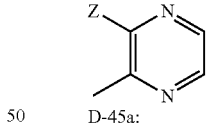
D-45a:
D-45b:
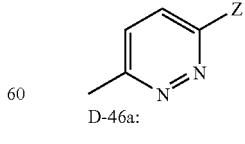
D-46a:
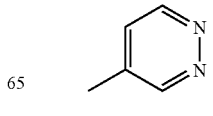

for example, the notation (CH$_2$(D-14a)CH$_3$) denotes 1-methylpyrazole-5-ylmethyl group and the notation (CH$_2$(D-19b)CH$_3$) denotes 2-methylthiazole-4-ylmethyl group.

An aliphatic heterocycle represented by E-1a to E-8b in the Tables represent the following structure, respectively;

E-1a:
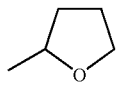

E-1b:
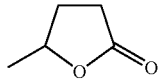

E-2a:
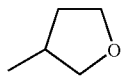

E-2b:
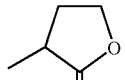

E-2c:
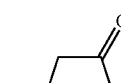

E-3a:
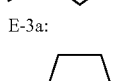

E-4a:
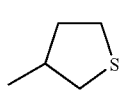

E-4b:
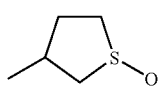

E-4c:
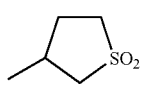

E-4d:
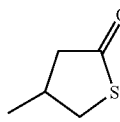

E-5a:
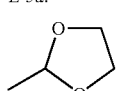

E-5b:
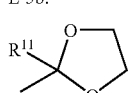

-continued

E-6a:
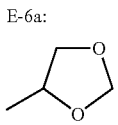

E-6b:
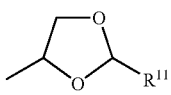

E-6c:
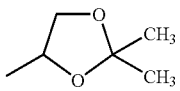

E-7a:
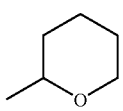

E-8a:
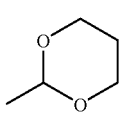

E-8b:
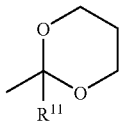

for example, the notation (CH$_2$(E-5b)CH$_3$) denotes 2-methyl-1,3-dioxolane-2-ylmethyl.

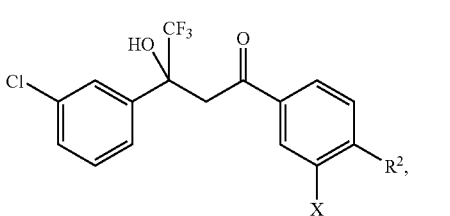
[1]-1

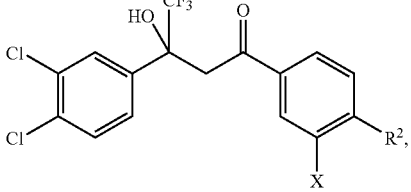
[1]-2

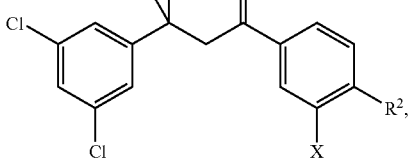
[1]-3

-continued
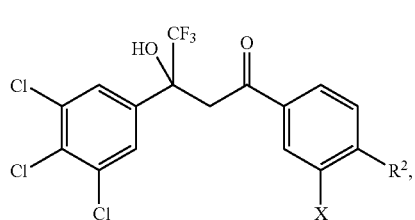 [1]-4
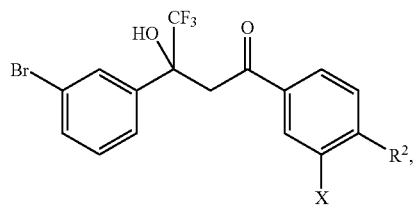 [1]-5
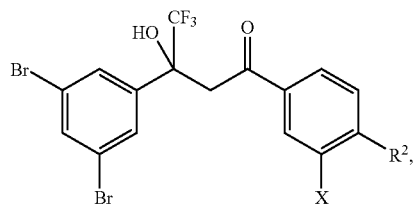 [1]-6
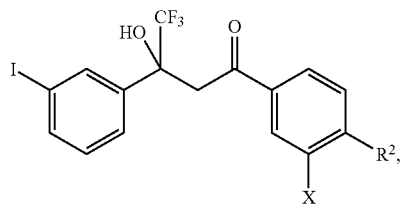 [1]-7
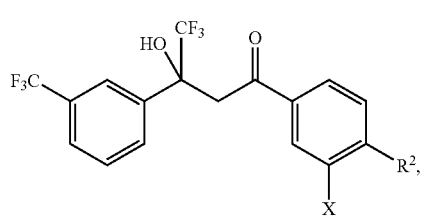 [1]-8
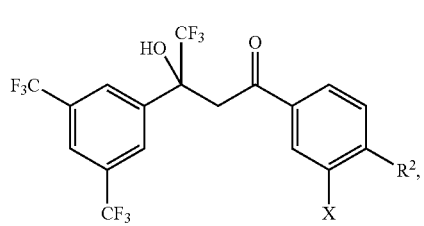 [1]-9
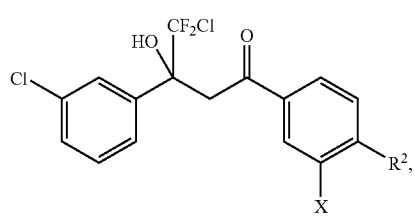 [1]-10
-continued
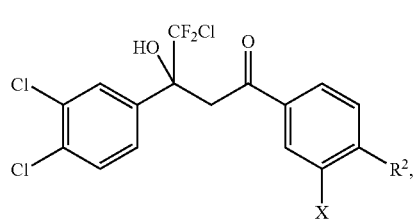 [1]-11
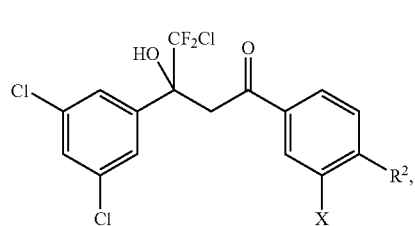 [1]-12
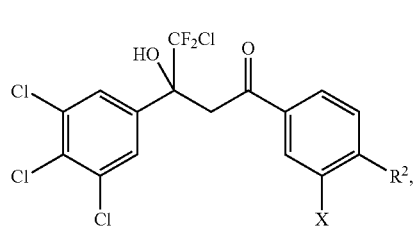 [1]-13
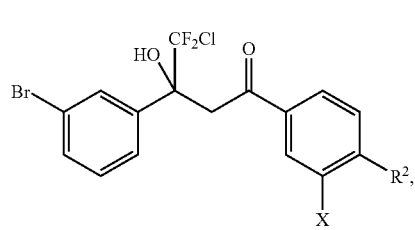 [1]-14
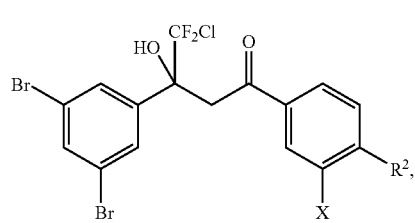 [1]-15
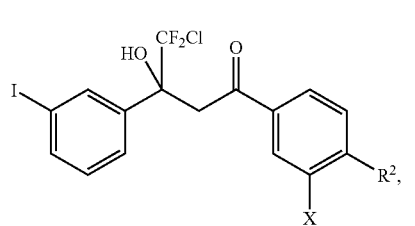 [1]-16
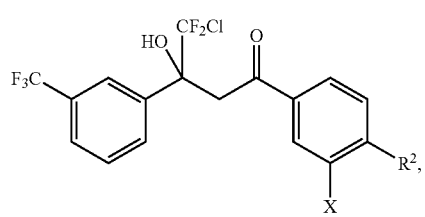 [1]-17

-continued
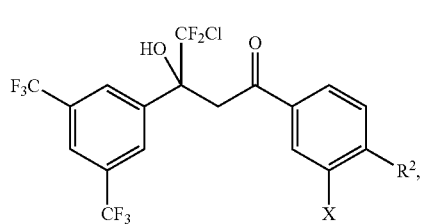 [1]-18
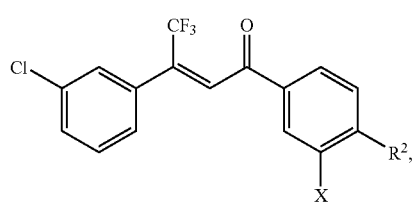 [2]-1
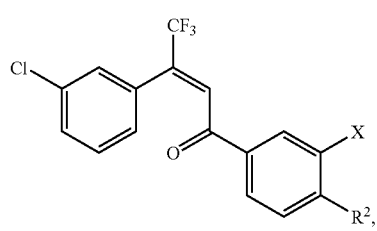 [2]-2
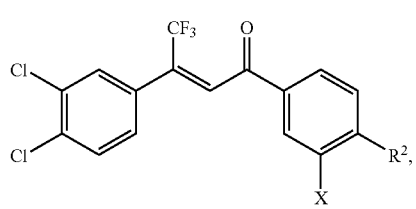 [2]-3
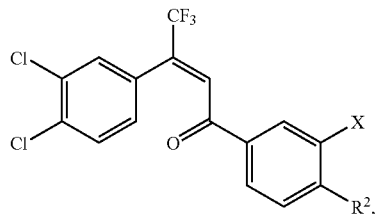 [2]-4
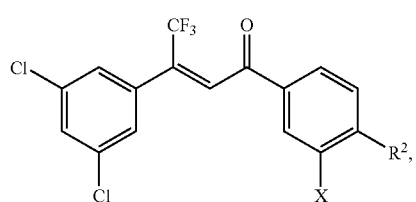 [2]-5
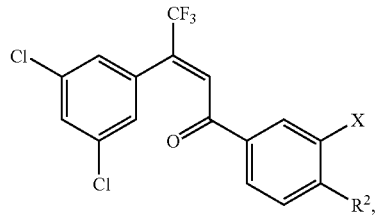 [2]-6
-continued
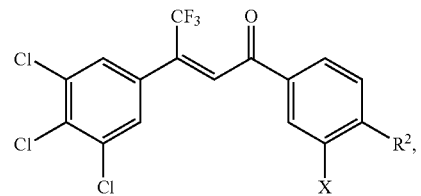 [2]-7
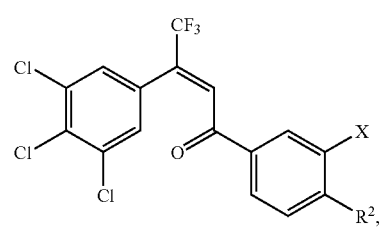 [2]-8
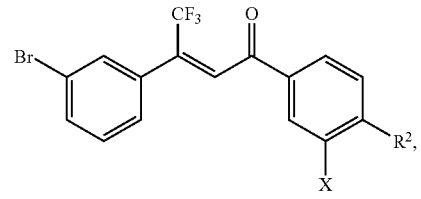 [2]-9
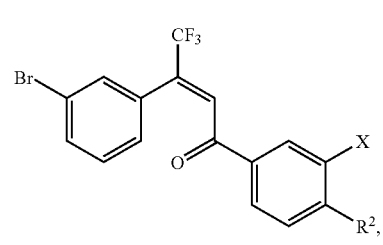 [2]-10
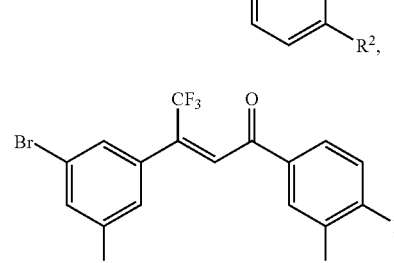 [2]-11
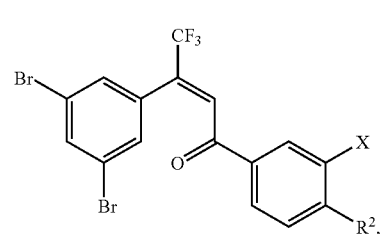 [2]-12
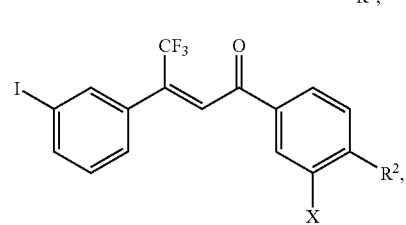 [2]-13

-continued
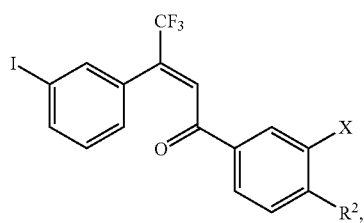 [2]-14
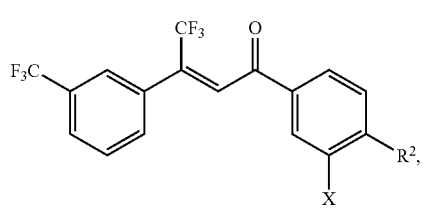 [2]-15
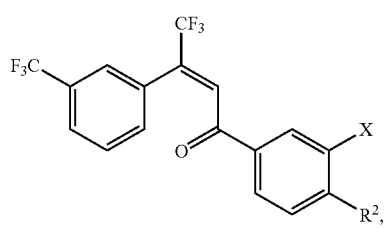 [2]-16
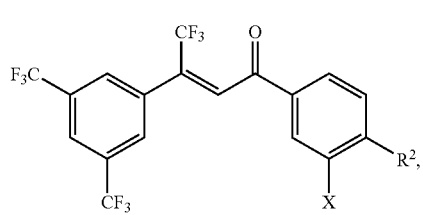 [2]-17
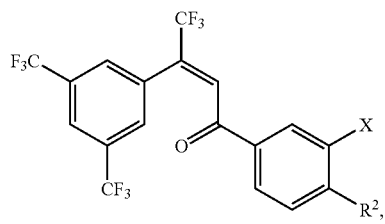 [2]-18
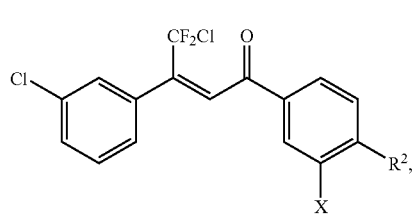 [2]-19
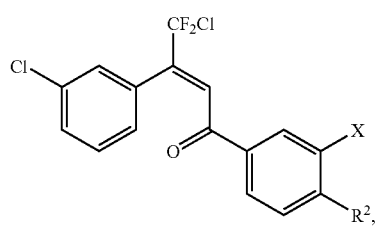 [2]-20
-continued
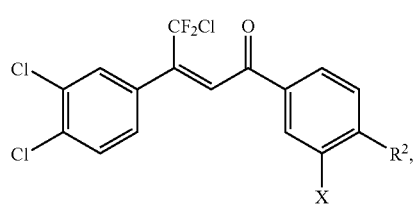 [2]-21
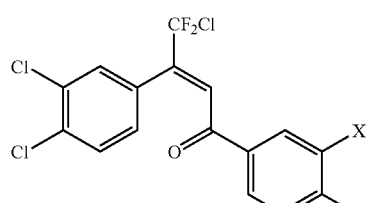 [2]-22
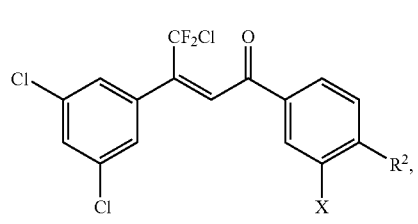 [2]-23
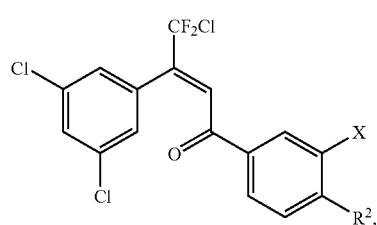 [2]-24
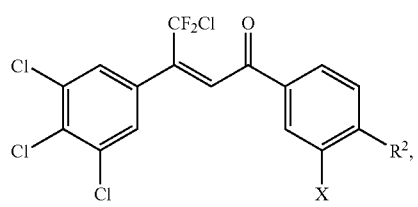 [2]-25
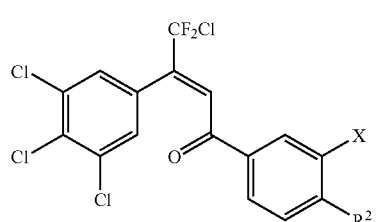 [2]-26
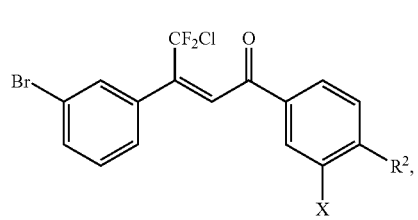 [2]-27

-continued

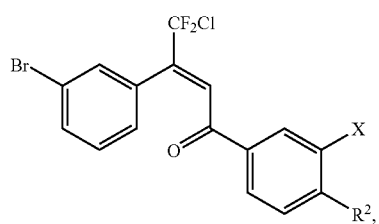
[2]-28

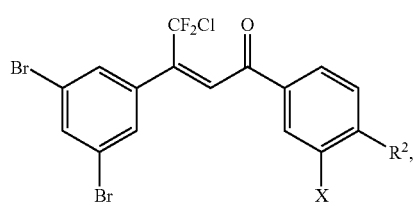
[2]-29

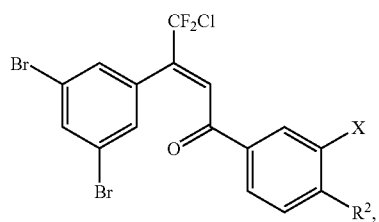
[2]-30

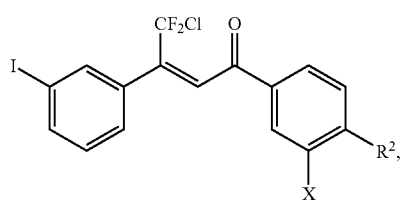
[2]-31

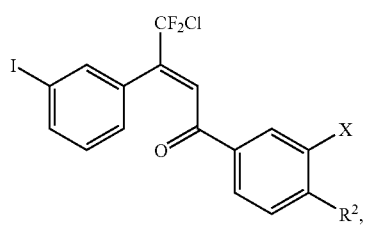
[2]-32

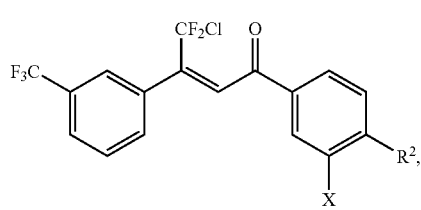
[2]-33

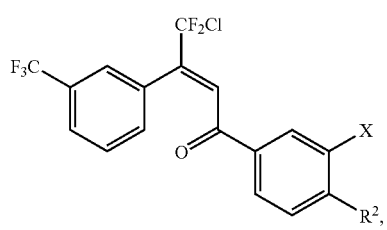
[2]-34

-continued

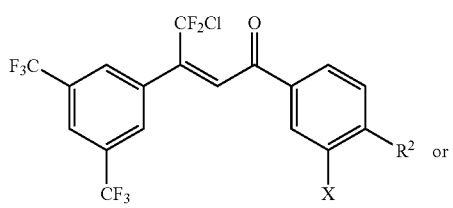
[2]-35 or

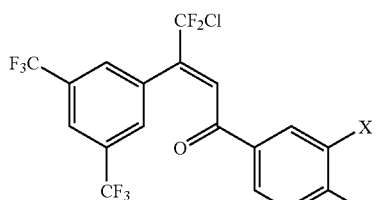
[2]-36

TABLE 1

The notation - denotes absence of substitution in the Tables.

| X | R² |
|---|---|
| (Table 1) | |
| — | F |
| — | Cl |
| — | Br |
| — | I |
| — | CN |
| — | NO₂ |
| — | NH₂ |
| — | NHC(O)CH₃ |
| — | NHC(O)OCH₃ |
| — | NHC(O)OEt |
| — | OH |
| — | OC(O)CH₃ |
| — | OCH₂Ph |
| — | OSO₂CH₃ |
| — | OSO₂CF₃ |
| — | OSO₂Ph |
| — | OSO₂(Ph-4-CH₃) |
| — | C(O)OH |
| — | C(O)OCH₃ |
| — | C(O)OEt |
| — | C(O)NH₂ |
| — | C(O)NHCH₂Pr-c |
| — | C(O)NHCH₂CF₃ |
| — | C(O)N(CH₂OCH₃)CH₂CF₃ |
| — | C(O)N(C(O)CH₃)CH₂CF₃ |
| (Table 2) | |
| — | C(O)N(C(O)OCH₃)CH₂CF₃ |
| — | C(O)NHCH₂CH=CH₂ |
| — | C(O)NHCH₂CH=CH |
| — | C(O)NHCH₂CN |
| — | C(O)NHCH₂OCH₂CF₃ |
| — | C(O)NHCH₂CH₂OCH₃ |
| — | C(O)NHCH₂CH₂OEt |
| — | C(O)NHCH=NOCH₃ |
| — | C(O)NHCH=NOEt |
| — | C(O)NHCH₂CH=NOH |
| — | C(O)NHCH₂CH=NOCH₃ |
| — | C(O)NHCH₂C(O)OH |
| — | C(O)NHCH₂C(O)OCH₃ |
| — | C(O)NHCH₂C(O)NH₂ |
| — | C(O)NHCH₂C(O)NHCH₂CH₂Cl |
| — | C(O)NHCH₂C(O)NHCH₂CH₂Br |
| — | C(O)NHCH₂C(O)NHCH₂CF₃ |
| — | C(O)NHCH₂C(O)NHCH₂CH₂OH |
| — | C(O)NHCH(CH₃)C(O)OH |
| — | C(O)NHCH(CH₃)C(O)OCH₃ |

TABLE 1-continued

The notation - denotes absence of substitution in the Tables.

| X | R² |
|---|---|
| — | C(O)NHCH(CH₃)C(O)NHCH₂CH₂Cl |
| — | C(O)NHCH(CH₃)C(O)NHCH₂CF₃ |
| — | C(O)NHPh |
| — | C(O)NH(Ph-4-F) |
| — | C(O)NH(Ph-4-CN) |
| — | C(O)NH(D-11a) |
| — | C(O)NH(D-38a) |
| — | C(O)NH(D-38d)Cl |
| | (Table 3) |
| — | C(O)NH(D-39e)Cl |
| — | C(O)NH(D-41a) |
| — | C(O)N(CH₃)(D-41a) |
| — | C(O)N(C(O)CH₃)(D-41a) |
| — | C(O)N(C(O)OCH₃)(D-41a) |
| — | C(O)NH(D-41c)Cl |
| — | C(O)N(CH₃)(D-41c)Cl |
| — | C(O)N(C(O)CH₃)(D-41c)Cl |
| — | C(O)N(C(O)OCH₃)(D-41c)Cl |
| — | C(O)NH(D-42a) |
| — | C(O)NH(D-44a) |
| — | C(O)NH(E-1a) |
| — | C(O)NHCH₂(D-11a) |
| — | C(O)NHCH₂(D-14a)CH₃ |
| — | C(O)NHCH₂(D-14b)Cl |
| — | C(O)NHCH₂(D-18a) |
| — | C(O)NHCH₂(D-19a) |
| — | C(O)N(C(O)CH₃)CH₂(D-19a) |
| — | C(O)N(C(O)Et)CH₂(D-19a) |
| — | C(O)N(C(O)OCH₃)CH₂(D-19a) |
| — | C(O)NHCH₂(D-25a) |
| — | C(O)NHCH₂(D-27a) |
| — | C(O)NHCH₂(D-28a) |
| — | C(O)NHCH₂(D-31a) |
| — | C(O)NHCH₂(D-34a) |
| — | C(O)NHCH₂(D-36a) |
| — | C(O)NHCH₂(D-38a) |
| — | C(O)N(CH₂CN)CH₂(D-38a) |
| | (Table 4) |
| — | C(O)N(CH₂OCH₃)CH₂(D-38a) |
| — | C(O)N(C(O)CH₃)CH₂(D-38a) |
| — | C(O)N(C(O)Et)CH₂(D-38a) |
| — | C(O)N(C(O)OCH₃)CH₂(D-38a) |
| — | C(O)NHCH₂(D-40a) |
| — | C(O)NHCH₂(D-41a) |
| — | C(O)NHCH₂(D-42a) |
| — | C(O)NHCH₂(D-44a) |
| — | C(O)NHCH₂(E-1a) |
| — | C(O)NHC(O)OCH₃ |
| — | C(O)N(CH₃)C(O)OCH₃ |
| — | C(O)N(Et)C(O)OCH₃ |
| — | C(O)N(CH₂CN)C(O)OCH₃ |
| — | C(O)N(CH₂OCH₃)C(O)OCH₃ |
| — | C(O)N(C(O)Et)C(O)OCH₃ |
| — | C(O)N(C(O)Pr-n)C(O)OCH₃ |
| — | C(O)N(C(O)Pr-i)C(O)OCH₃ |
| — | C(O)N(C(O)OCH₃)C(O)OCH₃ |
| — | C(O)NHC(O)OEt |
| — | C(O)N(CH₃)C(O)OEt |
| — | C(O)N(Et)C(O)OEt |
| — | C(O)N(CH₂CN)C(O)OEt |
| — | C(O)N(CH₂OCH₃)C(O)OEt |
| — | C(O)N(C(O)CH₃)C(O)OEt |
| — | C(O)N(C(O)Et)C(O)OEt |
| — | C(O)N(C(O)Pr-n)C(O)OEt |
| — | C(O)N(C(O)Pr-i)C(O)OEt |
| — | C(O)N(C(O)OCH₃)C(O)OEt |
| | (Table 5) |
| — | C(O)NHC(O)OPr-i |
| — | C(O)N(CH₃)C(O)OPr-i |
| — | C(O)N(Et)C(O)OPr-i |
| — | C(O)N(CH₂CN)C(O)OPr-i |
| — | C(O)N(CH₂OCH₃)C(O)OPr-i |
| — | C(O)N(C(O)CH₃)C(O)OPr-i |
| — | C(O)N(C(O)Et)C(O)OPr-i |
| — | C(O)N(C(O)Pr-n)C(O)OPr-i |
| — | C(O)N(C(O)Pr-i)C(O)OPr-i |
| — | C(O)N(C(O)OCH₃)C(O)OPr-i |
| — | C(O)N(C(O)OEt)C(O)OPr-i |
| — | C(O)NHC(O)NH₂ |
| — | C(O)NHN(CH₃)Ph |
| — | C(O)N(C(O)CH₃)N(CH₃)Ph |
| — | C(O)N(C(O)OCH₃)N(CH₃)Ph |
| — | C(O)NHN(CH₃)(D-41a) |
| — | C(O)N(C(O)CH₃)N(CH₃)(D-41a) |
| — | C(O)N(C(O)OCH₃)N(CH₃)(D-41a) |
| NO₂ | Cl |
| NO₂ | Br |
| NO₂ | I |
| NO₂ | CN |
| NO₂ | NH₂ |
| NO₂ | NHC(O)CH₃ |
| NO₂ | NHC(O)OCH₃ |
| NO₂ | NHC(O)OEt |
| NO₂ | OH |
| NO₂ | OC(O)CH₃ |
| | (Table 6) |
| NO₂ | OCH₂Ph |
| NO₂ | OSO₂CH₃ |
| NO₂ | OSO₂CF₃ |
| NO₂ | OSO₂Ph |
| NO₂ | OSO₂(Ph-4-CH₃) |
| NO₂ | C(O)OH |
| NO₂ | C(O)OCH₃ |
| NO₂ | C(O)OEt |
| NO₂ | C(O)NH₂ |
| NO₂ | C(O)NHCH₂Pr-c |
| NO₂ | C(O)NHCH₂CF₃ |
| NO₂ | C(O)N(CH₂OCH₃)CH₂CF₃ |
| NO₂ | C(O)N(C(O)CH₃)CH₂CF₃ |
| NO₂ | C(O)N(C(O)OCH₃)CH₂CF₃ |
| NO₂ | C(O)NHCH₂CH=CH₂ |
| NO₂ | C(O)NHCH₂CH≡CH |
| NO₂ | C(O)NHCH₂CN |
| NO₂ | C(O)NHCH₂OCH₂CF₃ |
| NO₂ | C(O)NHCH₂CH₂OCH₃ |
| NO₂ | C(O)NHCH₂CH₂OEt |
| NO₂ | C(O)NHCH=NOCH₃ |
| NO₂ | C(O)NHCH=NOEt |
| NO₂ | C(O)NHCH₂CH=NOH |
| NO₂ | C(O)NHCH₂CH=NOCH₃ |
| NO₂ | C(O)NHCH₂C(O)OH |
| NO₂ | C(O)NHCH₂C(O)OCH₃ |
| NO₂ | C(O)NHCH₂C(O)NH₂ |
| NO₂ | C(O)NHCH₂C(O)NHCH₂CH₂Cl |
| | (Table 7) |
| NO₂ | C(O)NHCH₂C(O)NHCH₂Br |
| NO₂ | C(O)NHCH₂C(O)NHCH₂CF₃ |
| NO₂ | C(O)NHCH₂C(O)NHCH₂OH |
| NO₂ | C(O)NHCH(CH₃)C(O)OH |
| NO₂ | C(O)NHCH(CH₃)C(O)OCH₃ |
| NO₂ | C(O)NHCH(CH₃)C(O)NHCH₂CH₂Cl |
| NO₂ | C(O)NHCH(CH₃)C(O)NHCH₂CF₃ |
| NO₂ | C(O)NHPh |
| NO₂ | C(O)NH(Ph-4-F) |
| NO₂ | C(O)NH(Ph-4-CN) |
| NO₂ | C(O)NH(D-11a) |
| NO₂ | C(O)NH(D-38a) |
| NO₂ | C(O)NH(D-38d)Cl |
| NO₂ | C(O)NH(D-39e)Cl |
| NO₂ | C(O)NH(D-41a) |
| NO₂ | C(O)N(CH₃)(D-41a) |
| NO₂ | C(O)N(C(O)CH₃)(D-41a) |
| NO₂ | C(O)N(C(O)OCH₃)(D-41a) |
| NO₂ | C(O)NH(D-41c)Cl |
| NO₂ | C(O)N(CH₃)(D-41c)Cl |

TABLE 1-continued

The notation - denotes absence of substitution in the Tables.

| X | R² |
|---|---|
| NO₂ | C(O)N(C(O)CH₃)(D-41c)Cl |
| NO₂ | C(O)N(C(O)OCH₃)(D-41c)Cl |
| NO₂ | C(O)NH(D-42a) |
| NO₂ | C(O)NH(D-44a) |
| NO₂ | C(O)NH(E-1a) |
| NO₂ | C(O)NHCH₂(D-11a) |
| NO₂ | C(O)NHCH₂(D-14a)CH₃ |
| NO₂ | C(O)NHCH₂(D-14b)Cl |

(Table 8)

| X | R² |
|---|---|
| NO₂ | C(O)NHCH₂(D-18a) |
| NO₂ | C(O)NHCH₂(D-19a) |
| NO₂ | C(O)N(C(O)CH₃)CH₂(D-19a) |
| NO₂ | C(O)N(C(O)Et)CH₂(D-19a) |
| NO₂ | C(O)N(C(O)OCH₃)CH₂(D-19a) |
| NO₂ | C(O)NHCH₂(D-25a) |
| NO₂ | C(O)NHCH₂(D-27a) |
| NO₂ | C(O)NHCH₂(D-28a) |
| NO₂ | C(O)NHCH₂(D-31a) |
| NO₂ | C(O)NHCH₂(D-34a) |
| NO₂ | C(O)NHCH₂(D-36a) |
| NO₂ | C(O)NHCH₂(D-38a) |
| NO₂ | C(O)N(CH₂CN)CH₂(D-38a) |
| NO₂ | C(O)N(CH₂OCH₃)CH₂(D-38a) |
| NO₂ | C(O)N(C(O)CH₃)CH₂(D-38a) |
| NO₂ | C(O)N(C(O)Et)CH₂(D-38a) |
| NO₂ | C(O)N(C(O)OCH₃)CH₂(D-38a) |
| NO₂ | C(O)NHCH₂(D-40a) |
| NO₂ | C(O)NHCH₂(D-41a) |
| NO₂ | C(O)NHCH₂(D-42a) |
| NO₂ | C(O)NHCH₂(D-44a) |
| NO₂ | C(O)NHCH₂(E-1a) |
| NO₂ | C(O)NHCH₂(E-3a) |
| NO₂ | C(O)NHCH₂(E-5a) |
| NO₂ | C(O)NHC(O)OCH₃ |
| NO₂ | C(O)N(CH₃)C(O)OCH₃ |
| NO₂ | C(O)N(Et)C(O)OCH₃ |
| NO₂ | C(O)N(CH₂CN)C(O)OCH₃ |

(Table 9)

| X | R² |
|---|---|
| NO₂ | C(O)N(CH₂OCH₃)C(O)OCH₃ |
| NO₂ | C(O)N(C(O)Et)C(O)OCH₃ |
| NO₂ | C(O)N(C(O)Pr-n)C(O)OCH₃ |
| NO₂ | C(O)N(C(O)Pr-i)C(O)OCH₃ |
| NO₂ | C(O)N(C(O)OCH₃)C(O)OCH₃ |
| NO₂ | C(O)NHC(O)OEt |
| NO₂ | C(O)N(CH₃)C(O)OEt |
| NO₂ | C(O)N(Et)C(O)OEt |
| NO₂ | C(O)N(CH₂CN)C(O)OEt |
| NO₂ | C(O)N(CH₂OCH₃)C(O)OEt |
| NO₂ | C(O)N(C(O)CH₃)C(O)OEt |
| NO₂ | C(O)N(C(O)Et)C(O)OEt |
| NO₂ | C(O)N(C(O)Pr-n)C(O)OEt |
| NO₂ | C(O)N(C(O)Pr-i)C(O)OEt |
| NO₂ | C(O)N(C(O)OCH₃)C(O)OEt |
| NO₂ | C(O)NHC(O)OPr-i |
| NO₂ | C(O)N(CH₃)C(O)OPr-i |
| NO₂ | C(O)N(Et)C(O)OPr-i |
| NO₂ | C(O)N(CH₂CN)C(O)OPr-i |
| NO₂ | C(O)N(CH₂OCH₃)C(O)OPr-i |
| NO₂ | C(O)N(C(O)CH₃)C(O)OPr-i |
| NO₂ | C(O)N(C(O)Et)C(O)OPr-i |
| NO₂ | C(O)N(C(O)Pr-n)C(O)OPr-i |
| NO₂ | C(O)N(C(O)Pr-i)C(O)OPr-i |
| NO₂ | C(O)N(C(O)OCH₃)C(O)OPr-i |
| NO₂ | C(O)N(C(O)OEt)C(O)OPr-i |
| NO₂ | C(O)NHC(O)NH₂ |
| NO₂ | C(O)NHN(CH₃)Ph |

(Table 10)

| X | R² |
|---|---|
| NO₂ | C(O)N(C(O)CH₃)N(CH₃)Ph |
| NO₂ | C(O)N(C(O)OCH₃)N(CH₃)Ph |
| NO₂ | C(O)NHN(CH₃)(D-41a) |
| NO₂ | C(O)N(C(O)CH₃)N(CH₃)(D-41a) |
| NO₂ | C(O)N(C(O)OCH₃)N(CH₃)(D-41a) |

| X | R² |
|---|---|
| CH₃ | F |
| CH₃ | Cl |
| CH₃ | Br |
| CH₃ | I |
| CH₃ | CN |
| CH₃ | NO₂ |
| CH₃ | NH₂ |
| CH₃ | NHC(O)CH₃ |
| CH₃ | NHC(O)OCH₃ |
| CH₃ | NHC(O)OEt |
| CH₃ | OH |
| CH₃ | OC(O)CH₃ |
| CH₃ | OCH₂Ph |
| CH₃ | OSO₂CH₃ |
| CH₃ | OSO₂CF₃ |
| CH₃ | OSO₂Ph |
| CH₃ | OSO₂(Ph-4-CH₃) |
| CH₃ | C(O)OH |
| CH₃ | C(O)OCH₃ |
| CH₃ | C(O)OEt |
| CH₃ | C(O)NH₂ |
| CH₃ | C(O)NHCH₃ |
| CH₃ | C(O)NHEt |

(Table 11)

| X | R² |
|---|---|
| CH₃ | C(O)NHCH₂Pr-c |
| CH₃ | C(O)N(CH₃)CH₂Pr-c |
| CH₃ | C(O)N(C(O)CH₃)CH₂Pr-c |
| CH₃ | C(O)N(C(O)OCH₃)CH₂Pr-c |
| CH₃ | C(O)NHCH₂CF₃ |
| CH₃ | C(O)N(CH₃)CH₂CF₃ |
| CH₃ | C(O)N(Et)CH₂CF₃ |
| CH₃ | C(O)N(CH₂OCH₃)CH₂CF₃ |
| CH₃ | C(O)N(C(O)CH₃)CH₂CF₃ |
| CH₃ | C(O)N(C(O)OCH₃)CH₂CF₃ |
| CH₃ | C(O)NHCH₂CH=CH₂ |
| CH₃ | C(O)NHCH₂CH=CH |
| CH₃ | C(O)NHCH₂OCH₂CF₃ |
| CH₃ | C(O)NHCH₂CH₂OCH₃ |
| CH₃ | C(O)NHCH₂CH₂OEt |
| CH₃ | C(O)NHCH=NOCH₃ |
| CH₃ | C(O)NHC(CH₃)=NOCH₃ |
| CH₃ | C(O)NHCH=NOEt |
| CH₃ | C(O)NHCH₂CH=NOH |
| CH₃ | C(O)NHCH₂CH=NOCH₃ |
| CH₃ | C(O)NHCH₂C(CH₃)=CNOCH₃ |
| CH₃ | C(O)NHCH₂CN |
| CH₃ | C(O)NHCH(CN)OCH₂CF₃ |
| CH₃ | C(O)NHCH₂C(O)OH |
| CH₃ | C(O)NHCH₂C(O)OCH₃ |
| CH₃ | C(O)NHCH₂C(O)OEt |
| CH₃ | C(O)NHCH₂C(O)OCH₂CF₃ |
| CH₃ | C(O)NHCH₂C(O)NH₂ |

(Table 12)

| X | R² |
|---|---|
| CH₃ | C(O)NHCH₂C(O)NHCH₃ |
| CH₃ | C(O)NHCH₂C(O)N(CH₃)₂ |
| CH₃ | C(O)NHCH₂C(O)NHEt |
| CH₃ | C(O)NHCH₂C(O)NHCH₂CH₂Cl |
| CH₃ | C(O)NHCH₂C(O)N(CH₃)CH₂CH₂Cl |
| CH₃ | C(O)N(CH₃)CH₂C(O)NHCH₂CH₂Cl |
| CH₃ | C(O)N(C(O)CH₃)CH₂C(O)NHCH₂CH₂Cl |
| CH₃ | C(O)N(C(O)OCH₃)CH₂C(O)NHCH₂CH₂Cl |
| CH₃ | C(O)NHCH₂C(O)NHCH₂CH₂Br |
| CH₃ | C(O)NHCH₂C(O)NHCH₂CF₃ |
| CH₃ | C(O)NHCH₂C(O)N(CH₃)CH₂CF₃ |
| CH₃ | C(O)N(CH₃)CH₂C(O)NHCH₂CF₃ |
| CH₃ | C(O)N(C(O)CH₃)CH₂C(O)NHCH₂CF₃ |
| CH₃ | C(O)N(C(O)OCH₃)CH₂C(O)NHCH₂CF₃ |
| CH₃ | C(O)NHCH₂C(O)NHCH₂CH₂OH |
| CH₃ | C(O)NHCH(CH₃)C(O)OH |
| CH₃ | C(O)NHCH(CH₃)C(O)OCH₃ |
| CH₃ | C(O)NHCH(CH₃)C(O)NHCH₂CH₂Cl |
| CH₃ | C(O)NHCH(CH₃)C(O)NHCH₂CF₃ |
| CH₃ | C(O)NHCH₂(E-1a) |

TABLE 1-continued

The notation - denotes absence of substitution in the Tables.

| X | $R^2$ |
|---|---|
| $CH_3$ | $C(O)NHCH_2$(E-2a) |
| $CH_3$ | $C(O)NHCH_2$(E-3a) |
| $CH_3$ | $C(O)NHCH_2$(E-5a) |
| $CH_3$ | $C(O)NHCH_2$(E-7a) |
| $CH_3$ | $C(O)NHPh$ |
| $CH_3$ | $C(O)NH(Ph-4-F)$ |
| $CH_3$ | $C(O)N(CH_3)(Ph-4-F)$ |
| $CH_3$ | $C(O)N(Et)(Ph-4-F)$ |

(Table 13)

| X | $R^2$ |
|---|---|
| $CH_3$ | $C(O)N(CH_2CH{=}CH_2)(Ph-4-F)$ |
| $CH_3$ | $C(O)N(CH_2CN)(Ph-4-F)$ |
| $CH_3$ | $C(O)N(CH_2OCH_3)(Ph-4-F)$ |
| $CH_3$ | $C(O)N(C(O)CH_3)(Ph-4-F)$ |
| $CH_3$ | $C(O)N(C(O)OCH_3)(Ph-4-F)$ |
| $CH_3$ | $C(O)NH(Ph-4-CN)$ |
| $CH_3$ | $C(O)N(CH_3)(Ph-4-CN)$ |
| $CH_3$ | $C(O)N(C(O)CH_3)(Ph-4-CN)$ |
| $CH_3$ | $C(O)N(C(O)OCH_3)(Ph-4-CN)$ |
| $CH_3$ | $C(O)NH(Ph-4-NO_2)$ |
| $CH_3$ | $C(O)NH(D-5a)$ |
| $CH_3$ | $C(O)NH(D-5b)CH_3$ |
| $CH_3$ | $C(O)NH(D-10b)CH_3$ |
| $CH_3$ | $C(O)NH(D-11a)$ |
| $CH_3$ | $C(O)N(CH_3)(D-11a)$ |
| $CH_3$ | $C(O)N(C(O)CH_3)(D-11a)$ |
| $CH_3$ | $C(O)N(C(O)OCH_3)(D-11a)$ |
| $CH_3$ | $C(O)NH(D-12a)CH_3$ |
| $CH_3$ | $C(O)NH(D-18a)$ |
| $CH_3$ | $C(O)NH(D-32a)$ |
| $CH_3$ | $C(O)NH(D-38a)$ |
| $CH_3$ | $C(O)N(CH_3)(D-38a)$ |
| $CH_3$ | $C(O)N(C(O)CH_3)(D-38a)$ |
| $CH_3$ | $C(O)N(C(O)OCH_3)(D-38a)$ |
| $CH_3$ | $C(O)NH(D-38d)Cl$ |
| $CH_3$ | $C(O)NH(D-39e)Cl$ |
| $CH_3$ | $C(O)N(CH_3)(D-39e)Cl$ |
| $CH_3$ | $C(O)N(C(O)CH_3)(D-39e)Cl$ |

(Table 14)

| X | $R^2$ |
|---|---|
| $CH_3$ | $C(O)N(C(O)OCH_3)(D-39e)Cl$ |
| $CH_3$ | $C(O)NH(D-41a)$ |
| $CH_3$ | $C(O)N(CH_3)(D-41a)$ |
| $CH_3$ | $C(O)N(C(O)CH_3)(D-41a)$ |
| $CH_3$ | $C(O)N(C(O)OCH_3)(D-41a)$ |
| $CH_3$ | $C(O)NH(D-41b)CH_3$ |
| $CH_3$ | $C(O)NH(D-41c)Cl$ |
| $CH_3$ | $C(O)N(CH_3)(D-41c)Cl$ |
| $CH_3$ | $C(O)N(C(O)CH_3)(D-41c)Cl$ |
| $CH_3$ | $C(O)N(C(O)OCH_3)(D-41c)Cl$ |
| $CH_3$ | $C(O)NH(D-41c)Br$ |
| $CH_3$ | $C(O)N(C(O)CH_3)(D-41c)Br$ |
| $CH_3$ | $C(O)N(C(O)OCH_3)(D-41c)Br$ |
| $CH_3$ | $C(O)NH(D-42a)$ |
| $CH_3$ | $C(O)NH(D-44a)$ |
| $CH_3$ | $C(O)NH(E-1a)$ |
| $CH_3$ | $C(O)NHCH_2Ph$ |
| $CH_3$ | $C(O)NHCH(CH_3)Ph$ |
| $CH_3$ | $C(O)NHCH(CF_3)Ph$ |
| $CH_3$ | $C(O)NHCH(CN)Ph$ |
| $CH_3$ | $C(O)NHCH_2(Ph-4-NO_2)$ |
| $CH_3$ | $C(O)NHCH_2(D-8a)$ |
| $CH_3$ | $C(O)NHCH_2(D-11a)$ |
| $CH_3$ | $C(O)NHCH(CN)(D-11a)$ |
| $CH_3$ | $C(O)NHCH_2(D-12a)CH_3$ |
| $CH_3$ | $C(O)NHCH_2(D-13b)Cl$ |
| $CH_3$ | $C(O)NHCH_2(D-13c)Cl$ |
| $CH_3$ | $C(O)NHCH_2(D-14a)CH_3$ |

(Table 15)

| X | $R^2$ |
|---|---|
| $CH_3$ | $C(O)NHCH_2(D-14b)Cl$ |
| $CH_3$ | $C(O)NHCH_2(D-18a)$ |
| $CH_3$ | $C(O)NHCH_2(D-19a)$ |
| $CH_3$ | $C(O)N(CH_3)CH_2(D-19a)$ |
| $CH_3$ | $C(O)N(C(O)CH_3)CH_2(D-19a)$ |
| $CH_3$ | $C(O)N(C(O)Et)CH_2(D-19a)$ |
| $CH_3$ | $C(O)N(C(O)OCH_3)CH_2(D-19a)$ |
| $CH_3$ | $C(O)NHCH_2(D-20a)$ |
| $CH_3$ | $C(O)NHCH_2(D-22a)CH_3$ |
| $CH_3$ | $C(O)NHCH_2(D-24a)CH_3$ |
| $CH_3$ | $C(O)NHCH_2(D-25a)$ |
| $CH_3$ | $C(O)NHCH_2(D-27a)$ |
| $CH_3$ | $C(O)NHCH_2(D-28a)$ |
| $CH_3$ | $C(O)NHCH_2(D-31a)$ |
| $CH_3$ | $C(O)NHCH_2(D-34a)$ |
| $CH_3$ | $C(O)NHCH_2(D-36a)$ |
| $CH_3$ | $C(O)NHCH(CN)(D-36a)$ |
| $CH_3$ | $C(O)NHCH_2(D-38a)$ |
| $CH_3$ | $C(O)NHCH(CH_3)(D-38a)$ |
| $CH_3$ | $C(O)NHCH(CF_3)(D-38a)$ |
| $CH_3$ | $C(O)NHCH(CN)(D-38a)$ |
| $CH_3$ | $C(O)N(CH_3)CH_2(D-38a)$ |
| $CH_3$ | $C(O)N(CH_2C{\equiv}CH)CH_2(D-38a)$ |
| $CH_3$ | $C(O)N(CH_2CN)CH_2(D-38a)$ |
| $CH_3$ | $C(O)N(CH_2OCH_3)CH_2(D-38a)$ |
| $CH_3$ | $C(O)N(C(O)CH_3)CH_2(D-38a)$ |
| $CH_3$ | $C(O)N(C(O)Et)CH_2(D-38a)$ |
| $CH_3$ | $C(O)N(C(O)OCH_3)CH_2(D-38a)$ |

(Table 16)

| X | $R^2$ |
|---|---|
| $CH_3$ | $C(O)NHCH_2(D-40a)$ |
| $CH_3$ | $C(O)NHCH_2(D-41a)$ |
| $CH_3$ | $C(O)NHCH_2(D-42a)$ |
| $CH_3$ | $C(O)NHCH_2(D-44a)$ |
| $CH_3$ | $C(O)NHC(O)OCH_3$ |
| $CH_3$ | $C(O)N(CH_3)C(O)OCH_3$ |
| $CH_3$ | $C(O)N(Et)C(O)OCH_3$ |
| $CH_3$ | $C(O)N(CH_2CN)C(O)OCH_3$ |
| $CH_3$ | $C(O)N(CH_2OCH_3)C(O)OCH_3$ |
| $CH_3$ | $C(O)N(C(O)CH_3)C(O)OCH_3$ |
| $CH_3$ | $C(O)N(C(O)Et)C(O)OCH_3$ |
| $CH_3$ | $C(O)N(C(O)Pr-n)C(O)OCH_3$ |
| $CH_3$ | $C(O)N(C(O)Pr-i)C(O)OCH_3$ |
| $CH_3$ | $C(O)N(C(O)OCH_3)C(O)OCH_3$ |
| $CH_3$ | $C(O)NHC(O)OEt$ |
| $CH_3$ | $C(O)N(CH_3)C(O)OEt$ |
| $CH_3$ | $C(O)N(Et)C(O)OEt$ |
| $CH_3$ | $C(O)N(CH_2CN)C(O)OEt$ |
| $CH_3$ | $C(O)N(CH_2OCH_3)C(O)OEt$ |
| $CH_3$ | $C(O)N(C(O)CH_3)C(O)OEt$ |
| $CH_3$ | $C(O)N(C(O)Et)C(O)OEt$ |
| $CH_3$ | $C(O)N(C(O)Pr-n)C(O)OEt$ |
| $CH_3$ | $C(O)N(C(O)Pr-i)C(O)OEt$ |
| $CH_3$ | $C(O)N(C(O)OCH_3)C(O)OEt$ |
| $CH_3$ | $C(O)NHC(O)OPr-i$ |
| $CH_3$ | $C(O)N(CH_3)C(O)OPr-i$ |
| $CH_3$ | $C(O)N(Et)C(O)OPr-i$ |
| $CH_3$ | $C(O)N(CH_2CN)C(O)OPr-i$ |

(Table 17)

| X | $R^2$ |
|---|---|
| $CH_3$ | $C(O)N(CH_2OCH_3)C(O)OPr-i$ |
| $CH_3$ | $C(O)N(C(O)CH_3)C(O)OPr-i$ |
| $CH_3$ | $C(O)N(C(O)Et)C(O)OPr-i$ |
| $CH_3$ | $C(O)N(C(O)Pr-n)C(O)OPr-i$ |
| $CH_3$ | $C(O)N(C(O)Pr-i)C(O)OPr-i$ |
| $CH_3$ | $C(O)N(C(O)OCH_3)C(O)OPr-i$ |
| $CH_3$ | $C(O)N(C(O)OEt)C(O)OPr-i$ |
| $CH_3$ | $C(O)NHC(O)NH_2$ |
| $CH_3$ | $C(O)NHC(O)NHCH_3$ |
| $CH_3$ | $C(O)NHNH_2$ |
| $CH_3$ | $C(O)NHNHPh$ |
| $CH_3$ | $C(O)NHN(CH_3)Ph$ |
| $CH_3$ | $C(O)N(CH_3)NHPh$ |
| $CH_3$ | $C(O)N(CH_3)N(CH_3)Ph$ |
| $CH_3$ | $C(O)N(C(O)CH_3)N(CH_3)Ph$ |
| $CH_3$ | $C(O)N(C(O)OCH_3)N(CH_3)Ph$ |
| $CH_3$ | $C(O)NHNH(D-41a)$ |
| $CH_3$ | $C(O)NHN(CH_3)(D-41a)$ |
| $CH_3$ | $C(O)N(CH_3)N(CH_3)(D-41a)$ |
| $CH_3$ | $C(O)N(C(O)CH_3)N(CH_3)(D-41a)$ |

TABLE 1-continued

The notation - denotes absence of substitution in the Tables.

| X | R² |
|---|---|
| CH₃ | C(O)N(C(O)OCH₃)N(CH₃)(D-41a) |
| Et | F |
| Et | Cl |
| Et | Br |
| Et | I |
| Et | NO₂ |
| Et | NH₂ |
| Et | NHC(O)CH₃ |

(Table 18)

| X | R² |
|---|---|
| Et | NHC(O)OCH₃ |
| Et | NHC(O)OEt |
| Et | OH |
| Et | OC(O)CH₃ |
| Et | OCH₂Ph |
| Et | OSO₂CH₃ |
| Et | OSO₂CF₃ |
| Et | OSO₂Ph |
| Et | OSO₂(Ph-4-CH₃) |
| Et | C(O)OH |
| Et | C(O)OCH₃ |
| Et | C(O)OEt |
| Et | C(O)NH₂ |
| Et | C(O)NHCH₂Pr-c |
| Et | C(O)NHCH₂CF₃ |
| Et | C(O)NHCH₂CH═CH₂ |
| Et | C(O)NHCH₂CH═CH |
| Et | C(O)NHCH₂CN |
| Et | C(O)NHCH₂OCH₂CF₃ |
| Et | C(O)NHCH₂CH₂OCH₃ |
| Et | C(O)NHCH₂CH₂OEt |
| Et | C(O)NHCH═NOCH₃ |
| Et | C(O)NHCH═NOEt |
| Et | C(O)NHCH₂CH═NOH |
| Et | C(O)NHCH₂CH═NOCH₃ |
| Et | C(O)NHCH₂C(O)OH |
| Et | C(O)NHCH₂C(O)OCH₃ |
| Et | C(O)NHCH₂C(O)OEt |

(Table 19)

| X | R² |
|---|---|
| Et | C(O)NHCH₂C(O)NH₂ |
| Et | C(O)NHCH₂C(O)NHCH₂CF₃ |
| Et | C(O)NHCH(CH₃)C(O)OH |
| Et | C(O)NHCH(CH₃)C(O)OCH₃ |
| Et | C(O)NHCH(CH₃)C(O)NHCH₂CF₃ |
| Et | C(O)NH(D-11a) |
| Et | C(O)NH(D-38a) |
| Et | C(O)NH(D-38d)Cl |
| Et | C(O)NH(D-39e)Cl |
| Et | C(O)NH(D-41a) |
| Et | C(O)N(C(O)CH₃)(D-41a) |
| Et | C(O)N(C(O)OCH₃)(D-41a) |
| Et | C(O)NH(D-41c)Cl |
| Et | C(O)N(C(O)CH₃)(D-41c)Cl |
| Et | C(O)N(C(O)OCH₃)(D-41c)Cl |
| Et | C(O)NH(D-42a) |
| Et | C(O)NH(D-44a) |
| Et | C(O)NH(E-1a) |
| Et | C(O)NHCH₂(D-11a) |
| Et | C(O)NHCH₂(D-14a)CH₃ |
| Et | C(O)NHCH₂(D-14b)Cl |
| Et | C(O)NHCH₂(D-18a) |
| Et | C(O)NHCH₂(D-19a) |
| Et | C(O)N(C(O)CH₃)CH₂(D-19a) |
| Et | C(O)N(C(O)Et)CH₂(D-19a) |
| Et | C(O)N(C(O)OCH₃)CH₂(D-19a) |
| Et | C(O)NHCH₂(D-25a) |
| Et | C(O)NHCH₂(D-27a) |

(Table 20)

| X | R² |
|---|---|
| Et | C(O)NHCH₂(D-28a) |
| Et | C(O)NHCH₂(D-31a) |
| Et | C(O)NHCH₂(D-34a) |
| Et | C(O)NHCH₂(D-36a) |
| Et | C(O)NHCH₂(D-38a) |
| Et | C(O)N(CH₂OCH₃)CH₂(D-38a) |
| Et | C(O)N(C(O)CH₃)CH₂(D-38a) |
| Et | C(O)N(C(O)Et)CH₂(D-38a) |
| Et | C(O)N(C(O)OCH₃)CH₂(D-38a) |
| Et | C(O)NHCH₂(D-40a) |
| Et | C(O)NHCH₂(D-41a) |
| Et | C(O)NHCH₂(D-42a) |
| Et | C(O)NHCH₂(D-44a) |
| Et | C(O)NHCH₂(E-1a) |
| Et | C(O)NHCH₂(E-3a) |
| Et | C(O)NHCH₂(E-5a) |
| Et | C(O)NHC(O)OCH₃ |
| Et | C(O)N(CH₃)C(O)OCH₃ |
| Et | C(O)N(Et)C(O)OCH₃ |
| Et | C(O)N(CH₂OCH₃)C(O)OCH₃ |
| Et | C(O)N(C(O)Et)C(O)OCH₃ |
| Et | C(O)N(C(O)Pr-n)C(O)OCH₃ |
| Et | C(O)N(C(O)Pr-i)C(O)OCH₃ |
| Et | C(O)N(C(O)OCH₃)C(O)OCH₃ |
| Et | C(O)NHC(O)OEt |
| Et | C(O)N(CH₃)C(O)OEt |
| Et | C(O)N(Et)C(O)OEt |
| Et | C(O)N(CH₂OCH₃)C(O)OEt |

(Table 21)

| X | R² |
|---|---|
| Et | C(O)N(C(O)CH₃)C(O)OEt |
| Et | C(O)N(C(O)Et)C(O)OEt |
| Et | C(O)N(C(O)Pr-n)C(O)OEt |
| Et | C(O)N(C(O)Pr-i)C(O)OEt |
| Et | C(O)N(C(O)OCH₃)C(O)OEt |
| Et | C(O)NHC(O)OPr-i |
| Et | C(O)N(CH₃)C(O)OPr-i |
| Et | C(O)N(Et)C(O)OPr-i |
| Et | C(O)N(CH₂OCH₃)C(O)OPr-i |
| Et | C(O)N(C(O)CH₃)C(O)OPr-i |
| Et | C(O)N(C(O)Et)C(O)OPr-i |
| Et | C(O)N(C(O)Pr-n)C(O)OPr-i |
| Et | C(O)N(C(O)Pr-i)C(O)OPr-i |
| Et | C(O)N(C(O)OCH₃)C(O)OPr-i |
| Et | C(O)N(C(O)OEt)C(O)OPr-i |
| Et | C(O)NHC(O)NH₂ |
| Et | C(O)NHN(CH₃)Ph |
| Et | C(O)N(C(O)CH₃)N(CH₃)Ph |
| Et | C(O)N(C(O)OCH₃)N(CH₃)Ph |
| Et | C(O)NHN(CH₃)(D-41a) |
| Et | C(O)N(C(O)CH₃)N(CH₃)(D-41a) |
| Et | C(O)N(C(O)OCH₃)N(CH₃)(D-41a) |
| CF₃ | F |
| CF₃ | Cl |
| CF₃ | Br |
| CF₃ | I |
| CF₃ | NO₂ |
| CF₃ | NH₂ |

(Table 22)

| X | R² |
|---|---|
| CF₃ | NHC(O)CH₃ |
| CF₃ | NHC(O)OCH₃ |
| CF₃ | NHC(O)OEt |
| CF₃ | OH |
| CF₃ | OC(O)CH₃ |
| CF₃ | OCH₂Ph |
| CF₃ | OSO₂CH₃ |
| CF₃ | OSO₂CF₃ |
| CF₃ | OSO₂Ph |
| CF₃ | OSO₂(Ph-4-CH₃) |
| CF₃ | C(O)OH |
| CF₃ | C(O)OCH₃ |
| CF₃ | C(O)OEt |
| CF₃ | C(O)NH₂ |
| CF₃ | C(O)NHCH₂Pr-c |
| CF₃ | C(O)NHCH₂CF₃ |
| CF₃ | C(O)NHCH₂CH═CH₂ |
| CF₃ | C(O)NHCH₂CH═CH |
| CF₃ | C(O)NHCH₂CN |
| CF₃ | C(O)NHCH₂OCH₂CF₃ |

TABLE 1-continued

The notation - denotes absence of substitution in the Tables.

| X | R² |
|---|---|
| CF₃ | C(O)NHCH₂CH₂OCH₃ |
| CF₃ | C(O)NHCH₂CH₂OEt |
| CF₃ | C(O)NHCH=NOCH₃ |
| CF₃ | C(O)NHCH=NOEt |
| CF₃ | C(O)NHCH₂CH=NOH |
| CF₃ | C(O)NHCH₂CH=NOCH₃ |
| CF₃ | C(O)NHCH₂C(O)OH |
| CF₃ | C(O)NHCH₂C(O)OCH₃ |

(Table 23)

| X | R² |
|---|---|
| CF₃ | C(O)NHCH₂C(O)OEt |
| CF₃ | C(O)NHCH₂C(O)NH₂ |
| CF₃ | C(O)NHCH₂C(O)NHCH₂CF₃ |
| CF₃ | C(O)NHCH(CH₃)C(O)OH |
| CF₃ | C(O)NHCH(CH₃)C(O)OCH₃ |
| CF₃ | C(O)NHCH(CH₃)C(O)NHCH₂CF₃ |
| CF₃ | C(O)NH(D-11a) |
| CF₃ | C(O)NH(D-38a) |
| CF₃ | C(O)NH(D-38d)Cl |
| CF₃ | C(O)NH(D-39e)Cl |
| CF₃ | C(O)NH(D-41a) |
| CF₃ | C(O)N(C(O)CH₃)(D-41a) |
| CF₃ | C(O)N(C(O)OCH₃)(D-41a) |
| CF₃ | C(O)NH(D-41c)Cl |
| CF₃ | C(O)N(C(O)CH₃)(D-41c)Cl |
| CF₃ | C(O)N(C(O)OCH₃)(D-41c)Cl |
| CF₃ | C(O)NH(D-42a) |
| CF₃ | C(O)NH(D-44a) |
| CF₃ | C(O)NH(E-1a) |
| CF₃ | C(O)NHCH₂(D-11a) |
| CF₃ | C(O)NHCH₂(D-14a)CH₃ |
| CF₃ | C(O)NHCH₂(D-14b)Cl |
| CF₃ | C(O)NHCH₂(D-18a) |
| CF₃ | C(O)NHCH₂(D-19a) |
| CF₃ | C(O)N(C(O)CH₃)CH₂(D-19a) |
| CF₃ | C(O)N(C(O)Et)CH₂(D-19a) |
| CF₃ | C(O)N(C(O)OCH₃)CH₂(D-19a) |
| CF₃ | C(O)NHCH₂(D-25a) |

(Table 24)

| X | R² |
|---|---|
| CF₃ | C(O)NHCH₂(D-27a) |
| CF₃ | C(O)NHCH₂(D-28a) |
| CF₃ | C(O)NHCH₂(D-31a) |
| CF₃ | C(O)NHCH₂(D-34a) |
| CF₃ | C(O)NHCH₂(D-36a) |
| CF₃ | C(O)NHCH₂(D-38a) |
| CF₃ | C(O)N(C(O)CH₃)CH₂(D-38a) |
| CF₃ | C(O)N(C(O)Et)CH₂(D-38a) |
| CF₃ | C(O)N(C(O)OCH₃)CH₂(D-38a) |
| CF₃ | C(O)NHCH₂(D-40a) |
| CF₃ | C(O)NHCH₂(D-41a) |
| CF₃ | C(O)NHCH₂(D-42a) |
| CF₃ | C(O)NHCH₂(D-44a) |
| CF₃ | C(O)NHCH₂(E-1a) |
| CF₃ | C(O)NHCH₂(E-3a) |
| CF₃ | C(O)NHCH₂(E-5a) |
| CF₃ | C(O)NHC(O)OCH₃ |
| CF₃ | C(O)N(CH₃)C(O)OCH₃ |
| CF₃ | C(O)N(Et)C(O)OCH₃ |
| CF₃ | C(O)N(CH₂CN)C(O)OCH₃ |
| CF₃ | C(O)N(CH₂OCH₃)C(O)OCH₃ |
| CF₃ | C(O)N(C(O)Et)C(O)OCH₃ |
| CF₃ | C(O)N(C(O)Pr-n)C(O)OCH₃ |
| CF₃ | C(O)N(C(O)Pr-i)C(O)OCH₃ |
| CF₃ | C(O)N(C(O)OCH₃)C(O)OCH₃ |
| CF₃ | C(O)NHC(O)OEt |
| CF₃ | C(O)N(CH₃)C(O)OEt |
| CF₃ | C(O)N(Et)C(O)OEt |

(Table 25)

| X | R² |
|---|---|
| CF₃ | C(O)N(CH₂CN)C(O)OEt |
| CF₃ | C(O)N(CH₂OCH₃)C(O)OEt |
| CF₃ | C(O)N(C(O)CH₃)C(O)OEt |
| CF₃ | C(O)N(C(O)Et)C(O)OEt |
| CF₃ | C(O)N(C(O)Pr-n)C(O)OEt |
| CF₃ | C(O)N(C(O)Pr-i)C(O)OEt |
| CF₃ | C(O)N(C(O)OCH₃)C(O)OEt |
| CF₃ | C(O)NHC(O)OPr-i |
| CF₃ | C(O)N(CH₃)C(O)OPr-i |
| CF₃ | C(O)N(Et)C(O)OPr-i |
| CF₃ | C(O)N(CH₂CN)C(O)OPr-i |
| CF₃ | C(O)N(CH₂OCH₃)C(O)OPr-i |
| CF₃ | C(O)N(C(O)CH₃)C(O)OPr-i |
| CF₃ | C(O)N(C(O)Et)C(O)OPr-i |
| CF₃ | C(O)N(C(O)Pr-n)C(O)OPr-i |
| CF₃ | C(O)N(C(O)Pr-i)C(O)OPr-i |
| CF₃ | C(O)N(C(O)OCH₃)C(O)OPr-i |
| CF₃ | C(O)N(C(O)OEt)C(O)OPr-i |
| CF₃ | C(O)NHC(O)NH₂ |
| CF₃ | C(O)NHN(CH₃)Ph |
| CF₃ | C(O)N(C(O)CH₃)N(CH₃)Ph |
| CF₃ | C(O)N(C(O)OCH₃)N(CH₃)Ph |
| CF₃ | C(O)NHN(CH₃)(D-41a) |
| CF₃ | C(O)N(C(O)CH₃)N(CH₃)(D-41a) |
| CF₃ | C(O)N(C(O)OCH₃)N(CH₃)(D-41a) |
| F | CH₃ |
| F | Cl |
| F | Br |

(Table 26)

| X | R² |
|---|---|
| F | I |
| F | NO₂ |
| F | NH₂ |
| F | NHC(O)CH₃ |
| F | NHC(O)OCH₃ |
| F | NHC(O)OEt |
| F | OH |
| F | OC(O)CH₃ |
| F | OCH₂Ph |
| F | OSO₂CH₃ |
| F | OSO₂CF₃ |
| F | OSO₂Ph |
| F | OSO₂(Ph-4-CH₃) |
| F | C(O)OH |
| F | C(O)OCH₃ |
| F | C(O)OEt |
| F | C(O)NH₂ |
| F | C(O)NHCH₂Pr-c |
| F | C(O)NHCH₂CF₃ |
| F | C(O)NHCH₂CH=CH₂ |
| F | C(O)NHCH₂CH=CH |
| F | C(O)NHCH₂CN |
| F | C(O)NHCH₂OCH₂CF₃ |
| F | C(O)NHCH₂CH₂OCH₃ |
| F | C(O)NHCH₂CH₂OEt |
| F | C(O)NHCH=NOCH₃ |
| F | C(O)NHCH=NOEt |
| F | C(O)NHCH₂CH=NOH |

(Table 27)

| X | R² |
|---|---|
| F | C(O)NHCH₂CH=NOCH₃ |
| F | C(O)NHCH₂C(O)OH |
| F | C(O)NHCH₂C(O)OCH₃ |
| F | C(O)NHCH₂C(O)NHCH₂CF₃ |
| F | C(O)NHCH(CH₃)C(O)OH |
| F | C(O)NHCH(CH₃)C(O)OCH₃ |
| F | C(O)NHCH(CH₃)C(O)NHCH₂CF₃ |
| F | C(O)NH(D-11a) |
| F | C(O)NH(D-38a) |
| F | C(O)NH(D-38d)Cl |
| F | C(O)NH(D-39e)Cl |
| F | C(O)NH(D-41a) |
| F | C(O)N(C(O)CH₃)(D-41a) |
| F | C(O)N(C(O)OCH₃)(D-41a) |
| F | C(O)NH(D-41c)Cl |
| F | C(O)N(C(O)CH₃)(D-41c)Cl |
| F | C(O)N(C(O)OCH₃)(D-41c)Cl |
| F | C(O)NH(D-42a) |
| F | C(O)NH(D-44a) |
| F | C(O)NH(E-1a) |

TABLE 1-continued

The notation - denotes absence of substitution in the Tables.

| X | R² |
|---|---|
| F | C(O)NHCH₂(D-11a) |
| F | C(O)NHCH₂(D-14a)CH₃ |
| F | C(O)NHCH₂(D-14b)Cl |
| F | C(O)NHCH₂(D-18a) |
| F | C(O)NHCH₂(D-19a) |
| F | C(O)N(C(O)CH₃)CH₂(D-19a) |
| F | C(O)N(C(O)Et)CH₂(D-19a) |
| F | C(O)N(C(O)OCH₃)CH₂(D-19a) |

(Table 28)

| X | R² |
|---|---|
| F | C(O)NHCH₂(D-25a) |
| F | C(O)NHCH₂(D-27a) |
| F | C(O)NHCH₂(D-28a) |
| F | C(O)NHCH₂(D-31a) |
| F | C(O)NHCH₂(D-34a) |
| F | C(O)NHCH₂(D-36a) |
| F | C(O)NHCH₂(D-38a) |
| F | C(O)N(CH₃)CH₂(D-38a) |
| F | C(O)N(CH₂CN)CH₂(D-38a) |
| F | C(O)N(CH₂OCH₃)CH₂(D-38a) |
| F | C(O)N(C(O)CH₃)CH₂(D-38a) |
| F | C(O)N(C(O)Et)CH₂(D-38a) |
| F | C(O)N(C(O)OCH₃)CH₂(D-38a) |
| F | C(O)NHCH₂(D-40a) |
| F | C(O)NHCH₂(D-41a) |
| F | C(O)NHCH₂(D-42a) |
| F | C(O)NHCH₂(D-44a) |
| F | C(O)NHCH₂(E-1a) |
| F | C(O)NHCH₂(E-3a) |
| F | C(O)NHCH₂(E-5a) |
| F | C(O)NHC(O)OCH₃ |
| F | C(O)N(CH₃)C(O)OCH₃ |
| F | C(O)N(Et)C(O)OCH₃ |
| F | C(O)N(CH₂CN)C(O)OCH₃ |
| F | C(O)N(CH₂OCH₃)C(O)OCH₃ |
| F | C(O)N(C(O)Et)C(O)OCH₃ |
| F | C(O)N(C(O)Pr-n)C(O)OCH₃ |
| F | C(O)N(C(O)Pr-i)C(O)OCH₃ |

(Table 29)

| X | R² |
|---|---|
| F | C(O)N(C(O)OCH₃)C(O)OCH₃ |
| F | C(O)NHC(O)OEt |
| F | C(O)N(CH₃)C(O)OEt |
| F | C(O)N(Et)C(O)OEt |
| F | C(O)N(CH₂CN)C(O)OEt |
| F | C(O)N(CH₂OCH₃)C(O)OEt |
| F | C(O)N(C(O)CH₃)C(O)OEt |
| F | C(O)N(C(O)Et)C(O)OEt |
| F | C(O)N(C(O)Pr-n)C(O)OEt |
| F | C(O)N(C(O)Pr-i)C(O)OEt |
| F | C(O)N(C(O)OCH₃)C(O)OEt |
| F | C(O)NHC(O)OPr-i |
| F | C(O)N(CH₃)C(O)OPr-i |
| F | C(O)N(Et)C(O)OPr-i |
| F | C(O)N(CH₂CN)C(O)OPr-i |
| F | C(O)N(CH₂OCH₃)C(O)OPr-i |
| F | C(O)N(C(O)CH₃)C(O)OPr-i |
| F | C(O)N(C(O)Et)C(O)OPr-i |
| F | C(O)N(C(O)Pr-n)C(O)OPr-i |
| F | C(O)N(C(O)Pr-i)C(O)OPr-i |
| F | C(O)N(C(O)OCH₃)C(O)OPr-i |
| F | C(O)N(C(O)OEt)C(O)OPr-i |
| F | C(O)NHN(CH₃)Ph |
| F | C(O)N(C(O)CH₃)N(CH₃)Ph |
| F | C(O)N(C(O)OCH₃)N(CH₃)Ph |
| F | C(O)NHN(CH₃)(D-41a) |
| F | C(O)N(C(O)CH₃)N(CH₃)(D-41a) |
| F | C(O)N(C(O)OCH₃)N(CH₃)(D-41a) |

(Table 30)

| X | R² |
|---|---|
| Cl | CH₃ |
| Cl | F |
| Cl | Br |
| Cl | I |
| Cl | NO₂ |
| Cl | NH₂ |
| Cl | NHC(O)CH₃ |
| Cl | NHC(O)OCH₃ |
| Cl | NHC(O)OEt |
| Cl | OH |
| Cl | OC(O)CH₃ |
| Cl | OCH₂Ph |
| Cl | OSO₂CH₃ |
| Cl | OSO₂CF₃ |
| Cl | OSO₂Ph |
| Cl | OSO₂(Ph-4-CH₃) |
| Cl | C(O)OH |
| Cl | C(O)OCH₃ |
| Cl | C(O)OEt |
| Cl | C(O)NH₂ |
| Cl | C(O)NHCH₂Pr-c |
| Cl | C(O)NHCH₂CF₃ |
| Cl | C(O)N(CH₂OCH₃)CH₂CF₃ |
| Cl | C(O)N(C(O)CH₃)CH₂CF₃ |
| Cl | C(O)N(C(O)OCH₃)CH₂CF₃ |
| Cl | C(O)NHCH₂CH=CH₂ |
| Cl | C(O)NHCH₂CH=CH |
| Cl | C(O)NHCH₂CN |

(Table 31)

| X | R² |
|---|---|
| Cl | C(O)NHCH₂OCH₂CF₃ |
| Cl | C(O)NHCH₂CH₂OCH₃ |
| Cl | C(O)NHCH₂CH₂OEt |
| Cl | C(O)NHCH=NOCH₃ |
| Cl | C(O)NHCH=NOEt |
| Cl | C(O)NHCH₂CH=NOH |
| Cl | C(O)NHCH₂CH=NOCH₃ |
| Cl | C(O)NHCH₂C(O)OH |
| Cl | C(O)NHCH₂C(O)OCH₃ |
| Cl | C(O)NHCH₂C(O)NH₂ |
| Cl | C(O)NHCH₂C(O)NHCH₂CH₂Cl |
| Cl | C(O)NHCH₂C(O)NHCH₂Br |
| Cl | C(O)NHCH₂C(O)NHCH₂CF₃ |
| Cl | C(O)NHCH₂C(O)NHCH₂CH₂OH |
| Cl | C(O)NHCH(CH₃)C(O)OH |
| Cl | C(O)NHCH(CH₃)C(O)OCH₃ |
| Cl | C(O)NHCH(CH₃)C(O)NHCH₂CH₂Cl |
| Cl | C(O)NHCH(CH₃)C(O)NHCH₂CF₃ |
| Cl | C(O)NH(D-11a) |
| Cl | C(O)NH(D-38a) |
| Cl | C(O)NH(D-38d)Cl |
| Cl | C(O)NH(D-39e)Cl |
| Cl | C(O)NH(D-41a) |
| Cl | C(O)N(CH₃)(D-41a) |
| Cl | C(O)N(C(O)CH₃)(D-41a) |
| Cl | C(O)N(C(O)OCH₃)(D-41a) |
| Cl | C(O)NH(D-41c)Cl |
| Cl | C(O)N(CH₃)(D-41c)Cl |

(Table 32)

| X | R² |
|---|---|
| Cl | C(O)N(C(O)CH₃)(D-41c)Cl |
| Cl | C(O)N(C(O)OCH₃)(D-41c)Cl |
| Cl | C(O)NH(D-42a) |
| Cl | C(O)NH(D-44a) |
| Cl | C(O)NH(E-1a) |
| Cl | C(O)NHCH₂(D-11a) |
| Cl | C(O)NHCH₂(D-14a)CH₃ |
| Cl | C(O)NHCH₂(D-14b)Cl |
| Cl | C(O)NHCH₂(D-18a) |
| Cl | C(O)NHCH₂(D-19a) |
| Cl | C(O)N(C(O)CH₃)CH₂(D-19a) |
| Cl | C(O)N(C(O)Et)CH₂(D-19a) |
| Cl | C(O)N(C(O)OCH₃)CH₂(D-19a) |
| Cl | C(O)NHCH₂(D-25a) |
| Cl | C(O)NHCH₂(D-27a) |
| Cl | C(O)NHCH₂(D-28a) |
| Cl | C(O)NHCH₂(D-31a) |
| Cl | C(O)NHCH₂(D-34a) |
| Cl | C(O)NHCH₂(D-36a) |
| Cl | C(O)NHCH₂(D-38a) |

TABLE 1-continued

The notation - denotes absence of substitution in the Tables.

| X | R² |
|---|---|
| Cl | C(O)N(CH₂CN)CH₂(D-38a) |
| Cl | C(O)N(CH₂OCH₃)CH₂(D-38a) |
| Cl | C(O)N(C(O)CH₃)CH₂(D-38a) |
| Cl | C(O)N(C(O)Et)CH₂(D-38a) |
| Cl | C(O)N(C(O)OCH₃)CH₂(D-38a) |
| Cl | C(O)NHCH₂(D-40a) |
| Cl | C(O)NHCH₂(D-41a) |
| Cl | C(O)NHCH₂(D-42a) |
| (Table 33) | |
| Cl | C(O)NHCH₂(D-44a) |
| Cl | C(O)NHCH₂(E-1a) |
| Cl | C(O)NHCH₂(E-3a) |
| Cl | C(O)NHCH₂(E-5a) |
| Cl | C(O)NHC(O)OCH₃ |
| Cl | C(O)N(CH₃)C(O)OCH₃ |
| Cl | C(O)N(Et)C(O)OCH₃ |
| Cl | C(O)N(CH₂CN)C(O)OCH₃ |
| Cl | C(O)N(CH₂OCH₃)C(O)OCH₃ |
| Cl | C(O)N(C(O)Et)C(O)OCH₃ |
| Cl | C(O)N(C(O)Pr-n)C(O)OCH₃ |
| Cl | C(O)N(C(O)Pr-i)C(O)OCH₃ |
| Cl | C(O)N(C(O)OCH₃)C(O)OCH₃ |
| Cl | C(O)NHC(O)OEt |
| Cl | C(O)N(CH₃)C(O)OEt |
| Cl | C(O)N(Et)C(O)OEt |
| Cl | C(O)N(CH₂CN)C(O)OEt |
| Cl | C(O)N(CH₂OCH₃)C(O)OEt |
| Cl | C(O)N(C(O)CH₃)C(O)OEt |
| Cl | C(O)N(C(O)Et)C(O)OEt |
| Cl | C(O)N(C(O)Pr-n)C(O)OEt |
| Cl | C(O)N(C(O)Pr-i)C(O)OEt |
| Cl | C(O)N(C(O)OCH₃)C(O)OEt |
| Cl | C(O)NHC(O)OPr-i |
| Cl | C(O)N(CH₃)C(O)OPr-i |
| Cl | C(O)N(Et)C(O)OPr-i |
| Cl | C(O)N(CH₂CN)C(O)OPr-i |
| Cl | C(O)N(CH₂OCH₃)C(O)OPr-i |
| (Table 34) | |
| Cl | C(O)N(C(O)CH₃)C(O)OPr-i |
| Cl | C(O)N(C(O)Et)C(O)OPr-i |
| Cl | C(O)N(C(O)Pr-n)C(O)OPr-i |
| Cl | C(O)N(C(O)Pr-i)C(O)OPr-i |
| Cl | C(O)N(C(O)OCH₃)C(O)OPr-i |
| Cl | C(O)N(C(O)OEt)C(O)OPr-i |
| Cl | C(O)NHC(O)NH₂ |
| Cl | C(O)NHN(CH₃)Ph |
| Cl | C(O)N(C(O)CH₃)N(CH₃)Ph |
| Cl | C(O)N(C(O)OCH₃)N(CH₃)Ph |
| Cl | C(O)NHN(CH₃)(D-41a) |
| Cl | C(O)N(C(O)CH₃)N(CH₃)(D-41a) |
| Cl | C(O)N(C(O)OCH₃)N(CH₃)(D-41a) |
| Br | CH₃ |
| Br | F |
| Br | I |
| Br | NO₂ |
| Br | NH₂ |
| Br | NHC(O)CH₃ |
| Br | NHC(O)OCH₃ |
| Br | NHC(O)OEt |
| Br | OH |
| Br | OC(O)CH₃ |
| Br | OCH₂Ph |
| Br | OSO₂CH₃ |
| Br | OSO₂CF₃ |
| Br | OSO₂Ph |
| Br | OSO₂(Ph-4-CH₃) |
| (Table 35) | |
| Br | C(O)OH |
| Br | C(O)OCH₃ |
| Br | C(O)OEt |
| Br | C(O)NH₂ |
| Br | C(O)NHCH₂Pr-c |
| Br | C(O)NHCH₂CF₃ |
| Br | C(O)N(CH₂OCH₃)CH₂CF₃ |
| Br | C(O)N(C(O)CH₃)CH₂CF₃ |
| Br | C(O)N(C(O)OCH₃)CH₂CF₃ |
| Br | C(O)NHCH₂CH═CH₂ |
| Br | C(O)NHCH₂CH═CH |
| Br | C(O)NHCH₂CN |
| Br | C(O)NHCH₂OCH₂CF₃ |
| Br | C(O)NHCH₂CH₂OCH₃ |
| Br | C(O)NHCH₂CH₂OEt |
| Br | C(O)NHCH═NOCH₃ |
| Br | C(O)NHCH═NOEt |
| Br | C(O)NHCH₂CH═NOH |
| Br | C(O)NHCH₂CH═NOCH₃ |
| Br | C(O)NHCH₂C(O)OH |
| Br | C(O)NHCH₂C(O)OCH₃ |
| Br | C(O)NHCH₂C(O)NH₂ |
| Br | C(O)NHCH₂C(O)NHCH₂CF₃ |
| Br | C(O)NHCH₂C(O)NHCH₂CH₂OH |
| Br | C(O)NHCH(CH₃)C(O)OH |
| Br | C(O)NHCH(CH₃)C(O)OCH₃ |
| Br | C(O)NHCH(CH₃)C(O)NHCH₂CF₃ |
| Br | C(O)NH(D-11a) |
| (Table 36) | |
| Br | C(O)NH(D-38a) |
| Br | C(O)NH(D-38d)Cl |
| Br | C(O)NH(D-39e)Cl |
| Br | C(O)NH(D-41a) |
| Br | C(O)N(CH₃)(D-41a) |
| Br | C(O)N(C(O)CH₃)(D-41a) |
| Br | C(O)N(C(O)OCH₃)(D-41a) |
| Br | C(O)NH(D-41c)Cl |
| Br | C(O)N(CH₃)(D-41c)Cl |
| Br | C(O)N(C(O)CH₃)(D-41c)Cl |
| Br | C(O)N(C(O)OCH₃)(D-41c)Cl |
| Br | C(O)NH(D-42a) |
| Br | C(O)NH(D-44a) |
| Br | C(O)NH(E-1a) |
| Br | C(O)NHCH₂(D-11a) |
| Br | C(O)NHCH₂(D-14a)CH₃ |
| Br | C(O)NHCH₂(D-14b)Cl |
| Br | C(O)NHCH₂(D-18a) |
| Br | C(O)NHCH₂(D-19a) |
| Br | C(O)N(C(O)CH₃)CH₂(D-19a) |
| Br | C(O)N(C(O)Et)CH₂(D-19a) |
| Br | C(O)N(C(O)OCH₃)CH₂(D-19a) |
| Br | C(O)NHCH₂(D-25a) |
| Br | C(O)NHCH₂(D-27a) |
| Br | C(O)NHCH₂(D-28a) |
| Br | C(O)NHCH₂(D-31a) |
| Br | C(O)NHCH₂(D-34a) |
| Br | C(O)NHCH₂(D-36a) |
| (Table 37) | |
| Br | C(O)NHCH₂(D-38a) |
| Br | C(O)N(CH₂CN)CH₂(D-38a) |
| Br | C(O)N(CH₂OCH₃)CH₂(D-38a) |
| Br | C(O)N(C(O)CH₃)CH₂(D-38a) |
| Br | C(O)N(C(O)Et)CH₂(D-38a) |
| Br | C(O)N(C(O)OCH₃)CH₂(D-38a) |
| Br | C(O)NHCH₂(D-40a) |
| Br | C(O)NHCH₂(D-41a) |
| Br | C(O)NHCH₂(D-42a) |
| Br | C(O)NHCH₂(D-44a) |
| Br | C(O)NHCH₂(E-1a) |
| Br | C(O)NHCH₂(E-3a) |
| Br | C(O)NHCH₂(E-5a) |
| Br | C(O)NHC(O)OCH₃ |
| Br | C(O)N(CH₃)C(O)OCH₃ |
| Br | C(O)N(Et)C(O)OCH₃ |
| Br | C(O)N(CH₂CN)C(O)OCH₃ |
| Br | C(O)N(CH₂OCH₃)C(O)OCH₃ |
| Br | C(O)N(C(O)Et)C(O)OCH₃ |
| Br | C(O)N(C(O)Pr-n)C(O)OCH₃ |

TABLE 1-continued

The notation - denotes absence of substitution in the Tables.

| X | R² |
|---|---|
| Br | C(O)N(C(O)Pr-i)C(O)OCH₃ |
| Br | C(O)N(C(O)OCH₃)C(O)OCH₃ |
| Br | C(O)NHC(O)OEt |
| Br | C(O)N(CH₃)C(O)OEt |
| Br | C(O)N(Et)C(O)OEt |
| Br | C(O)N(CH₂CN)C(O)OEt |
| Br | C(O)N(CH₂OCH₃)C(O)OEt |
| Br | C(O)N(C(O)CH₃)C(O)OEt |
| | (Table 38) |
| Br | C(O)N(C(O)Et)C(O)OEt |
| Br | C(O)N(C(O)Pr-n)C(O)OEt |
| Br | C(O)N(C(O)Pr-i)C(O)OEt |
| Br | C(O)N(C(O)OCH₃)C(O)OEt |
| Br | C(O)NHC(O)OPr-i |
| Br | C(O)N(CH₃)C(O)OPr-i |
| Br | C(O)N(Et)C(O)OPr-i |
| Br | C(O)N(CH₂CN)C(O)OPr-i |
| Br | C(O)N(CH₂OCH₃)C(O)OPr-i |
| Br | C(O)N(C(O)CH₃)C(O)OPr-i |
| Br | C(O)N(C(O)Et)C(O)OPr-i |
| Br | C(O)N(C(O)Pr-n)C(O)OPr-i |
| Br | C(O)N(C(O)Pr-i)C(O)OPr-i |
| Br | C(O)N(C(O)OCH₃)C(O)OPr-i |
| Br | C(O)N(C(O)OEt)C(O)OPr-i |
| Br | C(O)NHC(O)NH₂ |
| Br | C(O)NHN(CH₃)Ph |
| Br | C(O)N(C(O)CH₃)N(CH₃)Ph |
| Br | C(O)N(C(O)OCH₃)N(CH₃)Ph |
| Br | C(O)NHN(CH₃)(D-41a) |
| Br | C(O)N(C(O)CH₃)N(CH₃)(D-41a) |
| Br | C(O)N(C(O)OCH₃)N(CH₃)(D-41a) |
| I | CH₃ |
| I | NO₂ |
| I | NH₂ |
| I | NHC(O)CH₃ |
| I | NHC(O)OCH₃ |
| I | NHC(O)OEt |
| | (Table 39) |
| I | OH |
| I | OC(O)CH₃ |
| I | OCH₂Ph |
| I | OSO₂CF₃ |
| I | C(O)OH |
| I | C(O)OCH₃ |
| I | C(O)OEt |
| I | C(O)NH₂ |
| I | C(O)NHCH₂Pr-c |
| I | C(O)NHCH₂CF₃ |
| I | C(O)NHCH₂CH=CH₂ |
| I | C(O)NHCH₂CH=CH |
| I | C(O)NHCH₂CN |
| I | C(O)NHCH₂OCH₂CF₃ |
| I | C(O)NHCH₂CH₂OCH₃ |
| I | C(O)NHCH₂CH₂OEt |
| I | C(O)NHCH=NOCH₃ |
| I | C(O)NHCH=NOEt |
| I | C(O)NHCH₂CH=NOH |
| I | C(O)NHCH₂CH=NOCH₃ |
| I | C(O)NHCH₂C(O)OH |
| I | C(O)NHCH₂C(O)OCH₃ |
| I | C(O)NHCH₂C(O)NHCH₂CF₃ |
| I | C(O)NHCH(CH₃)C(O)OH |
| I | C(O)NHCH(CH₃)C(O)OCH₃ |
| I | C(O)NHCH(CH₃)C(O)NHCH₂CF₃ |
| I | C(O)NH(D-11a) |
| I | C(O)NH(D-38a) |
| | (Table 40) |
| I | C(O)NH(D-38d)Cl |
| I | C(O)NH(D-39e)Cl |
| I | C(O)NH(D-41a) |
| I | C(O)N(C(O)CH₃)(D-41a) |
| I | C(O)N(C(O)OCH₃)(D-41a) |
| I | C(O)NH(D-41c)Cl |
| I | C(O)N(C(O)CH₃)(D-41c)Cl |
| I | C(O)N(C(O)OCH₃)(D-41c)Cl |
| I | C(O)NH(D-42a) |
| I | C(O)NH(D-44a) |
| I | C(O)NH(E-1a) |
| I | C(O)NHCH₂(D-11a) |
| I | C(O)NHCH₂(D-14a)CH₃ |
| I | C(O)NHCH₂(D-14b)Cl |
| I | C(O)NHCH₂(D-18a) |
| I | C(O)NHCH₂(D-19a) |
| I | C(O)N(C(O)CH₃)CH₂(D-19a) |
| I | C(O)N(C(O)Et)CH₂(D-19a) |
| I | C(O)N(C(O)OCH₃)CH₂(D-19a) |
| I | C(O)NHCH₂(D-25a) |
| I | C(O)NHCH₂(D-27a) |
| I | C(O)NHCH₂(D-28a) |
| I | C(O)NHCH₂(D-31a) |
| I | C(O)NHCH₂(D-34a) |
| I | C(O)NHCH₂(D-36a) |
| I | C(O)NHCH₂(D-38a) |
| I | C(O)N(CH₂CN)CH₂(D-38a) |
| I | C(O)N(CH₂OCH₃)CH₂(D-38a) |
| | (Table 41) |
| I | C(O)N(C(O)CH₃)CH₂(D-38a) |
| I | C(O)N(C(O)Et)CH₂(D-38a) |
| I | C(O)N(C(O)OCH₃)CH₂(D-38a) |
| I | C(O)NHCH₂(D-40a) |
| I | C(O)NHCH₂(D-41a) |
| I | C(O)NHCH₂(D-42a) |
| I | C(O)NHCH₂(D-44a) |
| I | C(O)NHCH₂(E-1a) |
| I | C(O)NHCH₂(E-3a) |
| I | C(O)NHCH₂(E-5a) |
| I | C(O)NHC(O)OCH₃ |
| I | C(O)N(CH₃)C(O)OCH₃ |
| I | C(O)N(Et)C(O)OCH₃ |
| I | C(O)N(CH₂CN)C(O)OCH₃ |
| I | C(O)N(CH₂OCH₃)C(O)OCH₃ |
| I | C(O)N(C(O)Et)C(O)OCH₃ |
| I | C(O)N(C(O)Pr-n)C(O)OCH₃ |
| I | C(O)N(C(O)Pr-i)C(O)OCH₃ |
| I | C(O)N(C(O)OCH₃)C(O)OCH₃ |
| I | C(O)NHC(O)OEt |
| I | C(O)N(CH₃)C(O)OEt |
| I | C(O)N(Et)C(O)OEt |
| I | C(O)N(CH₂CN)C(O)OEt |
| I | C(O)N(CH₂OCH₃)C(O)OEt |
| I | C(O)N(C(O)CH₃)C(O)OEt |
| I | C(O)N(C(O)Et)C(O)OEt |
| I | C(O)N(C(O)Pr-n)C(O)OEt |
| I | C(O)N(C(O)Pr-i)C(O)OEt |
| | (Table 42) |
| I | C(O)N(C(O)OCH₃)C(O)OEt |
| I | C(O)NHC(O)OPr-i |
| I | C(O)N(CH₃)C(O)OPr-i |
| I | C(O)N(Et)C(O)OPr-i |
| I | C(O)N(CH₂CN)C(O)OPr-i |
| I | C(O)N(CH₂OCH₃)C(O)OPr-i |
| I | C(O)N(C(O)CH₃)C(O)OPr-i |
| I | C(O)N(C(O)Et)C(O)OPr-i |
| I | C(O)N(C(O)Pr-n)C(O)OPr-i |
| I | C(O)N(C(O)Pr-i)C(O)OPr-i |
| I | C(O)N(C(O)OCH₃)C(O)OPr-i |
| I | C(O)N(C(O)OEt)C(O)OPr-i |
| I | C(O)NHC(O)NH₂ |
| I | C(O)NHN(CH₃)Ph |
| I | C(O)N(C(O)CH₃)N(CH₃)Ph |
| I | C(O)N(C(O)OCH₃)N(CH₃)Ph |
| I | C(O)NHN(CH₃)(D-41a) |
| I | C(O)N(C(O)CH₃)N(CH₃)(D-41a) |
| I | C(O)N(C(O)OCH₃)N(CH₃)(D-41a) |

EXAMPLES

Examples of the present invention are shown as follows, but the present invention is not limited to these examples.

Synthetic Examples

Synthetic Example 1

1-(4-Bromo-3-methyphenyl)-3-(3,5-dichlorophenyl)-3-hydroxy-4,4,4-trifluorobutane-1-one (Compound No. 1-06 of the Present Invention)

Step 1; Production of methyl 3,5-dichlorobenzoate

To a solution of 50 g of 3,5-dichlorobenzoic acid in 120 g of methanol, 10 g of concentrated sulfuric acid was added and the mixture was heated and refluxed for 5 hours. After the reaction solution was cooled to room temperature, the solvent was distilled off under reduced pressure. The resulting residue was dissolved in 200 g of ethyl acetate, washed with water (200 g×2) followed by washing with saturated sodium hydrogen carbonate solution, and then washed with water. After an organic layer was dried with anhydrous magnesium sulfate, the solvent was distilled off under reduced pressure to obtain 48.6 g of aimed product as white solid.

$^1$H NMR (CDCl$_3$, Me$_4$Si, 300 MHz) δ 7.90 (s, 2H), 7.54 (s, 1H), 3.94 (s, 3H).

Step 2; Production of 3',5'-dichloro-2,2,2-trifluoroacetophenone

To a solution of 25 g of 3,5-dichlorobenzoic acid methyl and 22.5 g of trifluoromethyltrimethylsilane in 300 g of dimethoxyethane, 0.37 g of cesium fluoride was added with ice-cooling and the mixture was warmed to room temperature and stirred for 4 hours. After disappearance of the raw material was confirmed, 200 g of water was put into the reaction solution to extract with 200 g of ethyl acetate. After the organic layer was dehydrated and dried with saturated saline followed by anhydrous magnesium sulfate, the solvent was distilled off under reduced pressure to obtain 35.5 g of 1-(3, 5-dichlorophenyl)-2,2,2-trifluoro-1-trimethylsilyloxy-1-methoxyethane as yellow liquid matter. The obtained matter was dissolved in 100 mL of tetrahydrofuran, 9.75 mL of 100-mL 1M tetrahydrofuran solution of tetrabutylammonium fluoride at room temperature was dripped, and the mixture was stirred for two hours at the same temperature. After the completion of the reaction, the solvent was distilled off under reduced pressure, the resulting residue was dissolved in ethyl acetate, and an organic layer was washed with water and dried with anhydrous magnesium sulfate to distill off the solvent under reduced pressure. By distilling the resulting residue under reduced pressure, 24.2 g of aimed product was obtained as colorless liquid.

Boiling point, 87° C. (1.7 kPa).

$^1$H NMR (CDCl$_3$, Me$_4$Si, 300 MHz) δ 7.92-7.93 (m, 2H), 7.70-7.71 (m, 1H).

Step 3; Production of 1-(4-bromo-3-methylphenyl)-3-(3, 5-dichlorophenyl)-3-hydroxy-4,4,4-trifluorobutane-1-one A solution of 7.0 g of 4-bromo-3-methylacetophenone that can be synthesized according to a procedure described in WO 96/019477 pamphlet in 40 mL of tetrahydrofuran was cooled to −60° C. with dry ice-acetone, whereto 32.8 mL of 1M tetrahydrofuran solution of lithium bis(trimethylsilyl)amide was dripped for 30 minutes. After the end of dripping, the mixture was stirred for 1 hour at the same temperature. And after a solution of 7.98 g of 3',5'-dichloro-2,2,2-trifluoroacetophenone in 15 mL of tetrahydrofuran was dripped, the reaction solution was gradually warmed to room temperature and stirred for 3 hours at room temperature. After the end of the reaction, 2N hydrochloric acid was added to the reaction solution, the solvent was distilled off under reduced pressure, and the resulting residue was dissolved in ethyl acetate to be washed with water. After an organic layer was dried with anhydrous magnesium sulfate, the solvent was distilled off under reduced pressure. By washing the resulting solid with diisopropylether, 9.19 g of aimed product was obtained as white solid.

Melting point, 141 to 142° C.

$^1$H NMR (CDCl$_3$, Me$_4$Si, 300 MHz) δ 7.77 (d, J=2.1 Hz, 1H), 7.68 (d, J=8.4 Hz, 1H), 7.48 (dd, J=8.4, 2.1 Hz, 1H), 7.49 (brs, 2H), 7.34 (brs, 1H), 5.72 (s, 1H), 3.81 (d, J=17.4 Hz, 1H), 3.63 (d, J=17.4 Hz, 1H), 2.48 (s, 3H).

Synthetic Example 2

1-(4-Bromo-3-methylphenyl)-3-(3,5-dichlorophenyl)-4,4,4-trifluoro-2-butene-1-one (Compound No. 2-15 of the Present Invention)

To a solution of 0.3 g of 1-(4-bromo-3-methylphenyl)-3-(3,5-dichlorophenyl)-3-hydroxy-4,4,4-trifluorobutane-1-one synthesized under Synthetic Example 1 in 3 g toluene, 0.391 g of thionyl chloride and 0.104 g of pyridine were added at room temperature and the mixture was stirred for 1 hour at 80° C. After the end of reaction, the reaction solution was cooled to room temperature, added with toluene and 2N hydrochloric acid and separated, and then an organic layer was washed with water and dried with anhydrous magnesium sulfate to distill off the solvent under reduced pressure. The resulting residue, which although contains mixed geometrical isomers, was purified using silica gel column chromatography that was eluted with ethyl acetate-hexane (1:10), and 0.244 g of aimed product was obtained as yellow solid.

Under this synthetic example, only a major component out of geometrical isomers was isolated as aimed product according to $^1$H NMR measurement, and differential NOE measurement revealed correlation between olefinic proton and proton at 2-nd or 6-th position on 3,5-dichlorobenzene ring; therefore, the aimed product was identified as Z-form represented by the following structure.

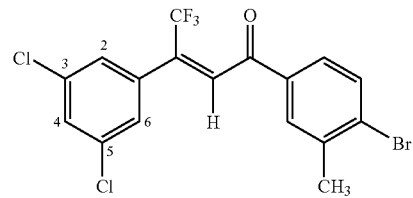

Melting point, 67 to 69° C.

$^1$H NMR (CDCl$_3$, Me$_4$Si, 300 MHz) δ 7.67 (d, J=2.1 Hz, 1H), 7.63 (d, J=8.4 Hz, 1H), 7.48 (dd, J=8.4, 2.1 Hz, 1H), 7.32-7.36 (m, 2H), 7.12-7.17 (m, 2H), 2.44 (s, 3H).

Synthetic Example 3

1-(4-Bromophenyl)-3-(3,5-dichlorophenyl)-4,4,4-trifluoro-2-butene-1-one (Compound No. 2-01 of the Present Invention)

Step 1; Production of 4-bromophenacylphosphonium bromide

A solution of 10 g of 4-bromophenacyl bromide and 9.63 g of triphenylphosphine in 50 mL tetrahydrofuran was stirred for 1 hour at 40° C. After the completion of the reaction, the solution was cooled to room temperature and then precipitated solid matter was isolated by filtration and washed with tetrahydrofuran to obtain 19 g of aimed product as white solid.

Step 2; Production of 1-(4-bromophenyl)-3-(3,5-dichlorophenyl)-4,4,4-trifluoro-2-butene-1-one To a solution of 7 g 4-bromophenacylphosphonium bromide and 3 g of 3',5'-dichloro-2,2,2-trifluoroacetophenone that was produced in steps 1 to 2 under Synthetic Example 1 in 150 mL of chloroform, 1.52 g of triethylamine was added slowly at room temperature and the mixture was stirred for 2 hours at the same temperature. After the completion of the reaction, the solvent was distilled off under reduced pressure, the resulting residue was dissolved in 150 mL of ethyl acetate, washed with diluted hydrochloric acid (100 mL×2), and then dehydrated and dried with saturated saline followed by anhydrous magnesium sulfate, and the solvent was distilled off under reduced pressure. The resulting residue containing mixed geometrical isomers, was purified using silica gel column chromatography that was eluted with ethyl acetate-hexane (1:8) to obtain 4.6 g of aimed product as yellow solid.

Under this synthetic example, only a major component out of geometrical isomers was isolated as aimed product according to $^1$H NMR measurement.

Melting point, 58 to 60° C.

$^1$H NMR (CDCl$_3$, Me$_4$Si, 300 MHz) δ 7.69 (d, J=8.1 Hz, 2H), 7.60 (d, J=8.1 Hz, 2H), 7.30-7.40 (m, 2H), 7.15 (brs, 2H).

Synthetic Example 4

Methyl 4-(3-(3,5-dichlorophenyl)-4,4,4-trifluoro-2-butenoyl)benzoate (Compound No. 2-06 of the Present Invention)

To a solution of 2.0 g of methyl 4-acetylbenzoate in 50 mL of chloroform, 1.98 g of bromine was added at room temperature, the mixture was stirred for 30 minutes, and then the solvent was distilled off under reduced pressure. The resulting residue was dissolved in 40 mL of tetrahydrofuran whereto 2.94 g of triphenylphosphine was added, and the mixture was stirred for 30 minutes at 50° C., and the solvent was distilled off under reduced pressure. The resulting residue was dissolved in 50 mL of chloroform whereto 2.72 g of 3',5'-dichloro-2,2,2-trifluoroacetophenone that was produced in step 2 under Synthetic Example 1 and 1.4 g of triethylamine were added, and the mixture was stirred for 4 hours at room temperature. After that, the reaction solution was washed with water (50 mL), an organic layer was dried with anhydrous sodium sulfate, and the solvent was distilled off under reduced pressure. The resulting residue was purified using silica gel column chromatography that was eluted with ethyl acetate-hexane (1:9) followed by crystallization from hexane to obtain 1.0 g of aimed product as slightly yellow solid.

Under this synthetic example, the aimed product was isolated as a mixture containing geometrical isomers at a ratio of 19:1 according to $^1$H NMR measurement.

Melting point, 65.5 to 67.5° C.

$^1$H NMR (CDCl$_3$, Me$_4$Si, 300 MHz) δ 8.11 (d, J=8.4 Hz, 2H), 7.87 (d, J=8.4 Hz, 2H), 7.30-7.42 (m, 2H), 7.15 (d, J=1.8 Hz, 2H), 3.95 (s, 3H) only for the major component.

Synthetic Example 5

4-(3-(3,5-Dichlorophenyl)-4,4,4-trifluoro-2-butenoyl)benzoic acid (Compound No. 2-05 of the Present Invention)

To a solution of 1.95 g of 1-(4-bromophenyl)-3-(3,5-dichlorophenyl)-4,4,4-trifluoro-2-butene-1-one that was synthesized under Synthetic Example 3 and 0.56 g of triethylamine in 10 mL of tertiary-butyl alcohol, 10 mL of dioxane, and 5 mL of water in an autoclave, 51 mg of 1,1'-bis(diphenylphosphino) ferrocene and 10 mg of palladium(II) acetate were added, the mixture was stirred for 4 hours at 110° C. in an atmosphere of carbon monoxide at 0.5 MPa followed by cooling to room temperature, and then further 10 mg of palladium(II) acetate were added, the mixture was stirred for 4 hours at 110° C. in an atmosphere of carbon monoxide at 0.5 MPa. After that, the temperature was cooled to room temperature to isolate solid matter by filtration whereto diluted hydrochloric acid was added to extract with ethyl acetate, and then an organic layer was dried with anhydrous sodium sulfate and the solvent was distilled off under reduced pressure. The resulting residue was purified using silica gel column chromatography that was eluted with ethyl acetate-hexane (1:8) to obtain 1.5 g of aimed product as resinous matter.

$^1$H NMR (CDCl$_3$, Me$_4$Si, 300 MHz) δ 8.18 (d, J=8.5 Hz, 2H), 7.91 (d, J=8.5 Hz, 2H), 7.40 (s, 1H), 7.34 (s, 1H), 7.16 (s, 2H).

Synthetic Example 6

4-(3-(3,5-Dichlorophenyl)-4,4,4-trifluoro-2-butenoyl)-2-methylbenzoic acid (Compound No. 2-17 of the Present Invention)

To a solution of 4.85 g of 1-(4-bromo-3-methylphenyl)-3-(3,5-dichlorophenyl)-4,4,4-trifluoro-2-butene-1-one representing mixed geometrical isomers (isomeric ratio of 8:1) that was synthesized according to Synthetic Examples 1 and 2 and 1.36 g of sodium acetate in 20 mL of 1,2-dimethoxyethane and 20 mL of water in an autoclave, 0.25 g of 1,1'-bis(diphenylphosphino) ferrocene and 50 mg of palladium(II) acetate were added, the mixture was stirred for 5.5 hours at 110° C. in an atmosphere of carbon monoxide at 1.0 MPa. After that, the temperature was cooled to room temperature to isolate solid matter by filtration, diluted hydrochloric acid was added to extract with ethyl acetate, and then an organic layer was dehydrated and dried with saturated saline followed by anhydrous magnesium sulfate and the solvent was distilled off under reduced pressure. The resulting residue was purified using silica gel column chromatography that was eluted with ethyl acetate-hexane (1:5) followed by crystallization from a mixed solvent of hexane and a small amount of ethyl acetate to obtain 2.6 g of aimed product as white solid.

Under this synthetic example, aimed product was isolated as a mixture containing geometrical isomers at a ratio of 10:1 according to $^1$H NMR measurement.

Melting point, 123.0-126.5° C.

$^1$H NMR (CDCl$_3$, Me$_4$Si, 300 MHz) δ 8.11 (d, J=8.7 Hz, 1H), 7.65-7.70 (m, 2H), 7.30-7.40 (m, 2H), 7.16 (d, J=1.8 Hz, 2H), 2.69 (s, 3H) only for the major component.

Synthetic Example 7

4-(3-(3,5-Dichlorophenyl)-4,4,4-trifluoro-2-butenoyl)-N-(2-pyridylmethyl)benzoic acid amide (Compound No. 2-12 of the Present Invention)

To a solution of 0.5 g of 4-(3-(3,5-dichlorophenyl)-4,4,4-trifluoro-2-butenoyl)benzoic acid that was synthesized under Synthetic Example 4 and 0.21 g of 2-picolylamine in 6 mL of N,N-dimethylformamide, 0.32 g of 1-(3-(diethylamino)propyl)-3-ethylcarbodiimide chloride was added at room temperature and the mixture was stirred for 72 hours. After the completion of reaction, 20 mL of ethyl acetate and 15 mL of saturated saline were added to the reaction solution, the mixture was separated to extract an aqueous layer with 10 mL of ethyl acetate whereto an organic layer was added, the resulting mixture was washed with 10 mL of water and dried with anhydrous sodium sulfate, and the solvent was distilled off under reduced pressure. After purification of the resulting residue using silica gel column chromatography that was eluted with ethyl acetate-hexane (5:1) to obtain 0.17 g of aimed product as resinous matter.

$^1$H NMR (CDCl$_3$, Me$_4$Si, 300 MHz) δ 8.56 (d, J=5.1 Hz, 1H), 7.85-8.10 (m, 5H), 7.65-7.75 (m, 1H), 7.15-7.50 (m, 6H), 4.75 (d, J=4.5 Hz, 2H).

Synthetic Example 8

N-(5-Chloro-2-pyrimidinyl)-4-(3-(3,5-dichlorophenyl)-4,4,4-trifluoro-2-butenoyl) benzoic acid amide (Compound No. 2-10 of the Present Invention)

Step 1; Production of 4-(3-(3,5-dichlorophenyl)-4,4,4-trifluoro-2-butenoyl)benzoic acid chloride To a solution of 1.0 g of 4-(3-(3,5-dichlorophenyl)-4,4,4-trifluoro-2-butenoyl)benzoic acid representing mixed geometrical isomers (isomeric ratio of 10:1) synthesized according to Synthetic Example 6 in 10 mL of toluene, a drop of N,N-dimethylformamide and 0.46 g thionyl chloride were added and the mixture was stirred for 1.5 hours at 90° C. After that, the temperature was cooled to room temperature, insoluble matter was removed by filtration, and then the solvent was distilled off under reduced pressure to obtain 1.0 g of aimed product as brown solid.

The resulting aimed product was not purified any more and used for the next reaction.

Step 2; Production of N-(5-chloro-2-pyrimidinyl)-4-(3-(3,5-dichlorophenyl)-4,4,4-trifluoro-2-butenoyl)benzoic acid amide To a solution of 0.5 g of 2-amino-5-chloropyrimidine in 20 mL of pyridine, 0.5 g of 4-(3-(3,5-dichlorophenyl)-4,4,4-trifluoro-2-butenoyl)benzoic acid chloride was poured at room temperature and the mixture was stirred for 2.5 hours. After that, water was added to the reaction solution that was extracted with ethyl acetate, an organic layer was washed with water and diluted hydrochloric acid and then dehydrated and dried with saturated saline followed by anhydrous magnesium sulfate, and the solvent was distilled off under reduced pressure. The resulting residue was purified using silica gel column chromatography that was eluted with ethyl acetate-hexane (5:2) followed by crystallization from a mixed solvent of hexane and a small amount of ethyl acetate to obtain 0.31 g of aimed product as white solid.

Under this synthetic example, the aimed product was isolated as a mixture containing geometrical isomers at a ratio of 10:1 according to $^1$H NMR measurement.

Melting point: 71.0-76.0° C.

$^1$H NMR (CDCl$_3$, Me$_4$Si, 300 MHz) δ 8.73 (brs, 1H), 8.62 (s, 2H), 8.00 (d, J=8.1 Hz, 2H), 7.94 (d, J=8.1 Hz, 2H), 7.30-7.40 (m, 2), 7.16 (d, J=2.1 Hz, 2H) only for the major component.

Synthetic Example 9

4-(3-(3,5-Dichlorophenyl)-4,4,4-trifluoro-2-butenoyl)benzoic acid amide (Compound No. 2-07 of the Present Invention)

To 10 mL of 28% ammonia water, a solution of 0.5 g of 4-(3-(3,5-dichlorophenyl)-4,4,4-trifluoro-2-butenoyl)benzoic acid chloride that was synthesized in step 1 under Synthetic Example 8 in 5 mL of tetrahydrofuran was dripped at room temperature and the mixture was stirred for 2 hours. After the completion of reaction, the reaction solution was extracted with ethyl acetate, an organic layer was washed with water and diluted hydrochloric acid, and then dehydrated and dried with saturated saline followed by anhydrous magnesium sulfate, and the solvent was distilled off under reduced pressure. The resulting residue was purified using silica gel column chromatography that was eluted with ethyl acetate-hexane (2:1) followed by crystallization from a mixed solvent of hexane and a small amount of ethyl acetate to obtain 0.38 g of aimed product as slightly yellow solid.

Under this synthetic example, the aimed product was isolated as a mixture containing geometrical isomers at a ratio of 10:1 according to $^1$H NMR measurement.

Melting point: 156.0-159.5° C.

$^1$H NMR (CDCl$_3$-DMSO-d$_6$, Me$_4$Si, 300 MHz) δ 8.00 (d, J=7.8 Hz, 2H), 7.89 (d, J=7.8 Hz, 2H), 7.30-7.50 (m, 3H), 7.16 (d, J=1.5 Hz, 2H), 6.48 (brs, 1H) only for the major component.

Synthetic Example 10

4-(3-(3,5-Dichlorophenyl)-4,4,4-trifluoro-2-butenoyl)-N-(2-tetrahydrofuranyl)benzoic acid amide (Compound No. 2-09 of the Present Invention)

To a solution of 0.25 g of 4-(3-(3,5-dichlorophenyl)-4,4,4-trifluoro-2-butenoyl)benzoic acid amide that was synthesized under Synthetic Example 9 in 3 mL of dichloromethane, 68 mg of 2,3-dihydrofuran and a catalytic amount of p-toluenesulfonic acid monohydrate were added and the mixture was stirred for 18 hours at room temperature. The solvent was distilled off from the reaction solution under reduced pressure, and the resulting residue was purified using silica gel column chromatography that was eluted with ethyl acetate-hexane (2:3) followed by crystallization from a mixed solvent of hexane and a small amount of ethyl acetate to obtain 0.12 g of aimed product as yellow solid.

Under this synthetic example, the aimed product was isolated as a mixture containing geometrical isomers at a ratio of 12:1 according to $^1$H NMR measurement.

Melting point: 140.5-146.0° C.

$^1$H NMR (CDCl$_3$, Me$_4$Si, 300 MHz) δ 7.91 (d, J=8.1 Hz, 2H), 7.83 (d, J=8.1 Hz, 2H), 7.30-7.40 (m, 2H), 7.15 (d, J=1.5 Hz, 2H), 6.45 (brd, J=6.6 Hz, 1H), 5.85-5.95 (m, 1H), 3.95-4.05 (m, 1H), 3.82-3.92 (m, 1H), 2.25-2.40 (m, 1H), 1.80-2.10 (m, 3H) only for the major component.

Synthetic Example 11

4-(3-(3,5-Dichlorophenyl)-4,4,4-trifluoro-2-butenoyl)-N-(2-methoxyethyl)benzoic acid amide (Compound No. 2-08 of the Present Invention)

To a solution of 0.2 g of 4-(3-(3,5-dichlorophenyl)-4,4,4-trifluoro-2-butenoyl)benzoic acid representing mixed geometrical isomers (isomeric ratio of 10:1) that was synthesized according to Synthetic Example 6 in 3 mL of toluene, a drop of N,N-dimethylformamide and 0.1 g of thionyl chloride was added and the mixture was stirred for 1.5 hours at 90° C. After that the temperature was cooled to room temperature, insoluble matter was removed by filtration, and then the solvent was distilled off under reduced pressure. The resulting residue was dissolved in 3 mL of dichloromethane, dripped in a solution of 2 mL of dichloromethane containing 0.5 g of ice-cooled 2-methoxyethylamine and 80 mg of triethylamine, and stirred for 30 minutes at the same temperature. The solvent was distilled off from the reaction solution under reduced pressure, the resulting residue was purified using silica gel column chromatography that was eluted with ethyl acetate-hexane (2:1) followed by crystallization from a mixed solvent of hexane and a small amount of ethyl acetate to obtain 0.18 g of aimed product as yellow solid.

Under this synthetic example, the aimed product was isolated as a mixture containing geometrical isomers at a ratio of 24:1 according to $^1$H NMR measurement.

Melting point: 150.5-153.0° C.

$^1$H NMR (CDCl$_3$, Me$_4$Si, 300 MHz) δ 7.89 (d, J=8.1 Hz, 2H), 7.85 (d, J=8.1 Hz, 2H), 7.30-7.40 (m, 2H), 7.15 (d, J=1.8 Hz, 2H), 6.55 (brs, 1H), 3.55-3.70 (m, 4H), 3.40 (s, 3H) only for the major component.

Synthetic Example 12

Methyl N-(4-(3-(3,5-dichlorophenyl)-4,4,4-trifluoro-2-butenoyl)-2-methylbenzoyl)-N-(2-pyridylmethyl) carbamate (Compound No. 2-23 of the Present Invention)

Step 1; Production of dichloromethane solution of 4-(3-(3,5-dichlorophenyl)-4,4,4-trifluoro-2-butenoyl)-2-methylbenzoyl chloride To a solution of 0.6 g of 4-(3-(3,5-dichlorophenyl)-4,4,4-trifluoro-2-butenoyl)benzoic acid representing mixed geometrical isomers (isomeric ratio of 10:1) synthesized according to Synthetic Example 6 in 15 mL of toluene, a drop of N,N-dimethylformamide and 0.3 mL of thionyl chloride was added and the mixture was stirred for 1.5 hours at 90° C. After that, the temperature was cooled to room temperature, insoluble matter was removed by filtration, and then the solvent was distilled off under reduced pressure. The resulting residue was dissolved in dichloromethane to obtain 6 g of objective solution.

The dichlorometane solution containing the resulting acid chloride was separated and used for the reaction below.

Step 2; Production of methyl N-(4-(3-(3,5-dichlorophenyl)-4,4,4-trifluoro-2-butenoyl)-2-methylbenzoyl)-N-(2-pyridylmethyl)carbamate To a suspension of 70 mg of t-butoxypotassium in 2 mL of tetrahydrofuran, a solution of 90 mg of methyl N-(2-pyridilmethyl)carbamate was added with ice-cooling, and the mixture was stirred for 30 minutes at the same temperature. Then, 2 g of dichloromethane solution of acid chloride prepared in step 1 was dripped in the reaction mixture, and the mixture was stirred for 1.5 hours at room temperature. After that, diluted hydrochloric acid was added to the reaction solution to extract with ethyl acetate, an organic layer was dehydrated and dried with saturated saline followed by anhydrous magnesium sulfate, and the solvent was distilled off under reduced pressure. The resulting residue was purified using silica gel column chromatography that was eluted with ethyl acetate-hexane (1:1) to obtain 0.15 g of aimed product as yellow oily matter.

Under this synthetic example, the aimed product was isolated as a mixture containing geometrical isomers at a ratio of 16:1 according to $^1$H NMR measurement.

$^1$H NMR (CDCl$_3$, Me$_4$Si, 300 MHz) δ 8.57 (d, J=4.8 Hz, 1H), 7.65-7.75 (m, 2H), 7.10-7.45 (m, 8H), 5.22 (s, 2H), 3.56 (s, 3H), 2.41 (s, 3H) only for the major component.

Synthetic Example 13

Methyl N-(4-(3-(3,5-dichlorophenyl)-4,4,4-trifluoro-2-butenoyl)-2-methylbenzoyl)carbamate (Compound No. 2-20 of the Present Invention)

To a solution of 0.2 g of 4-(3-(3,5-dichlorophenyl)-4,4,4-trifluoro-2-butenoyl)-2-methylbenzoic acid amide representing mixed geometrical isomers (isomeric ratio of 10:1) that was synthesized according to Synthetic Example 9 in 3 mL of dichloromethane, 76 mg of oxalyl chloride was added and the mixture was stirred for 2 hours while heating and refluxing. After the completion of reaction, the solvent was distilled off under reduced pressure, and the resulting residue was dissolved in 3 mL of dichloromethane, which was dripped in 5 mL of methanol at room temperature. After the mixture was stirred for 2 hours, the solvent was distilled off under reduced pressure, and the resulting residue was purified using silica gel column chromatography that was eluted with ethyl acetate-hexane (2:1) followed by crystallization from a mixed solvent of hexane and a small amount of ethyl acetate to obtain 0.15 g of aimed product as white solid.

Under this synthetic example, the aimed product was isolated as a mixture containing geometrical isomers at a ratio of 13:1 according to $^1$H NMR measurement.

Melting point: 145.5-149.0° C.

$^1$H NMR (CDCl$_3$, Me$_4$Si, 300 MHz) δ 7.96 (brs, 1H), 7.65-7.70 (m, 2H), 7.30-7.45 (m, 3H), 7.16 (d, J=1.5 Hz, 2H), 3.79 (s, 3H), 2.45 (s, 3H) only for the major component.

Synthetic Example 14

4-(3-(3,5-Dichlorophenyl)-4,4,4-trifluoro-2-butenoyl)-N-(methoxyiminomethyl)-2-methylbenzoic acid amide (Compound No. 2-26 of the Present Invention)

To a solution of 0.18 g of 4-(3-(3,5-dichlorophenyl)-4,4,4-trifluoro-2-butenoyl)-2-methylbenzoic acid amide representing mixed geometrical isomers (isomeric ratio of 10:1) that was synthesized according to Synthetic Example 9 in 3 mL of tetrahydrofuran, 0.11 g of N,N-dimethylformamide dimethyl acetal was added and the mixture was stirred for 2 hours at room temperature. After that, the solvent was distilled off under reduced pressure, the resulting residue was dissolved in 3 mL of tetrahydrofuran, and a solution of 45 mg of methoxyamine hydrochloride in 1 mL of water was dripped in at room temperature. After the mixture was stirred for 1.5 hours, whereinto ethyl acetate was added, an organic layer was washed twice with water and then dehydrated and dried with saturated saline followed by anhydrous magnesium sulfate, and the solvent was distilled off under reduced pressure. By washing the resulting solid with a mixed solvent of diisopropylether and acetonitrile, 60 mg of aimed product was obtained as pale yellow solid.

Under this synthetic example, aimed product was isolated as a mixture containing geometrical isomers in which only one component of geometrical isomers derived from olefin was observed and geometrical isomers derived from a structure of iminomethyl were contained at a ratio of 4:1 according to $^1$H NMR measurement.

Melting point: 162.0-168.0° C.

$^1$H NMR (CDCl$_3$, Me$_4$Si, 300 MHz) δ 8.58 (d, J=9.9 Hz, 1H), 7.65-7.80 (m, 3H), 7.50 (d, J=8.4 Hz, 1H), 7.30-7.40 (m, 2H), 7.15 (d, J=1.5 Hz, 2H), 3.80 (s, 3H), 2.52 (s, 3H) only for the major component.

A compound of the present invention can be produced according to the producing methods and examples. Examples of a compound of the present invention produced in the same manner as Synthetic Examples 1 to 14 are shown in Tables 2 and 3, but the present invention is not limited to them.

The notation Ph in these Tables denotes phenyl group, and aromatic heterocycle represented by D-19a, D-38a, and D-41c as well as saturated heterocycle represented by E-1a denote the following structures, respectively, D-19a: 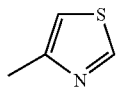

D-38a: 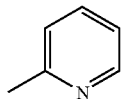

D-41c: 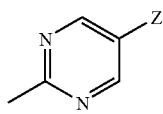

E-1a: 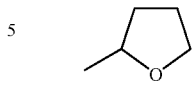

and the notation (C(O)NH(D-41c)Cl) denotes N-(5-chloro-2-pyrimidinyl)carbamoyl group.

Numbers representing the substitution position of substituent $(X)_m$ in the Tables correspond to the positions numbered in the following structural formulae, respectively, and the notation -denotes absence of substitution.

The notation *1 in the Tables denotes "oily or resinous."

In addition, compounds listed in Table 3 have geometrical isomers derived from olefin structure, which represents that these compounds are mixtures containing E-form, Z-form or E-and Z-forms at a given rate, and the notations A, B, and Mx in the Tables denote primary component, secondary component, and a mixture of primary and secondary component in geometrical isomers, respectively; for example, the notation (Mx; 10/1) denotes a mixture containing primary components (A) and secondary components (B), which are calculated from $^1$H NMR data, at a rate of 10:1.

TABLE 2

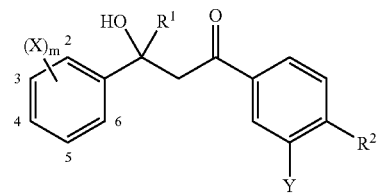

(Table 43)

| No. | $(X)_m$ | $R^1$ | Y | $R^2$ | Melting Point (° C.) |
|---|---|---|---|---|---|
| 1-01 | 3,5-Cl$_2$ | CF$_3$ | — | CN | 100.0-101.5 |
| 1-02 | 3,5-Cl$_2$ | CF$_3$ | — | NO$_2$ | 85.0-86.0 |
| 1-03 | 3,5-Cl$_2$ | CF$_3$ | — | NHC(O)OCH$_3$ | 105.0-107.0 |
| 1-04 | 3,5-Cl$_2$ | CF$_3$ | NO$_2$ | Cl | 111.0-116.0 |
| 1-05 | 3,5-Cl$_2$ | CF$_3$ | CH$_3$ | Cl | 135.0-136.0 |
| 1-06 | 3,5-Cl$_2$ | CF$_3$ | CH$_3$ | Br | 141.0-142.0 |
| 1-07 | 3,5-Cl$_2$ | CF$_3$ | CH$_3$ | OH | 114.0-116.0 |
| 1-08 | 3,5-Cl$_2$ | CF$_3$ | CH$_3$ | C(O)NHCH$_2$(D-38a) | 155.0-156.0 |
| 1-09 | 3,5-Cl$_2$ | CF$_3$ | F | CH$_3$ | 100.0-101.0 |
| 1-10 | 3,5-Cl$_2$ | CF$_3$ | Cl | Cl | 155.0-156.0 |
| 1-11 | 3,5-Cl$_2$ | CF$_3$ | Br | CH$_3$ | 141.0-142.0 |
| 1-12 | 3,5-Cl$_2$ | CF$_3$ | CF$_3$ | F | 75.0-76.0 |
| 1-13 | 3,5-Cl$_2$ | CF$_2$Cl | CH$_3$ | Br | 134.0-136.0 |
| 1-14 | 3,4,5-Cl$_3$ | CF$_3$ | CH$_3$ | Br | *1 |
| 1-15 | 3-CF$_3$ | CF$_3$ | CH$_3$ | Br | *1 |
| 1-16 | 3,5-(CF$_3$)$_2$ | CF$_3$ | CH$_3$ | Br | 97.0-99.0 |

TABLE 3

| No. | $(X)_m$ | $R^1$ | Y | $R^2$ | Melting Point (° C.) |
|---|---|---|---|---|---|
| (Table 44) | | | | | |
| 2-01 | 3,5-Cl$_2$ | CF$_3$ | — | Br | 58.0-60.0 (A) |
| 2-02 | 3,5-Cl$_2$ | CF$_3$ | — | CN | 72.0-76.0 (Mx; 3/1) |
| 2-03 | 3,5-Cl$_2$ | CF$_3$ | — | NO$_2$ | *1 (Mx; 6/1) |
| 2-04 | 3,5-Cl$_2$ | CF$_3$ | — | NHC(O)OCH$_3$ | 129.0-133.0 (Mx; 3/1) |
| 2-05 | 3,5-Cl$_2$ | CF$_3$ | — | C(O)OH | *1 (A) |
| | | | | | 146.5-151.0 (Mx; 10/1) |
| 2-06 | 3,5-Cl$_2$ | CF$_3$ | — | C(O)OCH$_3$ | 65.5-67.5 (Mx; 19/1) |
| 2-07 | 3,5-Cl$_2$ | CF$_3$ | — | C(O)NH$_2$ | 156.0-159.5 (Mx; 10/1) |
| 2-08 | 3,5-Cl$_2$ | CF$_3$ | — | C(O)NHCH$_2$CH$_2$OCH$_3$ | 150.5-153.0 (Mx; 24/1) |
| 2-09 | 3,5-Cl$_2$ | CF$_3$ | — | C(O)NH(E-1a) | 140.5-146.0 (Mx; 12/1) |
| 2-10 | 3,5-Cl$_2$ | CF$_3$ | — | C(O)NH(D-41c)Cl | 71.0-76.0 (Mx; 10/1) |
| 2-11 | 3,5-Cl$_2$ | CF$_3$ | — | C(O)NHCH$_2$(D-19a) | 161.0-165.0 (Mx; 9/1) |
| 2-12 | 3,5-Cl$_2$ | CF$_3$ | — | C(O)NHCH$_2$(D-38a) | *1 (A) |
| 2-13 | 3,5-Cl$_2$ | CF$_3$ | NO$_2$ | Cl | 63.0-66.0 (Mx; 4/1) |
| 2-14 | 3,5-Cl$_2$ | CF$_3$ | CH$_3$ | Cl | 48.0-51.0 (Mx; 9/1) |
| 2-15 | 3,5-Cl$_2$ | CF$_3$ | CH$_3$ | Br | 67.0-69.0 (A) |
| 2-16 | 3,5-Cl$_2$ | CF$_3$ | CH$_3$ | OH | 103.0-106.0 (Mx; 6/1) |
| (Table 45) | | | | | |
| 2-17 | 3,5-Cl$_2$ | CF$_3$ | CH$_3$ | C(O)OH | 123.0-126.5 (Mx; 10/1) |
| 2-18 | 3,5-Cl$_2$ | CF$_3$ | CH$_3$ | C(O)OCH$_3$ | 47.0-49.0 (Mx; 5/1) |
| 2-19 | 3,5-Cl$_2$ | CF$_3$ | CH$_3$ | C(O)NH$_2$ | 116.0-121.0 (Mx; 10/1) |
| 2-20 | 3,5-Cl$_2$ | CF$_3$ | CH$_3$ | C(O)NHC(O)OCH$_3$ | 145.5-149.0 (Mx; 13/1) |
| 2-21 | 3,5-Cl$_2$ | CF$_3$ | CH$_3$ | C(O)NHCH$_2$(D-19a) | *1 (Mx; 9/1) |
| 2-22 | 3,5-Cl$_2$ | CF$_3$ | CH$_3$ | C(O)NHCH$_2$(D-38a) | 115.0-118.0 (Mx; 40/1) |
| 2-23 | 3,5-Cl$_2$ | CF$_3$ | CH$_3$ | C(O)N(C(O)OCH$_3$)CH$_2$(D-38a) | *1 (Mx; 16/1) |
| 2-24 | 3,5-Cl$_2$ | CF$_3$ | CH$_3$ | C(O)NHN(CH$_3$)Ph | 132.5-136.0 (Mx; Unknown) |
| 2-25 | 3,5-Cl$_2$ | CF$_3$ | CH$_3$ | C(O)NHCH$_2$C(O)NHCH$_2$CF$_3$ | 136.5-140.5 (Mx; 9/1) |
| 2-26 | 3,5-Cl$_2$ | CF$_3$ | CH$_3$ | C(O)NHCH=NOCH$_3$ | 162.0-168.0 (A) |
| 2-27 | 3,5-Cl$_2$ | CF$_3$ | F | CH$_3$ | *1 (Mx; 20/1) |
| 2-28 | 3,5-Cl$_2$ | CF$_3$ | Cl | Cl | 67.0-71.0 (Mx; 8/1) |
| 2-29 | 3,5-Cl$_2$ | CF$_3$ | Br | CH$_3$ | 45.0-47.5 (Mx; 3/1) |
| 2-30 | 3,5-Cl$_2$ | CF$_3$ | CF$_3$ | F | *1 (Mx; 5.5/1) |
| 2-31 | 3,5-Cl$_2$ | CF$_2$Cl | CH$_3$ | Br | *1 (A) |
| 2-32 | 3,4,5-Cl$_2$ | CF$_3$ | CH$_3$ | Br | *1 (A) |
| | | | | | 167.0-168.0 (B) |
| 2-33 | 3-CF$_3$ | CF$_3$ | CH$_3$ | Br | *1 (A) |
| | | | | | 77.0-79.0 (B) |
| 2-34 | 3,5-(CF$_3$)$_2$ | CF$_3$ | CH$_3$ | Br | *1 (A) |
| | | | | | 69.0-71.0 (B) |

Table 4 shows $^1$H NMR data for the primary (A) and secondary (B) components of compounds without description of melting point replaced by the notation *1 as well as the present invention compounds No. 2-32 to 2-34 listed in Tables 2 and 3.

The notation (i) in the Tables denotes the condition that measurement was conducted at 300 MHz using tetramethylsilane as a standard substance in deuterated chloroform solvent (CDCl$_3$, Me$_4$Si, 300 MHz), while the notation (ii) denotes the measurement condition (CDCl$_3$, Me$_4$Si, 400 MHz).

For mixed geometrical isomers, $^1$H NMR data are shown only for the primary component.

TABLE 4

| No. | $^1$H NMR |
|---|---|
| (Table 46) | |
| 1-14 | (i) δ 7.55-7.80 (m, 5 H), 5.73 (s, 1 H), 3.80 (d, J = 18.0 Hz, 1 H), 3.64 (d, J = 18.0 Hz, 1 H), 2.49 (s, 3 H). |
| 1-15 | (i) δ 7.40-8.00 (m, 7 H), 5.75 (s, 1 H), 3.93 (d, J = 17.4 Hz, 1 H), 3.66 (d, J = 17.4 Hz, 1 H), 2.46 (s, 3 H). |
| 2-03 | (ii) δ 8.03 (d, J = 8.4 Hz, 2 H), 7.98 (d, J = 8.4 Hz, 2 H), 7.39 (q, J = 1.5 Hz, 1 H), 7.35 (t, J = 1.8 Hz, 1 H), 7.15 (d, J = 1.8 Hz, 2 H). |
| 2-05 | (i) δ 8.18 (d, J = 8.5 Hz, 2 H), 7.91 (d, J = 8.5 Hz, 2 H), 7.40 (s, 1 H), 7.34 (s, 1 H), 7.16 (s, 2 H). |

TABLE 4-continued

| No. | $^1$H NMR |
|---|---|
| 2-12 | (i) δ 8.56 (d, J = 5.1 Hz, 1 H), 7.85-8.10 (m, 5 H), 7.65-7.75 (m, 1 H), 7.15-7.50 (m, 6 H), 4.75 (d, J = 4.5 Hz, 2 H). |
| 2-21 | (i) δ 8.77 (d, J = 1.5 Hz, 1 H), 7.60-7.70 (m, 2 H), 7.30-7.50 (m, 4 H), 7.14 (s, 2 H), 6.62 (brs, 1 H), 4.77 (d, J = 5.4 Hz, 2 H), 2.45 (s, 3 H). |
| 2-23 | (i) δ 8.57 (d, J = 4.8 Hz, 1 H), 7.65-7.75 (m, 2 H), 7.10-7.45 (m, 8 H), 5.22 (s, 2 H), 3,56 (s, 3 H), 2.41 (s, 3 H). |
| | (Table 47) |
| 2-27 | (ii) δ 7.52 (dd, J = 7.9, 1.6 Hz, 1 H), 7.47 (dd, J = 9.9, 1.6 Hz, 1 H), 7.35 (q, J = 1.5 Hz, 1 H), 7.34 (t, J = 1.8 Hz, 1 H), 7.28 (t, J = 7.9 Hz, 1 H), 7.16 (d, J = 1.8 Hz, 2 H), 2.34 (d, J = 2.0 Hz, 3 H). |
| 2-30 | (ii) δ 6 8.00-8.10 (m, 2 H), 7.35 (t, J = 1.8 Hz, 1 H), 7.33 (q, J =1.5 Hz, 1 H), 7.30 (t, J = 9.2 Hz, 1 H), 7.15 (d, J = 1.8 Hz, 2 H). |
| 2-31 | (i) δ 7.15-7.70 (m, 7 H), 2.44 (s, 3 H). |
| 2-32 (A) | (i) δ 7.20-7.70 (m, 6 H), 2.45 (s, 3 H). |
| (B) | (i) δ 7.50-7.85 (m, 5 H), 6.84 (s, 1 H), 2.50 (s, 3 H). |
| 2-33 (A) | (i) δ 7.30-7.65 (m, 8 H), 2.41 (s, 3 H). |
| (B) | (i) δ 7.55-7.90 (m, 7 H), 6.85 (s, 1 H), 2.50 (s, 3 H). |
| 2-34 (A) | (i) δ 7.40-7.90 (m, 7 H), 2.43 (s, 3 H). |
| (B) | (i) δ 7.55-8.05 (m, 6 H), 6.92 (s, 1 H), 2.51 (s, 3 H). |

Reference Example 4-(5-(3,5-Dichlorophenyl)-5-trifluoromethyl-4,5-dihydroisooxazol-3-yl)-2-methyl-N-(2-pyrimidinyl) benzoic acid amide Step 1; Production of 3-(4-bromophenyl)-5-(3,5-dichlorophenyl)-5-trifluoromethyl-4,5-dihydroisooxazol To a solution of 430 mg (1.0 mmol) of 1-(4-bromophenyl)-3-(3,5-dichlorophenyl)-4,4,4-trifluoro-2-butene-1-one in 10 mL of 1,2-dimethoxyethane, 2 mL of aqueous solution containing 140 mg (2.0 mmol) of hydroxylamine hydrochloride and 160 mg (4.0 mmol) of sodium hydroxide was dripped at room temperature. After stirring for 2-hour at the same temperature, 80 mL of ethyl acetate was added into the reaction solution, the mixture was washed with 50 mL of diluted hydrochloric acid, an organic layer was dehydrated and dried with saturated saline followed by anhydrous magnesium sulfate, and the solvent was distilled off under reduced pressure. By crystallizing the resulting residue with cold hexane, 360 mg (0.8 mmol; yield, 80.9%) of aimed product was obtained as pale yellow solid.

Melting point: 122 to 124° C.
$^1$H NMR (CDCl$_3$, Me$_4$Si, 300 MHz) δ 7.50-7.60 (m, 6H), 7.40-7.45 (m, 1H), 4.07 (d, J=17.4 Hz, 1H), 3.68 (d, J=17.4 Hz, 1H).

Step 2; Production of 4-(5-(3,5-dichlorophenyl)-5-trifluoromethyl-4,5-dihydroisooxazol-3-yl)-2-methylbenzoyl=chloride To a solution of 18.1 g of 3-(4-bromo-3-methylphenyl)-5-(3,5-dichlorophenyl)-5-trifluoromethyl-4,5-dihydroisooxazol and 3.94 g of sodium acetate in 42 mL of 1,2-dimethoxyethane and 42 mL of water in an autoclave, 0.42 g of triphenylphosphine and 0.09 g of palladium(II) acetate were added, the mixture was stirred for 7 hours at 110° C. in an atmosphere of carbon monoxide at 1.5 MPa. After the completion of reaction, the temperature was cooled to room temperature to separate solid matter by filtration and then the solid matter was put into 100 mL of ethyl acetate. An organic layer was washed with 1% sodium hydrogen carbonate solution (70 mL×2) followed by 1N hydrochloride (55 mL×1) and dried with saturated saline followed by substitution of the solvent with toluene. 2 drops of N,N-dimethylformamide was added to the toluene solution, 6.0 g of thionyl chloride was dripped while stirring at 80° C. followed by further 1.5-hour stir at the same temperature. After the completion of reaction, insoluble matter was separated by filtration, and the solvent was distilled off under reduced pressure until the total volume was reduced to about ⅓. Then, 50 mL of hexane was dripped slowly while stirring at 60° C., and after the end of dripping, the temperature was cooled to room temperature with stirring followed by further 1-hour stir at room temperature. Precipitated crystal was separated by filtration and dried to obtain 13.4 g of aimed product as white crystal.

Melting point: 140.5 to 143.0° C.
$^1$H NMR (CDCl$_3$, Me$_4$Si, 300 MHz) δ 8.25 (d, J=8.7 Hz, 1H), 7.64 (d, J=8.7 Hz, 1H), 7.59 (s, 1H), 7.51 (s, 2H), 7.43 (s, 1H), 4.11 (d, J=17.4 Hz, 1H), 3.73 (d, J=17.4 Hz, 1H), 2.60 (s, 3H).

Step 3; Production of 4-(5-(3,5-dichlorophenyl)-5-trifluoromethyl-4,5-dihydroisooxazol-3-yl)-2-methyl-N-(2-pyrimidinyl)benzoic acid amide To a solution of 0.52 g of 2-aminopyrimidine in 40 mL of 1,2-dichloroethane, 0.51 g of pyridine was added at room temperature followed by dripping of a solution of 2.0 g of 4-(5-(3,5-dichlorophenyl)-5-trifluoromethyl-4,5-dihydroisooxazol-3-yl)-2-methylbenzoyl=chloride in 20 mL of 1,2-dichloroethane, and the mixture was stirred for 18 hours at room temperature. After the completion of reaction, the solvent was distilled off under reduced pressure, and the resulting residue was purified using silica gel column chromatography that was eluted with ethyl acetate to obtain 1.86 g of aimed product as white solid.

Melting point: 98.0 to 100.0° C.
$^1$H NMR (CDCl$_3$, Me$_4$Si, 300 MHz) δ 8.64 (d, J=4.8 Hz, 2H), 8.46 (brs, 1H), 7.40-7.60 (m, 6H), 7.08 (t, J=4.8 Hz, 1H), 4.10 (d, J=17.2 Hz, 1H), 3.72 (d, J=17.2 Hz, 1H), 2.57 (s, 3H).

INDUSTRIAL APPLICABILITY

The 1,3-Bis(substituted phenyl)-3-substituent-3-hydroxypropan-1-one compound and the 1,3-bis(substituted phenyl)-3-substituent-2-propen-1-one compound relating to the present invention are useful compounds as a process intermediate of an isoxazoline-substituted benzamide compound with excellent pest control effect.

The invention claimed is:
1. A 1,3-bis(substituted phenyl)-3-substituent-3-hydroxypropan-1-one compound or salt thereof represented by general formula (1):

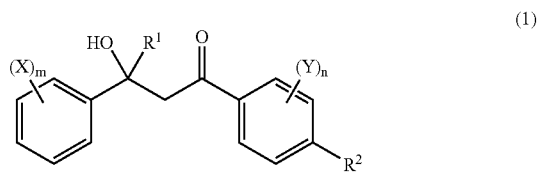

(where, X represents halogen atom, or $C_1$-$C_4$ haloalkyl group, and when m represents 2 or 3, each X can be identical with or different from each other;
Y represents halogen atom, nitro group, $C_1$-$C_4$ alkyl group, or $C_1$-$C_4$ haloalkyl group,
$R^1$ represents $C_1$-$C_4$ haloalkyl group;

$R^2$ represents methyl group, halogen atom, cyano group, nitro group, —NH$_2$, —N(R$^5$)R$^4$, —OH, —OR$^3$, benzyloxy group, —OSO$_2$R$^3$, phenylsulfonyloxy group, phenylsulfonyloxy group substituted by (Z)$_{p1}$, —C(O)OH, —C(O)OR$^3$, —C(O)NH$_2$, —C(O)N(R$^b$)R$^a$, or —C(S)N(R$^b$)R$^a$;

$R^3$ represents C$_1$-C$_6$ alkyl group, C$_1$-C$_4$ alkoxy(C$_1$-C$_4$) alkyl group, C$_1$-C$_6$ haloalkyl group, or C$_1$-C$_3$ haloalkoxy (C$_1$-C$_3$)haloalkyl group;

$R^4$ represents C$_1$-C$_6$ alkyl group, —CHO, C$_1$-C$_6$ alkylcarbonyl group, C$_1$-C$_6$ haloalkylcarbonyl group, C$_1$-C$_6$ alkoxycarbonyl group, C$_1$-C$_6$ alkylthiocarbonyl group, C$_1$-C$_6$ alkoxythiocarbonyl group, C$_1$-C$_6$ alkyldithiocarbonyl group, C$_1$-C$_6$ alkylsulfonyl group, or C$_1$-C$_6$ haloalkylsulfonyl group;

$R^5$ represents hydrogen atom or C$_1$-C$_6$ alkyl group;

$R^a$ represents C$_1$-C$_6$ alkyl group, (C$_1$-C$_6$) alkyl group substituted arbitrarily by R$^6$, C$_3$-C$_6$ cycloalkyl group, C$_3$-C$_6$ alkenyl group, C$_3$-C$_6$ haloalkenyl group, C$_3$-C$_6$ alkynyl group, —N(R$^9$)R$^8$, —C(O)OR$^7$, —C(O)NH$_2$, —C(O)NHR$^7$, —C(R$^{15}$)=NOR$^{14}$, phenyl group, phenyl group substituted by (Z)$_{p1}$, D-5, D-7, D-10, D-11, D-12, D-14, D-15, D-18, D-31, D-32, D-38, D-39, D-41, D-42, D-44, E-1, E-2, E-3, E-4, or E-7;

$R^b$ represents hydrogen atom, C$_1$-C$_6$ alkyl group, C$_1$-C$_4$ alkoxy(C$_1$-C$_4$)alkyl group, cyano(C$_1$-C$_6$)alkyl group, C$_3$-C$_6$ alkynyl group, —C(O)R$^7$, or —C(O)OR$^7$;

$R^6$ represents halogen atom, cyano group, C$_3$-C$_6$ cycloalkyl group, C$_3$-C$_6$ halocycloalkyl group, C$_1$-C$_6$ alkoxy group, C$_1$-C$_6$ haloalkoxy group, C$_1$-C$_6$ alkylthio group, C$_1$-C$_6$ haloalkylthio group, C$_1$-C$_6$ alkylsulfinyl group, C$_1$-C$_6$ haloalkylsulfinyl group, C$_1$-C$_6$ alkylsulfonyl group, C$_1$-C$_6$ haloalkylsulfonyl group, —C(O)R$^{12}$, —C(O)OR$^{12}$, —C(O)NH$_2$, —C(O)N(R$^{13}$)R$^{12}$, —C(S)NH$_2$, —C(S)N(R$^{13}$)R$^{12}$, —C(R$^{15}$)=NOH, —C(R$^{15}$)=NOR$^{14}$, phenyl group, phenyl group substituted by (Z)$_{p1}$, D-1 to D-46, or E-1 to E-8;

the D-1 to D-46 represent respective aromatic heterocycles as shown in the following structural formulae:

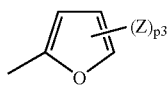

D-1

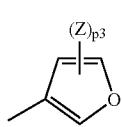

D-2

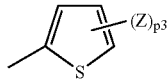

D-3

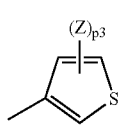

D-4

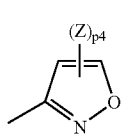

D-5

-continued

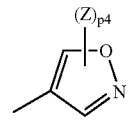

D-6

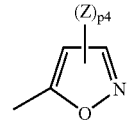

D-7

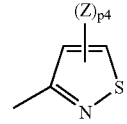

D-8

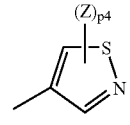

D-9

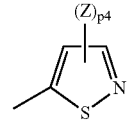

D-10

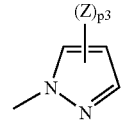

D-11

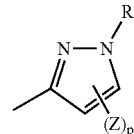

D-12

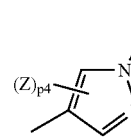

D-13

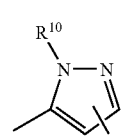

D-14

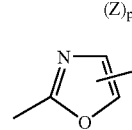

D-15

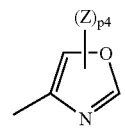

D-16

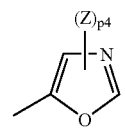

D-17

-continued
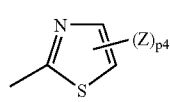 D-18
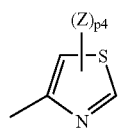 D-19
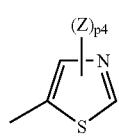 D-20
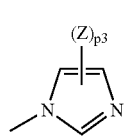 D-21
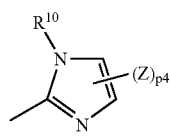 D-22
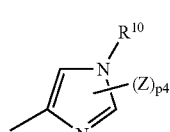 D-23
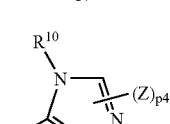 D-24
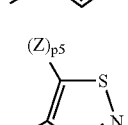 D-25
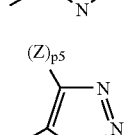 D-26
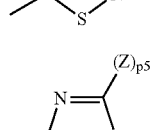 D-27
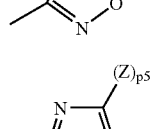 D-28
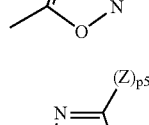 D-29
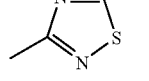
-continued
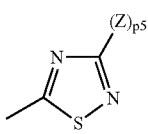 D-30
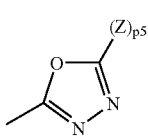 D-31
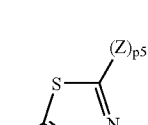 D-32
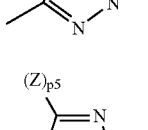 D-33
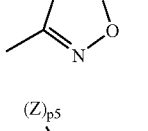 D-34
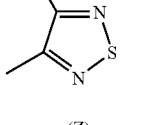 D-35
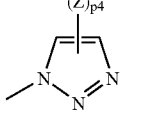 D-36
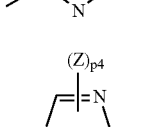 D-37
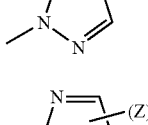 D-38
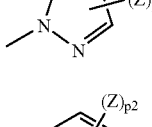 D-39
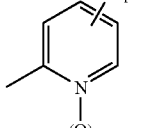 D-40
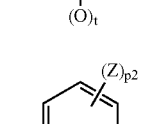
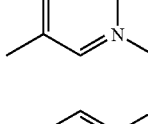

-continued

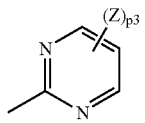
D-41

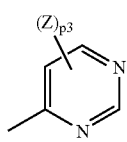
D-42

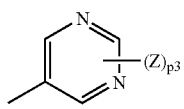
D-43

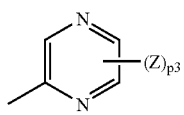
D-44

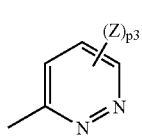
D-45

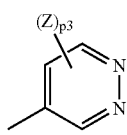
D-46

Z represents halogen atom, cyano group, nitro group, $C_1$-$C_6$ alkyl group, $C_1$-$C_6$ haloalkyl group, $C_1$-$C_6$ alkoxy group, $C_1$-$C_6$ haloalkoxy group, $C_1$-$C_6$ alkylsulfonyl group, $C_1$-$C_6$ haloalkylsulfonyl group, $C_1$-$C_6$ alkoxycarbonyl group, —C(O)NH$_2$, $C_1$-$C_6$ alkylaminocarbonyl group, di($C_1$-$C_6$ alkyl)aminocarbonyl group, —C(S)NH$_2$, —S(O)$_2$NH$_2$, $C_1$-$C_6$ alkylaminosulfonyl group or di($C_1$-$C_6$ alkyl)aminosulfonyl group, and when p1, p2, p3, or p4 represents 2 or higher integer, each Z can be identical with or different from each other;

E-1 to E-8 represent respective saturated heterocycles as shown in the following structural formulae:

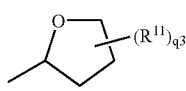
E-1

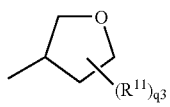
E-2

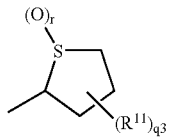
E-3

-continued

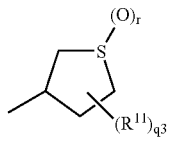
E-4

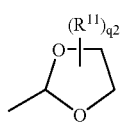
E-5

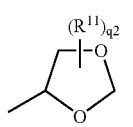
E-6

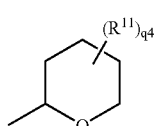
E-7

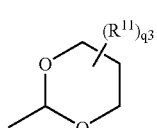
E-8

$R^7$ represents $C_1$-$C_6$ alkyl group, $C_1$-$C_6$ haloalkyl group, $C_1$-$C_6$ alkoxy($C_1$-$C_4$)alkyl group, $C_1$-$C_6$ alkylthio($C_1$-$C_4$)alkyl group, $C_3$-$C_8$ cycloalkyl group, $C_3$-$C_6$ alkenyl group, or $C_3$-$C_6$ alkynyl group;

$R^8$ represents $C_1$-$C_6$ haloalkyl group, —C(O)$R^{12}$, —C(O)O$R^{12}$, phenyl group, phenyl group substituted by $(Z)_{p1}$, D-3, D-4, D-18, D-38, D-41, D-42, D-44, or D-45;

$R^9$ represents hydrogen atom, $C_1$-$C_6$ alkyl group, or $C_3$-$C_6$ alkynyl group;

$R^{10}$ represents $C_1$-$C_6$ alkyl group, phenyl group, or phenyl group substituted by $(Z)_{p1}$;

$R^{11}$ represents $C_1$-$C_4$ alkyl group, when q1, q2, q3, or q4 represents 2 or higher integer, each $R^{11}$ can be identical with or different from each other, and two $R^{11}$s substituting on the same carbon atom indicate that the two $R^{11}$s can form an oxo ring together;

$R^{12}$ represents $C_1$-$C_6$ alkyl group, $C_1$-$C_6$ haloalkyl group, $C_3$-$C_6$ cycloalkyl($C_1$-$C_4$)alkyl group, $C_3$-$C_6$ cycloalkyl group, $C_3$-$C_6$ alkenyl group, or $C_3$-$C_6$ alkynyl group;

$R^{13}$ represents hydrogen atom or $C_1$-$C_6$ alkyl group;

$R^{14}$ represents $C_1$-$C_6$ alkyl group or $C_1$-$C_6$ haloalkyl group;

$R^{15}$ represents hydrogen atom or $C_1$-$C_6$ alkyl group;

m represents an integer of 1 to 3;

n represents an integer of 0 or 1;

p1 represents an integer of 1 to 5;

p2 represents an integer of 0 to 4;

p3 represents an integer of 0 to 3;

p4 represents an integer of 0 to 2;

p5 represents an integer of 0 or 1;

q2 represents an integer of 0 to 5;

q3 represents an integer of 0 to 7;

q4 represents an integer of 0 to 9;

r represents an integer of 0 to 2; and t represents an integer of 0 or 1).

2. The 1,3-bis(substituted phenyl)-3-substituent-3-hydroxypropan-1-one compound or salt thereof according to claim 1, which is represented by the formula, where $R^2$ represents halogen atom, cyano group, nitro group, —$NH_2$, —$NHR^4$, —OH, —$OR^3$, benzyloxy group, —$OSO_2R^3$, phenylsulfonyloxy group, paratoluenesulfonyloxy group, —C(O)OH, —C(O)$OR^3$, —C(O)$NH_2$, or —C(O)N($R^b$)$R^a$;
$R^3$ represents $C_1$-$C_4$ alkyl group or $C_1$-$C_4$ haloalkyl group;
$R^4$ represents $C_1$-$C_4$ alkyl group, —CHO, $C_1$-$C_4$ alkylcarbonyl group, or $C_1$-$C_4$ alkoxycarbonyl group;
$R^a$ represents $C_1$-$C_4$ alkyl group, ($C_1$-$C_4$) alkyl group substituted arbitrarily by $R^6$, —N($R^9$)$R^8$, —C(O)$R^7$, —C(O)$NH_2$, —C(O)$NHR^7$, —C($R^{15}$)=$NOR^{14}$, phenyl group, phenyl group substituted by $(Z)_{p1}$, D-5, D-7, D-10, D-11, D-12, D-14, D-15, D-18, D-31, D-32, D-38, D-39, D-41, D-42, D-44, E-1, or E-7;
$R^b$ represents hydrogen atom, $C_1$-$C_6$ alkyl group, $C_1$-$C_4$ alkoxy($C_1$-$C_4$)alkyl group, cyano($C_1$-$C_4$)alkyl group, $C_3$-$C_6$ alkynyl group, —C(O)$R^7$, or —C(O)$OR^7$;
$R^6$ represents halogen atom, cyano group, $C_3$-$C_6$ cycloalkyl group, $C_1$-$C_4$ alkoxy group, $C_1$-$C_4$ haloalkoxy group, $C_1$-$C_4$ alkylthio group, $C_1$-$C_4$ haloalkylthio group, $C_1$-$C_4$ alkylsulfonyl group, $C_1$-$C_4$ haloalkylsulfonyl group, —C(O)N($R^{13}$)$R^{12}$, —C($R^{15}$)=NOH, —C($R^{15}$)=$NOR^{14}$, phenyl group, phenyl group substituted by $(Z)_{p1}$, D-11 to D-14, D-18, D-19, D-25, D-26, D-31, D-32, D-36, D-38, D-41, D-44, D-45, E-1, E-2, or E-5;
Z represents halogen atom, cyano group, nitro group, $C_1$-$C_4$ alkyl group, $C_1$-$C_4$ haloalkyl group, $C_1$-$C_4$ alkoxy group, $C_1$-$C_4$ haloalkoxy group, $C_1$-$C_4$ alkylsulfonyl group, or $C_1$-$C_4$ haloalkylsulfonyl group, and when p1, p2, p3, or p4 represents 2 or higher integer, each Z can be identical with or different from each other;
$R^7$ represents $C_1$-$C_6$ alkyl group, $C_1$-$C_6$ haloalkyl group, $C_1$-$C_6$ alkoxy($C_1$-$C_4$)alkyl group, $C_1$-$C_6$ alkylthio($C_1$-$C_4$)alkyl group, $C_3$-$C_8$ cycloalkyl group, $C_3$-$C_6$ alkenyl group, or $C_3$-$C_6$ alkynyl group;
$R^8$ represents $C_1$-$C_4$ haloalkyl group, —C(O)$R^{12}$, —C(O)$OR^{12}$, phenyl group, phenyl group substituted by $(Z)_{p1}$, D-3, D-4, D-18, D-38, D-41, D-42, D-44, or D-45;
$R^9$ represents hydrogen atom or $C_1$-$C_6$ alkyl group;
$R^{10}$ represents $C_1$-$C_4$ alkyl group;
$R^{11}$ represents $C_1$-$C_4$ alkyl group, when q1, q2, q3, or q4 represents 2 or higher integer, each $R^{11}$ can be identical with or different from each other, and two $R^{11}$s substituting on the same carbon atom indicate that the two $R^{11}$s can form an oxo ring together;
$R^{12}$ represents $C_1$-$C_4$ alkyl group, $C_1$-$C_4$ haloalkyl group, $C_3$-$C_6$ cycloalkyl($C_1$-$C_4$) alkyl group, $C_3$-$C_6$ cycloalkyl group, $C_3$-$C_6$ alkenyl group, or $C_3$-$C_6$ alkynyl group;
$R^{13}$ represents hydrogen atom or $C_1$-$C_4$ alkyl group;
$R^{14}$ represents $C_1$-$C_4$ alkyl group or $C_1$-$C_4$ haloalkyl group; and
$R^{15}$ represents hydrogen atom or $C_1$-$C_4$ alkyl group.

3. A 1,3-bis(substituted phenyl)-3-substituent-2-propen-1-one compound or salt thereof represented by general formula (2):

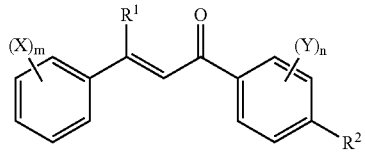

(2)

(where, X represents halogen atom, cyano group, nitro group, —$SF_5$, $C_1$-$C_6$ alkyl group, $C_1$-$C_6$ haloalkyl group, hydroxy($C_1$-$C_6$)haloalkyl group, $C_1$-$C_6$ alkoxy($C_1$-$C_6$)haloalkyl group, $C_1$-$C_6$ haloalkoxy($C_1$-$C_6$)haloalkyl group, $C_3$-$C_8$ halocycloalkyl group, —$OR^3$, —$OSO_2R^3$, or —S(O)$_rR^3$, and when m represents 2 or higher integer, each X can be identical with or different from each other;
Y represents halogen atom, cyano group, nitro group, $C_1$-$C_4$ alkyl group, $C_1$-$C_4$ haloalkyl group, $C_1$-$C_4$ alkoxy group, $C_1$-$C_4$ haloalkoxy group, $C_1$-$C_6$ alkylthio group, $C_1$-$C_6$ haloalkylthio group, $C_1$-$C_6$ alkylsulfonyl group, $C_1$-$C_6$ haloalkylsulfonyl group, —$NH_2$ or —N($R^5$)$R^4$, and when n represents 2 or higher integer, each Y can be identical with or different from each other;
$R^1$ represents $C_1$-$C_6$ haloalkyl group or $C_3$-$C_8$ halocycloalkyl group;
$R^2$ represents methyl group, halogen atom, cyano group, nitro group, —$NH_2$, —N($R^5$)$R^4$, —OH, —$OR^3$, benzyloxy group, —$OSO_2R^3$, phenylsulfonyloxy group, phenylsulfonyloxy group substituted by $(Z)_{p1}$, —C(O)OH, —C(O)$OR^3$, —C(O)$NH_2$, —C(O)N($R^b$)$R^a$ or —C(S)N($R^b$)$R^a$;
$R^3$ represents $C_1$-$C_6$ alkyl group, $C_1$-$C_4$ alkoxy($C_1$-$C_4$) alkyl group, $C_1$-$C_6$ haloalkyl group or $C_1$-$C_3$ haloalkoxy($C_1$-$C_3$)haloalkyl group;
$R^4$ represents $C_1$-$C_6$ alkyl group, —CHO, $C_1$-$C_6$ alkylcarbonyl group, $C_1$-$C_6$ haloalkylcarbonyl group, $C_1$-$C_6$ alkoxycarbonyl group, $C_1$-$C_6$ alkylthiocarbonyl group, $C_1$-$C_6$ alkoxythiocarbonyl group, $C_1$-$C_6$ alkyldithiocarbonyl group, $C_1$-$C_6$ alkylsulfonyl group, or $C_1$-$C_6$ haloalkylsulfonyl group;
$R^5$ represents hydrogen atom or $C_1$-$C_6$ alkyl group;
$R^a$ represents $C_1$-$C_6$ alkyl group, ($C_1$-$C_6$) alkyl group substituted arbitrarily by $R^6$, $C_3$-$C_6$ cycloalkyl group, $C_3$-$C_6$ alkenyl group, $C_3$-$C_6$ haloalkenyl group, $C_3$-$C_6$ alkynyl group, —N($R^9$)$R^8$, —C(O)$OR^7$, —C(O)$NH_2$, —C(O)$NHR^7$, —C($R^{15}$)=$NOR^{14}$, phenyl group, phenyl group substituted by $(Z)_{p1}$, D-5, D-7, D-10, D-11, D-12, D-14, D-15, D-18, D-31, D-32, D-38, D-39, D-41, D-42, D-44, E-1, E-2, E-3, E-4, or E-7;
$R^b$ represents hydrogen atom, $C_1$-$C_6$ alkyl group, $C_1$-$C_4$ alkoxy($C_1$-$C_4$)alkyl group, cyano($C_1$-$C_6$)alkyl group, $C_3$-$C_6$ alkynyl group, —C(O)$R^7$, or —C(O)$OR^7$;
$R^6$ represents halogen atom, cyano group, $C_3$-$C_6$ cycloalkyl group, $C_3$-$C_6$ halocycloalkyl group, $C_1$-$C_6$ alkoxy group, $C_1$-$C_6$ haloalkoxy group, $C_1$-$C_6$ alkylthio group, $C_1$-$C_6$ haloalkylthio group, $C_1$-$C_6$ alkylsulfinyl group, $C_1$-$C_6$ haloalkylsulfinyl group, $C_1$-$C_6$ alkylsulfonyl group, $C_1$-$C_6$ haloalkylsulfonyl group, —C(O)$R^{12}$, —C(O)$OR^{12}$, —C(O)$NH_2$, —C(O)N($R^{13}$)$R^{12}$, —C(S)$NH_2$, —C(S)N($R^{13}$)$R^{12}$, —C($R^{15}$)=NOH, —C($R^{15}$)=$NOR^{14}$, phenyl group, phenyl group substituted by $(Z)_{p1}$, D-1 to D-46, or E-1 to E-8;
the D-1 to D-46 represent respective aromatic heterocycles as shown in the following structural formulae:

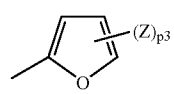

D-1

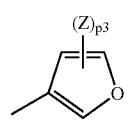

D-2

-continued
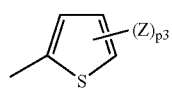
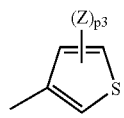
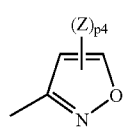
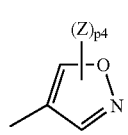
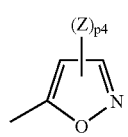
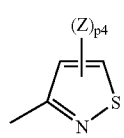
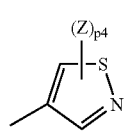
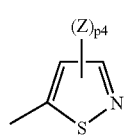
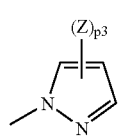
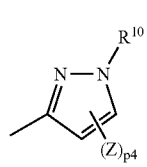
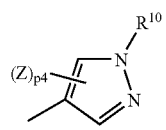
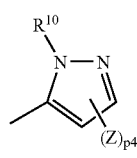
-continued
D-3
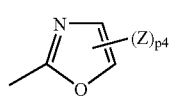
D-4
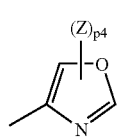
D-5
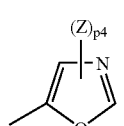
D-6
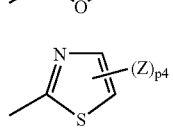
D-7
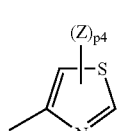
D-8
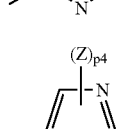
D-9
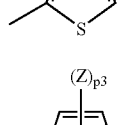
D-10
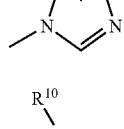
D-11
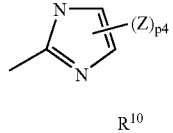
D-12
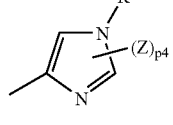
D-13
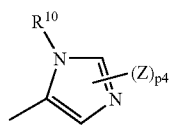
D-14
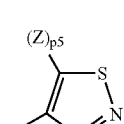
D-15
D-16
D-17
D-18
D-19
D-20
D-21
D-22
D-23
D-24
D-25
D-26
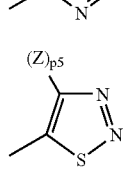

-continued

D-27 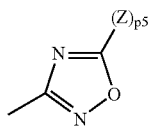

D-28 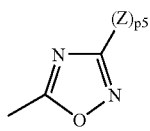

D-29 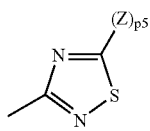

D-30 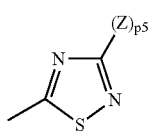

D-31 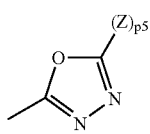

D-32 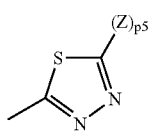

D-33 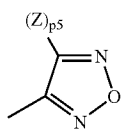

D-34 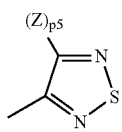

D-35 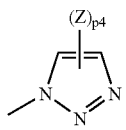

D-36 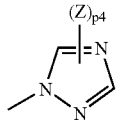

D-37 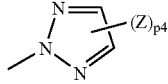

-continued

D-38 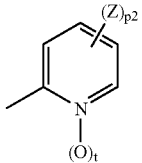

D-39 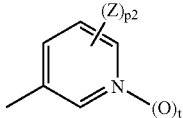

D-40 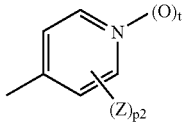

D-41 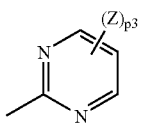

D-42 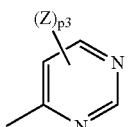

D-43 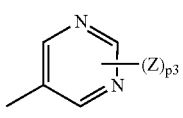

D-44 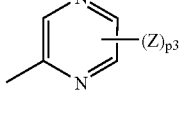

D-45 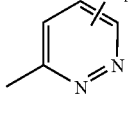

D-46 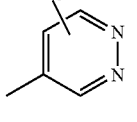

Z represents halogen atom, cyano group, nitro group, $C_1$-$C_6$ alkyl group, $C_1$-$C_6$ haloalkyl group, $C_1$-$C_6$ alkoxy group, $C_1$-$C_6$ haloalkoxy group, $C_1$-$C_6$ alkylsulfonyl group, $C_1$-$C_6$ haloalkylsulfonyl group, $C_1$-$C_6$ alkoxycarbonyl group, —C(O)NH$_2$, $C_1$-$C_6$ alkylaminocarbonyl group, di($C_1$-$C_6$ alkyl)aminocarbonyl group, —C(S)NH$_2$, —S(O)$_2$NH$_2$, $C_1$-$C_6$ alkylaminosulfonyl group or di($C_1$-$C_6$ alkyl)aminosulfonyl group, and when p1, p2, p3, or p4 represents 2 or higher integer, each Z can be identical with or different from each other;

the E-1 to E-8 represent respective saturated heterocycles as shown in the following structural formulae:

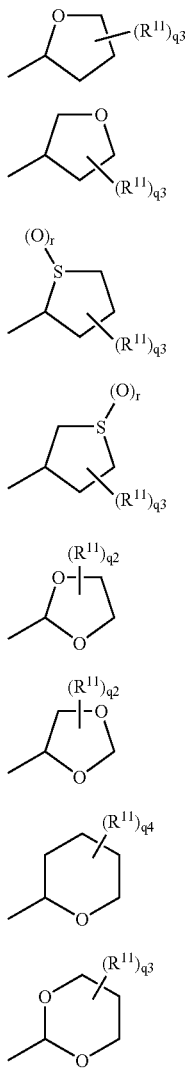

E-1
E-2
E-3
E-4
E-5
E-6
E-7
E-8

R$^7$ represents C$_1$-C$_6$ alkyl group, C$_1$-C$_6$ haloalkyl group, C$_1$-C$_6$ alkoxy(C$_1$-C$_4$)alkyl group, C$_1$-C$_6$ alkylthio(C$_1$-C$_4$)alkyl group, C$_3$-C$_8$ cycloalkyl group, C$_3$-C$_6$ alkenyl group, or C$_3$-C$_6$ alkynyl group;

R$^8$ represents C$_1$-C$_6$ haloalkyl group, —C(O)R$^{12}$, —C(O)OR$^{12}$, phenyl group, phenyl group substituted by (Z)$_{p1}$, D-3, D-4, D-18, D-38, D-41, D-42, D-44, or D-45;

R$^9$ represents hydrogen atom, C$_1$-C$_6$ alkyl group, or C$_3$-C$_6$ alkynyl group;

R$^{10}$ represents C$_1$-C$_6$ alkyl group, phenyl group, or phenyl group substituted by (Z)$_{p1}$;

R$^{11}$ represents C$_1$-C$_4$ alkyl group, when q1, q2, q3, or q4 represents 2 or higher integer, each R$^{11}$ can be identical with or different from each other, and two R$^{11}$s substituting on the same carbon atom indicate that the two R$^{11}$s can form an oxo ring together;

R$^{12}$ represents C$_1$-C$_6$ alkyl group, C$_1$-C$_6$ haloalkyl group, C$_3$-C$_6$ cycloalkyl(C$_1$-C$_4$)alkyl group, C$_3$-C$_6$ cycloalkyl group, C$_3$-C$_6$ alkenyl group, or C$_3$-C$_6$ alkynyl group;

R$^{13}$ represents hydrogen atom or C$_1$-C$_6$ alkyl group;

R$^{14}$ represents C$_1$-C$_6$ alkyl group or C$_1$-C$_6$ haloalkyl group;

R$^{15}$ represents hydrogen atom or C$_1$-C$_6$ alkyl group;

m represents an integer of 1 to 5;
n represents an integer of 0 to 4;
p1 represents an integer of 1 to 5;
p2 represents an integer of 0 to 4;
p3 represents an integer of 0 to 3;
p4 represents an integer of 0 to 2;
p5 represents an integer of 0 or 1;
q2 represents an integer of 0 to 5;
q3 represents an integer of 0 to 7;
q4 represents an integer of 0 to 9;
r represents an integer of 0 to 2; and
t represents an integer of 0 or 1).

4. The 1,3-bis(substituted phenyl)-3-substituent-2-propen-1-one compound or salt thereof according to claim 3 which is represented by the formula, where X represents halogen atom or C$_1$-C$_4$ haloalkyl group, and when m represents 2 or 3, each X can be identical with or different from each other;
Y represents halogen atom, nitro group, C$_1$-C$_4$ alkyl group, or C$_1$-C$_4$ haloalkyl group;
R$^1$ represents C$_1$-C$_4$ haloalkyl group;
m represents an integer of 1 to 3; and
n represents 0 or 1.

5. The 1,3-bis(substituted phenyl)-3-substituent-2-propen-1-one compound or salt thereof according to claim 4 which is represented by the formula, where R$^2$ represents halogen atom, cyano group, nitro group, —NH$_2$, —NHR$^4$, —OH, —OR$^3$, benzyloxy group, —OSO$_2$R$^3$, phenylsulfonyloxy group, paratoluenesulfonyloxy group, —C(O)OH, —C(O)OR$^3$, —C(O)NH$_2$, or —C(O)N(R$^b$)R$^a$;

R$^3$ represents C$_1$-C$_4$ alkyl group or C$_1$-C$_4$ haloalkyl group;
R$^4$ represents C$_1$-C$_4$ alkyl group, —CHO, C$_1$-C$_4$ alkylcarbonyl group, or C$_1$-C$_4$ alkoxycarbonyl group;
R$^a$ represents C$_1$-C$_4$ alkyl group, (C$_1$-C$_4$) alkyl group substituted arbitrarily by R$^6$, —N(R$^9$)R$^8$, —C(O)OR$^7$, —C(O)NH$_2$, —C(O)NHR$^7$, —C(R$^{15}$)=NOR$^{14}$, phenyl group, phenyl group substituted by (Z)$_{p1}$, D-5, D-7, D-10, D-11, D-12, D-14, D-15, D-18, D-31, D-32, D-38, D-39, D-41, D-42, D-44, E-1, or E-7;
R$^b$ represents hydrogen atom, C$_1$-C$_6$ alkyl group, C$_1$-C$_4$ alkoxy(C$_1$-C$_4$)alkyl group, cyano(C$_1$-C$_4$)alkyl group, C$_3$-C$_6$ alkynyl group, —C(O)R$^7$, or —C(O)OR$^7$;
R$^6$ represents halogen atom, cyano group, C$_3$-C$_6$ cycloalkyl group, C$_1$-C$_4$ alkoxy group, C$_1$-C$_4$ haloalkoxy group, C$_1$-C$_4$ alkylthio group, C$_1$-C$_4$ haloalkylthio group, C$_1$-C$_4$ alkylsulfonyl group, C$_1$-C$_4$ haloalkylsulfonyl group, —C(O)N(R$^{13}$)R$^{12}$, —C(R$^{15}$)=NOH, —C(R$^{15}$)=NOR$^{14}$, phenyl group, phenyl group substituted by (Z)$_{p1}$, D-11 to D-14, D-18, D-19, D-25, D-26, D-31, D-32, D-36, D-38, D-41, D-44, D-45, E-1, E-2, or E-5;
Z represents halogen atom, cyano group, nitro group, C$_1$-C$_4$ alkyl group, C$_1$-C$_4$ haloalkyl group, C$_1$-C$_4$ alkoxy group, C$_1$-C$_4$ haloalkoxy group, C$_1$-C$_4$ alkylsulfonyl group, or C$_1$-C$_4$ haloalkylsulfonyl group, and when p1, p2, p3, or p4 represents 2 or higher integer, each Z can be identical with or different from each other;
R$^7$ represents C$_1$-C$_6$ alkyl group, C$_1$-C$_6$ haloalkyl group, C$_1$-C$_6$ alkoxy(C$_1$-C$_4$)alkyl group, C$_1$-C$_6$ alkylthio(C$_1$-C$_4$)alkyl group, C$_3$-C$_8$ cycloalkyl group, C$_3$-C$_6$ alkenyl group, or C$_3$-C$_6$ alkynyl group;
R$^8$ represents C$_1$-C$_4$ haloalkyl group, —C(O)R$^{12}$, —C(O)OR$^{12}$, phenyl group, phenyl group substituted by (Z)$_{p1}$, D-3, D-4, D-18, D-38, D-41, D-42, D-44, or D-45;
R$^9$ represents hydrogen atom or C$_1$-C$_6$ alkyl group;
R$^{10}$ represents C$_1$-C$_4$ alkyl group;
R$^{11}$ represents C$_1$-C$_4$ alkyl group, when q1, q2, q3, or q4 represents 2 or higher integer, each R$^{11}$ can be identical with or different from each other, and two $R^{11}$s substituting on the same carbon atom indicate that the two $R^{11}$s can form an oxo ring together;

$R^{12}$ represents $C_1$-$C_4$ alkyl group, $C_1$-$C_4$ haloalkyl group, $C_3$-$C_6$ cycloalkyl($C_1$-$C_4$)alkyl group, $C_3$-$C_6$ cycloalkyl group, $C_3$-$C_6$ alkenyl group, or $C_3$-$C_6$ alkynyl group;

$R^{13}$ represents hydrogen atom or $C_1$-$C_4$ alkyl group;

$R^{14}$ represents $C_1$-$C_4$ alkyl group or $C_1$-$C_4$ haloalkyl group; and $R^{15}$ represents hydrogen atom or $C_1$-$C_4$ alkyl group.

* * * * *